(12) United States Patent
Vakalopoulos et al.

(10) Patent No.: US 10,174,021 B2
(45) Date of Patent: Jan. 8, 2019

(54) SUBSTITUTED PYRAZOLO[1,5-A]PYRIDINES AND THEIR USE

(71) Applicant: BAYER PHARMA AKTIENGESELLSCHAFT, Berlin (DE)

(72) Inventors: Alexandros Vakalopoulos, Hilden (DE); Damian Brockschnieder, Haan (DE); Frank Wunder, Wuppertal (DE); Johannes-Peter Stasch, Grottaferrata (IT); Tobias Marquardt, Wuppertal (DE); Lisa Dietz, Wuppertal (DE); Volkhart Min-Jian Li, Velbert (DE)

(73) Assignee: BAYER PHARMA AKTIENGESELLSCHAFT, Berlin (DE)

(*) Notice: Subject to any disclaimer, the term of this patent is extended or adjusted under 35 U.S.C. 154(b) by 0 days.

(21) Appl. No.: 15/531,993

(22) PCT Filed: Nov. 30, 2015

(86) PCT No.: PCT/EP2015/078008
§ 371 (c)(1),
(2) Date: May 31, 2017

(87) PCT Pub. No.: WO2016/087342
PCT Pub. Date: Jun. 9, 2016

(65) Prior Publication Data
US 2017/0313700 A1      Nov. 2, 2017

(30) Foreign Application Priority Data
Dec. 2, 2014   (EP) ..................... 14195899

(51) Int. Cl.
| | |
|---|---|
| *C07D 471/04* | (2006.01) |
| *A61K 31/4738* | (2006.01) |
| *C07D 487/04* | (2006.01) |
| *A61K 9/00* | (2006.01) |
| *A61K 9/08* | (2006.01) |
| *A61K 9/20* | (2006.01) |
| *A61K 31/437* | (2006.01) |
| *A61K 31/444* | (2006.01) |
| *A61K 31/496* | (2006.01) |
| *A61K 31/506* | (2006.01) |
| *A61K 31/519* | (2006.01) |
| *A61K 31/53* | (2006.01) |
| *A61K 31/5377* | (2006.01) |
| *A61K 45/06* | (2006.01) |
| *C07D 519/00* | (2006.01) |

(52) U.S. Cl.
CPC .......... *C07D 471/04* (2013.01); *A61K 9/0019* (2013.01); *A61K 9/0053* (2013.01); *A61K 9/08* (2013.01); *A61K 9/20* (2013.01); *A61K 31/437* (2013.01); *A61K 31/444* (2013.01); *A61K 31/4738* (2013.01); *A61K 31/496* (2013.01); *A61K 31/506* (2013.01); *A61K 31/519* (2013.01); *A61K 31/53* (2013.01); *A61K 31/5377* (2013.01); *A61K 45/06* (2013.01); *C07D 487/04* (2013.01); *C07D 519/00* (2013.01)

(58) Field of Classification Search
CPC .................................................. C07D 471/04
See application file for complete search history.

(56) References Cited

U.S. PATENT DOCUMENTS

| | | |
|---|---|---|
| 5,698,704 A | 12/1997 | Jackson |
| 6,180,656 B1 | 1/2001 | Furstner et al. |

(Continued)

FOREIGN PATENT DOCUMENTS

| | | |
|---|---|---|
| WO | WO 89/03833 A1 | 5/1989 |
| WO | WO 96/34866 A1 | 11/1996 |

(Continued)

OTHER PUBLICATIONS

Artursson et al., "Correlation Between Oral Drug Absorption in Humans and Apparent Drug Permeability Coefficients in Human Intestinal Epithelial (CACO-2) Cells," Biochemical and Biophysical Research Communications, (Mar. 29, 1991, vol. 175, No. 3, pp. 880-885.

(Continued)

*Primary Examiner* — Brian E McDowell
(74) *Attorney, Agent, or Firm* — Ice Miller LLP

(57) ABSTRACT

The present application relates to novel substituted pyrazolo [1,5-a]pyridines of the formula (I-A)

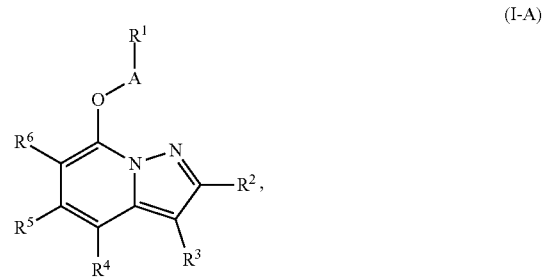

to processes for preparation thereof, to the use thereof, alone or in combinations, for treatment and/or prophylaxis of diseases, and to the use thereof for production of medicaments for treatment and/or prophylaxis of diseases, especially for treatment and/or prophylaxis of cardiovascular disorders.

7 Claims, No Drawings

(56) References Cited

U.S. PATENT DOCUMENTS

| | | |
|---|---|---|
| 8,129,423 B2 | 3/2012 | Ackermann et al. |
| 8,969,045 B2 | 3/2015 | Burkhardt et al. |
| 9,126,998 B2 | 9/2015 | Vakalopoulos et al. |
| 2013/0210824 A1 | 8/2013 | Follmann et al. |
| 2014/0128425 A1 | 5/2014 | Vakalopoulos et al. |
| 2016/0010143 A1 | 1/2016 | Burkhardt et al. |

FOREIGN PATENT DOCUMENTS

| | | |
|---|---|---|
| WO | WO 98/16223 A1 | 4/1998 |
| WO | WO 2008/061626 A1 | 5/2008 |
| WO | 2010/123792 A1 | 10/2010 |
| WO | WO 2010/117787 A2 | 10/2010 |
| WO | WO 2012/072512 A1 | 6/2012 |

OTHER PUBLICATIONS

Bai et al., "Lewis Acid Catalyzed Intramolecular [4+2] and [3+2] Cross-Cycloaddition of Alkynylcyclopropane Ketones with Carbonyl Compounds and Imines," Angewandte Chemie International Edition, (Apr. 23, 2012), vol. 51, Issue 17, pp. 4112-4116.

Bergmann et al., "Autoxidation, of Hexaethylbenzene," 644. Organic Fluorine Compounds. Part XXVII. Fluorinated α-Aminoisobutyric Acids, Journal of the Chemical Society, (1963), pp. 3462-3463.

Chen et al., "Radical Formation in the Oxidation of 2,2'-Azo-2-methyl-6-heptene by Thianthrene Cation Radical," The Journal of Organic Chemistry, (1996), vol. 61, No. 14, pp. 4716-4719.

Deng et al., "Studies on Phosphoroheterocycle Chemistry II: A Simple and New Route to 1,3,2-Diazaphospholidine-4-thione 2-sulfide Derivatives," Synthesis, (2001)), No. 16, pp. 2445-2449.

Fernandez et al. "Design, Synthesis and Structure-Activity-Relationship of 1,5-Tetrahydronaphthyridines as CETP Inhibitors," Bioorganic & Medicinal Chemistry Letters, (May 1, 2012), vol. 22, No. 9, pp. 3056-3062.

Freifelder et al., "Synthesis of Primary 1,2-Diamines by Hydrogenation of α-Aminonitriles," Journal of the American, Chemical Society, (Feb. 1960), vol. 82, No. 3, pp. 696-698.

Hiroi et al., "A Novel Method for Direct Construction of Indole Skeletons by Intramolecular Carbopalladation of Allenes Followed by Nucleophilic Substitution," Synlett, (2001, vol. 2001, No. 2, pp. 263-265.

Hjørringgaard et al., "An Automatic Solid-Phase Synthesis of Peptaibols," The Journal of Organic Chemistry, (2009), vol. 74, No. 3, pp. 1329-1332.

Hossain et al., "Synthesis of Vicinal Diamino-Endo, Cis-Norbornene Derivatives," Synthetic Communications, (2012), vol. 42, No. 8, pp. 1200-1210.

Klapper et al., "Poly(Methykenamin)—Synthese Eines Polymers Mit Der Höchstmöglichen Zahl an Aminogruppen an Einer Polymeren Hauptkefte," Angewandte Chemie, (Oct. 6, 2003), vol. 115, No. 38, pp. 4835-4838.

Ko et al., "Universal Peptidomimetics," Journal of the American Chemical Society, (2011), vol. 133, No. 3, pp. 462-477.

Kojima et al., "Phosphodiesterase Inhibitors. Part 6: Design, Synthesis, and Structure-Activity Relationships of PDE4-Inhibitory Pyrazolo[1,5-α]Pyridines with Anti-Inflammatory Activity," Bioorganic & Medicinal Chemistry Letters, (Aug. 8, 2013), vol. 23, No. 19, pp. 5311-5316.

McConathy et al., "Radiolabeled Amino Acids for Tumor Imaging with PET: Radiosynthesis and Biological Evaluation of 2-Amino-3-[18F]Fluoro-2-Methylpropanoic Acid and 3-[18F]Fluoro-2-Methyl-2-(Methylamino Propanoic Acid," Journal of Medicinal Chemistry, (2002), vol. 45, No. 11, pp. 2240-2249.

Mikami et al., "Applications of the Tandem [2,3]-Wittig-Oxy-Cope Rearrangement to Syntheses of exo-Brevicomin and Oxocrinol. The Scope and Limitation of the Sigmatropic Sequences as a Synthetic Method for δ,ε-Unsaturated Ketones," Chemistry Letters, (1982), vol. 11, No. 9, pp. 1349-1352.

Ogrel et al., "Synthesis of 15N-Labelled D-Isovaline and α-Aminoisobutyric Acid," European Journal of Organic Chemistry, (Mar. 2000), vol. 2000, Issue 5, pp. 857-859.

Rubottom et al., "Preparation of Methyl Ketones by the Sequential Treatment of Carboxylic Acids with Methyllithium and Chlorotrimethylsilane," The Journal of Organic Chemistry, (1983), vol. 48, No. 9, pp. 1550-1552.

Scholz et al., "cis-1,2-Cyclobutandiamine Durch Photosensibilisierte Cyclo-Addition von 1,3-Diacetyl-4-Imidazolin-2-Onen an Olefine," European Journal of Organic Chemistry, Liebigs Ann. Chem., (Feb. 27, 1981), vol. 1981, No. 2, pp. 248-255.

Straub et al., "NO-Independent Stimulators of Soluble Guanylate Cyclase," Bioorganic & Medicinal Chemistry Letters, (Mar. 26, 2011), vol. 11, Issue 6, pp. 781-784.

Van Den Buuse, "Circadian Rhythms of Blood Pressure, Heart Rate, and Locomotor Activity in Spontaneously Hypertensive Rats as Measured with Radio-Telemetry," Physiology & Behavior, (Apr. 1994), vol. 55, Issue 4, pp. 783-787.

Von Der Saal et al., "Cyclopropandiamine, 4. Synthese und 1H-NMR-Spektren Diastereomerenreiner 1,2-Cyclopropandiamine und 1,2-Cyclopropandiammonium-dibromide," European Journal of Organic Chemistry, Liebigs Ann. Chem., (Jun. 13, 1994), vol. 1994, No. 6, pp. 569-579.

Witte et al., "Experimental heart failure in rats: effects on cardiovascular circadian rhythms and on myocardial 3-adrenergic signaling," Cardiovascular Research, (Aug. 2000), vol. 47, No. 2, pp. 350-358.

Wube et al., "Design, Synthesis and Antimycobacterial Activities of 1-Methyl-2-Alkenyl-4(1H)-Quinolones," Bioorganic & Medicinal Chemistry, (2011), vol. 19, No. 1, pp. 567-579.

International Search Report (PCT/ISA/210) dated Jan. 19, 2016, by the European Patent Office as the International Searching Authority for International Application No. PCT/EP2015/078008.

Written Opinion (PCT/ISA/237) dated Jan. 19, 2016, by the European Patent Office as the International Searching Authority for International Application No. PCT/EP2015/078008.

Goldberg et al., "Stimulation of Human Platelet Guanylate Cyclase by Fatty Acids", The Journal of Biological Chemistry, vol. 252, No. 4, 1977, pp. 1279-1285.

Hamill et al., "Improved Patch-Clamp Techniques for High-Resolution Current Recording from Cells and Cell-Free Membrane Patches", Pflügers Archiv, vol. 391, 1981, pp. 85-100.

Hassan et al., "Aryl-Aryl Bond Formation One Century after the Discovery of the Ullmann Reaction", Chem. Rev. 2002, vol. 102, pp. 1359-1469.

Himmel, "Suitability of commonly used excipients for electrophysiological in-vitro safety pharmacology assessment of effects on hERG potassium current and on rabbit Purkinje fiber action potential", Journal of Pharmacological and Toxicological Methods, 2007, vol. 56, pp. 145-158.

Hoenicka et al., "Purified soluble guanylyl cyclase expressed in a baculovirus/Sf9 system: stimulation by YC-1, nitric oxide, and carbon monoxide", J. Mol. Med., 1999, Bd. 77, pp. 14-23.

Mülsch et al., "Effect of YC-1, an NO-independent, superoxide-sensitive stimulator of soluble guanylyl cyclase, on smooth muscle responsiveness to nitrovasodilators", British Journal of Pharmacology, 1997, 120, pp. 681-689.

Pettibone et al., "A Structurally Novel Stimulator of Guanylate Cyclase With Long-Lasting Hypotensive Activity in the Dog", European Journal of Pharmacology, 1985, Bd. 116, pp. 307-312.

Scheel et al., "Introduction of a Modular Automated Voltage-Clamp Platform and Its Correlation with Manual Human Ether-á-go-go Related Gene Voltage-Clamp Data", Assay Drug Dev Technol 2011, vol. 9, pp. 600-607.

Stasch et al., "Cardiovascular actions of a novel NO-independent guanylyl cyclase stimulator, BAY 41/8543: in vivo studies", British Journal of Pharmacology, 2002, vol. 135, No. 2, pp. 344-355.

Wu et al., "YC-1, a novel activator of platelet guanylate cyclase", Blood, 1994, vol. 84, pp. 4226-4233.

Wunder et al., "A cell-based cGMP assay useful for ultra-high-throughput screening and identification of modulators of the nitric oxide/cGMP pathway", Analytical Biochemistry, 2005, vol. 339, pp. 104-112.

(56) References Cited

OTHER PUBLICATIONS

Yu et al., "Vasorelaxant effect of isoliquiritigenin, a novel soluble guanylate cyclase activator, in rat aorta", British Journal of Pharmacology, 1995, 114, pp. 1587-1594.

Zhou et al., "Properties of HERG Channels Stably Expressed in HEK 293 Cells Studied at Physiological Temperature", Biophysical Journal, vol. 74, 1998, pp. 230-241.

SUBSTITUTED PYRAZOLO[1,5-A]PYRIDINES AND THEIR USE

The present application relates to novel substituted pyrazolo[1,5-a]pyridines and imidazo[1,2-a]pyrazines, to processes for preparation thereof, to the use thereof, alone or in combinations, for treatment and/or prophylaxis of diseases, and to the use thereof for production of medicaments for treatment and/or prophylaxis of diseases, especially for treatment and/or prophylaxis of cardiovascular disorders.

One of the most important cellular transmission systems in mammalian cells is cyclic guanosine monophosphate (cGMP). Together with nitrogen monoxide (NO), which is released from the endothelium and transmits hormonal and mechanical signals, it forms the NO/cGMP system. Guanylate cyclases catalyse the biosynthesis of cGMP from guanosine triphosphate (GTP). The representatives of this family known to date can be classified into two groups either by structural features or by the type of ligands: the particulate guanylate cyclases which can be stimulated by natriuretic peptides, and the soluble guanylate cyclases which can be stimulated by NO. The soluble guanylate cyclases consist of two subunits and very probably contain one heme per heterodimer, which is part of the regulatory centre. This is of central importance for the activation mechanism. NO is able to bind to the iron atom of heme and thus markedly increase the activity of the enzyme. Heme-free preparations cannot, by contrast, be stimulated by NO. Carbon monoxide (CO) is also able to bind to the central iron atom of heme, but the stimulation by CO is much less than that by NO.

By forming cGMP, and owing to the resulting regulation of phosphodiesterases, ion channels and protein kinases, guanylate cyclase plays an important role in various physiological processes, in particular in the relaxation and proliferation of smooth muscle cells, in platelet aggregation and platelet adhesion and in neuronal signal transmission, and also in disorders which are based on a disruption of the aforementioned processes. Under pathophysiological conditions, the NO/cGMP system can be suppressed, which can lead, for example, to hypertension, platelet activation, increased cell proliferation, endothelial dysfunction, atherosclerosis, angina pectoris, heart failure, myocardial infarction, thromboses, stroke and sexual dysfunction.

Owing to the expected high efficiency and low level of side effects, a possible NO-independent treatment for such disorders by targeting the influence of the cGMP signal pathway in organisms is a promising approach.

Hitherto, for the therapeutic stimulation of the soluble guanylate cyclase, use has exclusively been made of compounds such as organic nitrates whose effect is based on NO. The latter is formed by bioconversion and activates soluble guanylate cyclase by attacking the central iron atom of heme. In addition to the side effects, the development of tolerance is one of the crucial disadvantages of this mode of treatment.

In recent years, some substances have been described which stimulate soluble guanylate cyclase directly, i.e. without prior release of NO, such as, for example, 3-(5'-hydroxymethyl-2'-furyl)-1-benzylindazole [YC-1; Wu et al., Blood 84 (1994), 4226; Mülsch et al., Brit. J. Pharmacol. 120 (1997), 681], fatty acids [Goldberg et al., J. Biol. Chem. 252 (1977), 1279], diphenyliodonium hexafluorophosphate [Pettibone et al., Eur. J. Pharmacol. 116 (1985), 307], isoliquiritigenin [Yu et al., Brit. J. Pharmacol. 114 (1995), 1587] and various substituted pyrazole derivatives (WO 98/16223).

WO 2012/072512-A1 and WO 2010/117787, among other documents, disclose various pyrazolo[1,5-a]pyridine derivatives which can be used for treatment of disorders. WO 89/03833 A1 and WO 96/34866 A1 describe various imidazo[1,2-a]pyrazine derivatives which can be used for treatment of disorders.

It was an object of the present invention to provide novel substances which act as stimulators of soluble guanylate cyclase and are suitable as such for the treatment and/or prophylaxis of diseases.

The present invention provides compounds of the general formulae (I-A) and (I-B)

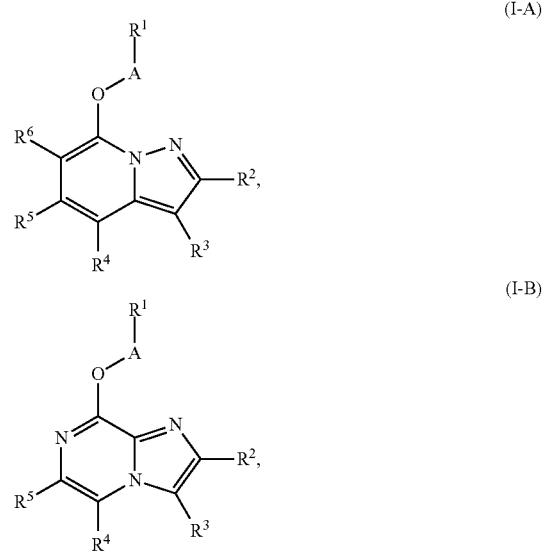

in which
A represents $CH_2$, $CD_2$ or $CH(CH_3)$,
$R^1$ represents $(C_4-C_6)$-alkyl, $(C_3-C_7)$-cycloalkyl, pyridyl or phenyl,
  where $(C_4-C_6)$-alkyl may be up to hexasubstituted by fluorine,
  where $(C_3-C_7)$-cycloalkyl may be substituted by 1 to 4 substituents independently of one another selected from the group consisting of fluorine, trifluoromethyl and $(C_1-C_4)$-alkyl,
  where pyridyl is substituted by 1 or 2 substituents independently of one another selected from the group consisting of halogen, cyano and $(C_1-C_4)$-alkyl,
  and
  where phenyl may be substituted by 1 to 4 substituents independently of one another selected from the group consisting of halogen, cyano, monofluoromethyl, difluoromethyl, trifluoromethyl, $(C_1-C_4)$-alkyl and $(C_1-C_4)$-alkoxy,
$R^2$ represents hydrogen, $(C_1-C_4)$-alkyl, $(C_1-C_4)$-alkoxymethyl, cyclopropyl, cyclobutyl, monofluoromethyl, difluoromethyl or trifluoromethyl,
$R^3$ represents phenyl or 5- to 10-membered heteroaryl,
  where phenyl may be substituted by 1 to 3 substituents independently of one another selected from the group consisting of halogen, cyano, trifluoromethyl, difluoromethyl, $(C_1-C_6)$-alkyl, $(C_1-C_4)$-alkoxycarbonyl, $(C_1-C_4)$-alkylcarbonyl, hydroxycarbonyl, —(C=O) $NR^7R^8$, $(C_1-C_4)$-alkylsulphonyl, $(C_3-C_6)$-cycloalkylsulphonyl, $(C_1-C_4)$-alkylthio, $(C_1-C_4)$- alkoxy, trifluoromethoxy, difluoromethoxy, phenoxy, hydroxy, amino, morpholinyl, piperidinyl, pyrrolidinyl, piperazinyl and $(C_3-C_6)$-cycloalkyl,
in which amino may be substituted by 1 or 2 substituents independently of one another selected from the group consisting of $(C_1-C_6)$-alkyl, $(C_1-C_4)$-alkylcarbonyl, $(C_3-C_6)$-cycloalkylsulphonyl, $(C_1-C_4)$-alkylsulphonyl and methoxy-$(C_1-C_4)$-alkyl,
in which $(C_1-C_6)$-alkyl may be substituted by amine,
in which $(C_1-C_6)$-alkyl may be substituted by 1 or 2 substituents selected from the group consisting of fluorine, trifluoromethoxy, —(C=O)NR$^7$R$^8$, $(C_1-C_4)$-alkoxy, $(C_3-C_6)$-cycloalkyl, morpholinyl, piperidinyl, pyrrolidinyl, piperazinyl, hydroxy and amino,
in which amino may be substituted by 1 or 2 substituents independently of one another selected from $(C_1-C_6)$-alkyl, $(C_1-C_4)$-alkylcarbonyl, $(C_1-C_4)$-alkoxycarbonyl, $(C_3-C_6)$-cycloalkylsulphonyl, $(C_1-C_4)$-alkylsulphonyl and methoxy-$(C_1-C_4)$-alkyl,
and in which
R$^7$ and R$^8$ each independently of one another represent hydrogen, $(C_1-C_4)$-alkyl or $(C_3-C_7)$-cycloalkyl,
where 5- to 10-membered heteroaryl may be substituted by 1 to 3 substituents independently of one another selected from the group consisting of fluorine, chlorine, cyano, $(C_1-C_6)$-alkyl, $(C_1-C_4)$-alkoxy, amino, $(C_1-C_4)$-alkoxycarbonyl, hydroxycarbonyl, —(C=O)NR$^7$R$^8$, phenyl, pyridyl, pyrimidyl, 1,3-thiazol-5-yl, pyrrolidinyl, piperidinyl, morpholinyl, piperazinyl and $(C_3-C_7)$-cycloalkyl,
in which $(C_1-C_6)$-alkyl may be substituted by 1 to 3 substituents selected from the group consisting of fluorine, cyano, hydroxy, amino, trifluoromethyl, difluoromethyl, $(C_1-C_4)$-alkylsulphonyl, $(C_1-C_4)$-alkylcarbonyl, $(C_1-C_4)$-alkoxycarbonyl, hydroxycarbonyl, —(C=O)NR$^7$R$^8$ $(C_1-C_4)$-alkoxy, phenoxy, phenyl, pyridyl, pyrimidyl, 5-membered heteroaryl, $(C_3-C_7)$-cycloalkyl, morpholinyl, piperidinyl, pyrrolidinyl, piperazinyl, 1,1-dioxidothiomorpholin-4-yl and azetidine,
in which 5-membered heteroaryl may be substituted by 1 to 3 substituents selected from the group consisting of halogen, $(C_1-C_4)$-alkyl and $(C_1-C_4)$-alkoxy,
in which
R$^7$ and R$^8$ each independently of one another represent hydrogen, $(C_1-C_4)$-alkyl or $(C_3-C_7)$-cycloalkyl,
in which piperidinyl may be substituted by 1 to 4 fluorine substituents,
in which phenyl may be substituted by 1 to 3 substituents selected from the group consisting of halogen, $(C_1-C_4)$-alkyl and $(C_1-C_4)$-alkoxy,
in which azetidine may be substituted by hydroxy,
in which amino may be substituted by 1 or 2 $(C_1-C_4)$-alkyl substituents,
and
in which piperazinyl may be substituted by 1 to 3 substituents independently of one another selected from the group consisting of $(C_1-C_4)$-alkyl, $(C_3-C_7)$-cycloalkyl and trifluoromethyl,
in which $(C_3-C_7)$-alkyl may be substituted by 1 or 2 substituents independently of one another selected from the group consisting of halogen, $(C_1-C_6)$-alkyl, $(C_1-C_4)$-alkoxycarbonyl and hydroxycarbonyl,
in which $(C_1-C_4)$-alkoxy may be substituted by amino,
in which amino may be substituted by 1 or 2 substituents independently of one another selected from $(C_1-C_6)$-alkyl, $(C_1-C_4)$-alkylcarbonyl, $(C_3-C_6)$-cycloalkylsulphonyl and $(C_1-C_4)$-alkylsulphonyl,
in which $(C_1-C_6)$-alkyl may be substituted by amino, and
in which $(C_1-C_6)$-alkyl may be substituted up to five times by fluorine,
in which phenyl, pyridyl and pyrimidyl may be substituted by 1 or 2 substituents selected from the group consisting of methyl, ethyl and fluorine,
in which
R$^7$ and R$^8$ each independently of one another represent hydrogen, $(C_1-C_4)$-alkyl or $(C_3-C_7)$-cycloalkyl,
or
R$^3$ represents a group of the formula

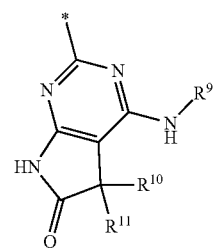

where
\* represents the point of attachment to the pyrazolopyridine or the imidazopyrazine,
R$^9$ represents hydrogen or $(C_1-C_6)$-alkyl,
where $(C_1-C_6)$-alkyl may be substituted by amino, and
in which $(C_1-C_6)$-alkyl may be substituted up to five times by fluorine,
R$^{10}$ represents hydrogen, methyl or ethyl,
R$^{11}$ represents hydrogen, methyl, ethyl, trifluoromethyl or cyclopropyl,
or
R$^{10}$ and R$^{11}$ together with the carbon atom to which they are attached form a 3- to 6-membered carbocycle,
R$^4$ represents hydrogen,
R$^5$ represents hydrogen, halogen, cyano, difluoromethyl, trifluoromethyl, $(C_1-C_4)$-alkyl, $(C_3-C_7)$-cycloalkyl, $(C_2-C_4)$-alkynyl, $(C_1-C_4)$-alkylamino, difluoromethoxy, trifluoromethoxy, $(C_1-C_4)$-alkoxy, amino, 4- to 7-membered heterocyclyl or 5- or 6-membered heteroaryl,
R$^6$ represents hydrogen, cyano or halogen,
and the N-oxides, salts, solvates, salts of the N-oxides and solvates of the N-oxides and salts thereof.

Compounds according to the invention are the compounds of the formulae (I-A) and (I-B) and their salts, solvates and solvates of the salts, the compounds, comprised by formulae (I-A) and (I-B), of the formulae mentioned below and their salts, solvates and solvates of the salts and the compounds comprised by formulae (I-A) and (I-B), mentioned below as exemplary embodiments, and their salts, solvates and solvates of the salts, if the compounds, comprised by formulae (I-A) and (I-B), mentioned below are not already salts, solvates and solvates of the salts.

Preferred salts in the context of the present invention are physiologically acceptable salts of the compounds according to the invention. Also encompassed are salts which are not themselves suitable for pharmaceutical applications but can be used, for example, for isolation or purification of the compounds according to the invention.

Physiologically acceptable salts of the compounds of the invention include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, formic acid, acetic acid, trifluoroacetic acid, propionic acid, lactic acid, tartaric acid, malic acid, citric acid, fumaric acid, maleic acid and benzoic acid.

Physiologically acceptable salts of the compounds of the invention also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates in the context of the invention are described as those forms of the compounds according to the invention which form a complex in the solid or liquid state by coordination with solvent molecules. Hydrates are a specific form of the solvates in which the coordination is with water. Solvates preferred in the context of the present invention are hydrates.

The compounds of the invention may, depending on their structure, exist in different stereoisomeric forms, i.e. in the form of configurational isomers or else, if appropriate, as conformational isomers (enantiomers and/or diastereomers, including those in the case of atropisomers). The present invention therefore encompasses the enantiomers and diastereomers, and the respective mixtures thereof. The stereoisomerically homogeneous constituents can be isolated from such mixtures of enantiomers and/or diastereomers in a known manner; chromatographic processes are preferably used for this purpose, especially HPLC chromatography on an achiral or chiral phase.

If the compounds according to the invention can occur in tautomeric forms, the present invention encompasses all the tautomeric forms.

The present invention also encompasses all suitable isotopic variants of the compounds according to the invention. An isotopic variant of a compound of the invention is understood here to mean a compound in which at least one atom within the compound of the invention has been exchanged for another atom of the same atomic number, but with a different atomic mass from the atomic mass which usually or predominantly occurs in nature. Examples of isotopes which can be incorporated into a compound of the invention are those of hydrogen, carbon, nitrogen, oxygen, phosphorus, sulphur, fluorine, chlorine, bromine and iodine, such as $^{2}H$ (deuterium), $^{3}H$ (tritium), $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$. Particular isotopic variants of a compound according to the invention, especially those in which one or more radioactive isotopes have been incorporated, may be beneficial, for example, for the examination of the mechanism of action or of the active ingredient distribution in the body; due to the comparatively easy preparability and detectability, especially compounds labelled with $^{3}H$ or $^{14}C$ isotopes are suitable for this purpose. In addition, the incorporation of isotopes, for example of deuterium, may lead to particular therapeutic benefits as a consequence of greater metabolic stability of the compound, for example an extension of the half-life in the body or a reduction in the active dose required; such modifications of the compounds according to the invention may therefore in some cases also constitute a preferred embodiment of the present invention. Isotopic variants of the compounds of the invention can be prepared by the processes known to those skilled in the art, for example by the methods described further down and the procedures described in the working examples, by using corresponding isotopic modifications of the respective reagents and/or starting materials.

The present invention additionally also encompasses prodrugs of the compounds according to the invention. The term "prodrugs" in this context refers to compounds which may themselves be biologically active or inactive but are reacted (for example metabolically or hydrolytically) to give compounds according to the invention during their residence time in the body.

In the context of the present invention, unless specified otherwise, the substituents are defined as follows:

Alkyl in the context of the invention is a straight-chain or branched alkyl radical having the particular number of carbon atoms specified. By way of example and with preference, mention may be made of the following: methyl, ethyl, n-propyl, isopropyl, n-butyl, isobutyl, 1-methylpropyl, tert-butyl, n-pentyl, isopentyl, 1-ethylpropyl, 1-methylbutyl, 2-methylbutyl, 3-methylbutyl, n-hexyl, 1-methylpentyl, 2-methylpentyl, 3-methylpentyl, 4-methylpentyl, 3,3-dimethylbutyl, 1-ethylbutyl, 2-ethylbutyl.

Cycloalkyl or carbocycle or carbocyclyl in the context of the invention is a monocyclic, bicyclic or tricyclic saturated alkyl radical having the particular number of carbon atoms specified. By way of example and with preference, mention may be made of the following: cyclopropyl, cyclobutyl, cyclopentyl, cyclohexyl, cycloheptyl and adamantyl.

Alkenyl in the context of the invention is a straight-chain or branched alkenyl radical having 2 to 6 carbon atoms and one or two double bonds. Preference is given to a straight-chain or branched alkenyl radical having 2 to 4 carbon atoms and one double bond. By way of example and with preference, mention may be made of the following: vinyl, allyl, isopropenyl and n-but-2-en-1-yl.

Alkynyl in the context of the invention is a straight-chain or branched alkynyl radical having 2 to 6 carbon atoms and one triple bond. By way of example and with preference, mention may be made of the following: ethynyl, n-prop-1-yn-1-yl, n-prop-2-yn-1-yl, n-but-2-yn-1-yl and n-but-3-yn-1-yl.

Alkanediyl in the context of the invention is a straight-chain or branched divalent alkyl radical having 1 to 4 carbon atoms. By way of example and with preference, mention may be made of the following: methylene, 1,2-ethylene, ethane-1,1-diyl, 1,3-propylene, propane-1,1-diyl, propane-1,2-diyl, propane-2,2-diyl, 1,4-butylene, butane-1,2-diyl, butane-1,3-diyl and butane-2,3-diyl.

Alkoxy in the context of the invention is a straight-chain or branched alkoxy radical having 1 to 4 carbon atoms. By way of example and with preference, mention may be made of the following: methoxy, ethoxy, n-propoxy, isopropoxy, 1-methylpropoxy, n-butoxy, isobutoxy and tert-butoxy.

Alkoxycarbonyl in the context of the invention is a straight-chain or branched alkoxy radical having 1 to 4 carbon atoms and a carbonyl group attached to the oxygen atom. By way of example and with preference, mention may be made of the following: methoxycarbonyl, ethoxycarbonyl, n-propoxycarbonyl, isopropoxycarbonyl and tert-butoxycarbonyl.

Alkylsulfonyl in the context of the invention is a straight-chain or branched alkyl radical which has 1 to 4 carbon atoms and is attached via a sulfonyl group. The following may be mentioned by way of example and by way of preference: methylsulfonyl, ethylsulfonyl, n-propylsulfonyl, isopropylsulfonyl, n-butylsulfonyl and tert-butylsulfonyl.

Heterocycle or heterocyclyl in the context of the invention is a monocyclic saturated heterocycle which has a total of 4 to 7 ring atoms or 5 to 10 ring atoms, contains one or two ring heteroatoms from the group consisting of N, O, S, SO and/or $SO_2$ and is attached via a ring carbon atom or, where appropriate, a ring nitrogen atom. The following may be mentioned by way of example: azetidinyl, oxetanyl, pyrrolidinyl, pyrazolidinyl, tetrahydrofuranyl, thiolanyl, piperidinyl, piperazinyl, tetrahydropyranyl, tetrahydrothiopyranyl, morpholinyl, thiomorpholinyl, hexahydroazepinyl and hexahydro-1,4-diazepinyl. Preference is given to azetidinyl, oxetanyl, pyrrolidinyl, tetrahydrofuranyl, piperidinyl, piperazinyl, tetrahydropyranyl and morpholinyl.

Heteroaryl in the context of the invention is a mono- or bicyclic aromatic heterocycle (heteroaromatic) which contains up to four identical or different ring heteroatoms from the group consisting of N, O and S and is attached via a ring carbon atom or, where appropriate, via a ring nitrogen atom. By way of example and with preference, mention may be made of the following: furyl, pyrrolyl, thienyl, pyrazolyl, imidazolyl, quinolinyl, thiazolyl, oxazolyl, isoxazolyl, isothiazolyl, triazolyl, oxadiazolyl, thiadiazolyl, tetrazolyl, pyridyl, pyrimidinyl, pyridazinyl, pyrazinyl and triazinyl.

Halogen in the context of the invention includes fluorine, chlorine, bromine and iodine. Preference is given to chlorine or fluorine.

In the formula of the group that $R^3$ or $R^1$ may represent, the end point of the line marked by the symbol * and # does not represent a carbon atom or a $CH_2$ group but is part of the bond to the respective atom to which $R^3$ or $R^1$ is attached.

When radicals in the compounds according to the invention are substituted, the radicals may be mono- or polysubstituted, unless specified otherwise. In the context of the present invention, all radicals which occur more than once are defined independently of one another. Substitution by one, two or three identical or different substituents is preferred.

In the context of the present invention, the term "treatment" or "treating" includes inhibition, retardation, checking, alleviating, attenuating, restricting, reducing, suppressing, repelling or healing of a diseases a condition, a disorder, an injury or a health problem, or the development, the course or the progression of such states and/or the symptoms of such states. The term "therapy" is understood here to be synonymous with the term "treatment".

The terms "prevention", "prophylaxis" and "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

In the context of the present invention, preference is given to compounds of the formulae (I-A) and (I-B) in which A represents $CH_2$ or $CD_2$, $R^1$ represents cyclohexyl, pyridyl or phenyl,
  where cyclohexyl may be substituted up to four times by fluorine,
  where pyridyl is substituted by 1 or 2 fluorine substituents,
  and
  where phenyl may be substituted by 1 to 4 substituents independently of one another selected from the group consisting of fluorine, chlorine, cyano, methyl and methoxy, $R^2$ represents hydrogen, $(C_1-C_4)$-alkyl, cyclopropyl, difluoromethyl or trifluoromethyl, $R^3$ represents phenyl or 5- or 6-membered heteroaryl,
  where phenyl may be substituted by 1 to 3 substituents independently of one another selected from the group consisting of fluorine, chlorine, cyano, trifluoromethyl, difluoromethyl, $(C_1-C_6)$-alkyl, $(C_1-C_4)$-alkoxycarbonyl, $(C_1-C_4)$-alkylcarbonyl, hydroxycarbonyl, —(C=O)$NR^7R^8$, $(C_1-C_4)$-alkylsulphonyl, $(C_3-C_6)$-cycloalkylsulphonyl, $(C_1-C_4)$-alkoxy, trifluoromethoxy, difluoromethoxy, hydroxy, amino, morpholinyl, piperidinyl, pyrrolidinyl, piperazinyl and cyclopropyl,
    in which amino may be substituted by 1 or 2 substituents independently of one another selected from $(C_1-C_6)$-alkyl, $(C_1-C_4)$-alkylcarbonyl and $(C_1-C_4)$-alkylsulphonyl,
    in which $(C_1-C_6)$-alkyl may be substituted by 1 or 2 substituents selected from the group consisting of fluorine, trifluoromethoxy, —(C=O)$NR^7R^8$, $(C_1-C_4)$-alkoxy, $(C_3-C_6)$-cycloalkyl, morpholinyl, piperidinyl, pyrrolidinyl, piperazinyl, hydroxy and amino,
      in which amino may be substituted by 1 or 2 substituents independently of one another selected from $(C_1-C_6)$-alkyl, $(C_1-C_4)$-alkylcarbonyl and $(C_1-C_4)$-alkylsulphonyl,
    and in which
    $R^7$ and $R^8$ each independently of one another represent hydrogen, $(C_1-C_4)$-alkyl or cyclopropyl,
  where 5- or 6-membered heteroaryl may be substituted by 1 to 3 substituents independently of one another selected from the group consisting of fluorine, chlorine, cyano, $(C_1-C_6)$-alkyl, $(C_1-C_4)$-alkoxy, amino, $(C_1-C_4)$-alkoxycarbonyl, hydroxycarbonyl, —(C=O)$NR^7R^8$, phenyl, pyridyl, pyrimidyl, pyrrolidinyl, piperidinyl, morpholinyl, piperazinyl and cyclopropyl,
    in which $(C_1-C_6)$-alkyl may be substituted by 1 to 3 substituents selected from the group consisting of fluorine, cyano, hydroxy, amino, trifluoromethyl, difluoromethyl, $(C_1-C_4)$-alkylsulphonyl, $(C_1-C_4)$-alkoxycarbonyl, hydroxycarbonyl, —(C=O)$NR^7R^8$, $(C_1-C_4)$-alkoxy, phenyl, pyridyl, pyrimidyl, 5-membered heteroaryl, $(C_3-C_7)$-cycloalkyl, morpholinyl, piperidinyl, pyrrolidinyl, piperazinyl, 1,1-dioxidothiomorpholin-4-yl and azetidine,
      in which 5-membered heteroaryl may be substituted by 1 to 3 substituents selected from the group consisting of fluorine, chlorine, methyl, ethyl and methoxy,
      in which
      $R^7$ and $R^8$ each independently of one another represent hydrogen, methyl, ethyl or cyclopropyl,
      in which piperidinyl may be substituted by 1 to 4 fluorine substituents,
      in which phenyl may be substituted by 1 to 3 substituents selected from the group consisting of fluorine, methyl, ethyl and methoxy, in which amino may be substituted by 1 or 2 substituents independently of one another selected from ($C_1$-$C_6$)-alkyl and ($C_1$-$C_4$)-alkylcarbonyl,
in which ($C_1$-$C_6$)-alkyl may be substituted by amino,
in which phenyl, pyridyl and pyrimidyl may be substituted by 1 or 2 substituents selected from the group consisting of methyl, ethyl and fluorine,
and in which
$R^7$ and $R^8$ each independently of one another represent hydrogen, methyl, ethyl or cyclopropyl,
or
$R^3$ represents a group of the formula

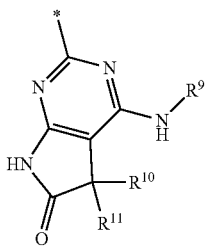

where
* represents the point of attachment to the pyrazolopyridine or the imidazopyrazine,
$R^9$ represents hydrogen or ($C_1$-$C_6$)-alkyl,
where ($C_1$-$C_6$)-alkyl may be substituted by amino,
$R^{10}$ represents methyl or ethyl,
$R^{11}$ represents methyl, ethyl, trifluoromethyl or cyclopropyl,
$R^4$ represents hydrogen,
$R^5$ represents hydrogen, fluorine, chlorine, cyano, difluoromethyl, trifluoromethyl, ($C_1$-$C_4$)-alkyl or ($C_3$-$C_5$)-cycloalkyl,
$R^6$ represents hydrogen,
and the N-oxides, salts, solvates, salts of the N-oxides and solvates of the N-oxides and salts thereof.

In the context of the present invention, preference is given to compounds of the formula (I-A) in which
A represents $CH_2$ or $CD_2$,
$R^1$ represents cyclohexyl, pyridyl or phenyl,
where cyclohexyl may be substituted up to four times by fluorine,
where pyridyl is substituted by 1 or 2 fluorine substituents,
and
where phenyl may be substituted by 1 to 4 substituents independently of one another selected from the group consisting of fluorine, chlorine, cyano, methyl and methoxy,
$R^2$ represents hydrogen, ($C_1$-$C_4$)-alkyl, cyclopropyl, difluoromethyl or trifluoromethyl,
$R^3$ represents phenyl or 5- or 6-membered heteroaryl,
where phenyl may be substituted by 1 to 3 substituents independently of one another selected from the group consisting of fluorine, chlorine, cyano, trifluoromethyl, difluoromethyl, ($C_1$-$C_6$)-alkyl, ($C_1$-$C_4$)-alkoxycarbonyl, ($C_1$-$C_4$)-alkylcarbonyl, hydroxycarbonyl, —(C=O)NR$^7$R$^8$, ($C_1$-$C_4$)-alkylsulphonyl, ($C_3$-$C_6$)-cycloalkylsulphonyl, ($C_1$-$C_4$)-alkoxy, trifluoromethoxy, difluoromethoxy, hydroxy, amino, morpholinyl, piperidinyl, pyrrolidinyl, piperazinyl and cyclopropyl, in which amino may be substituted by 1 or 2 substituents independently of one another selected from ($C_1$-$C_6$)-alkyl, ($C_1$-$C_4$)-alkylcarbonyl and ($C_1$-$C_4$)-alkylsulphonyl,
in which ($C_1$-$C_6$)-alkyl may be substituted by 1 or 2 substituents selected from the group consisting of fluorine, trifluoromethoxy, —(C=O)NR$^7$R$^8$, ($C_1$-$C_4$)-alkoxy, ($C_3$-$C_6$)-cycloalkyl, morpholinyl, piperidinyl, pyrrolidinyl, piperazinyl, hydroxy and amino,
in which amino may be substituted by 1 or 2 substituents independently of one another selected from ($C_1$-$C_6$)-alkyl, ($C_1$-$C_4$)-alkylcarbonyl and ($C_1$-$C_4$)-alkylsulphonyl,
and in which
$R^7$ and $R^8$ each independently of one another represent hydrogen, ($C_1$-$C_4$)-alkyl or cyclopropyl,
where 5- or 6-membered heteroaryl may be substituted by 1 to 3 substituents independently of one another selected from the group consisting of fluorine, chlorine, cyano, ($C_1$-$C_6$)-alkyl, ($C_1$-$C_4$)-alkoxy, amino, ($C_1$-$C_4$)-alkoxycarbonyl, hydroxycarbonyl, —(C=O)NR$^7$R$^8$, phenyl, pyridyl, pyrimidyl, pyrrolidinyl, piperidinyl, morpholinyl, piperazinyl and cyclopropyl,
in which ($C_1$-$C_6$)-alkyl may be substituted by 1 to 3 substituents selected from the group consisting of fluorine, cyano, hydroxy, amino, trifluoromethyl, difluoromethyl, ($C_1$-$C_4$)-alkylsulphonyl, ($C_1$-$C_4$)-alkoxycarbonyl, hydroxycarbonyl, —(C=O)NR$^7$R$^8$, ($C_1$-$C_4$)-alkoxy, phenyl, pyridyl, pyrimidyl, 5-membered heteroaryl, ($C_3$-$C_7$)-cycloalkyl, morpholinyl, piperidinyl, pyrrolidinyl, piperazinyl, 1,1-dioxidothiomorpholin-4-yl and azetidine,
in which 5-membered heteroaryl may be substituted by 1 to 3 substituents selected from the group consisting of fluorine, chlorine, methyl, ethyl and methoxy,
in which
$R^7$ and $R^8$ each independently of one another represent hydrogen, methyl, ethyl or cyclopropyl,
in which piperidinyl may be substituted by 1 to 4 fluorine substituents,
in which phenyl may be substituted by 1 to 3 substituents selected from the group consisting of fluorine, methyl, ethyl and methoxy,
in which amino may be substituted by 1 or 2 substituents independently of one another selected from ($C_1$-$C_6$)-alkyl and ($C_1$-$C_4$)-alkylcarbonyl,
in which ($C_1$-$C_6$)-alkyl may be substituted by amino,
in which phenyl, pyridyl and pyrimidyl may be substituted by 1 or 2 substituents selected from the group consisting of methyl, ethyl and fluorine,
and in which
$R^7$ and $R^8$ each independently of one another represent hydrogen, methyl, ethyl or cyclopropyl,
$R^4$ represents hydrogen,
$R^5$ represents hydrogen, fluorine, chlorine, cyano, difluoromethyl, trifluoromethyl, ($C_1$-$C_4$)-alkyl or ($C_3$-$C_5$)-cycloalkyl,
$R^6$ represents hydrogen,
and the N-oxides, salts, solvates, salts of the N-oxides and solvates of the N-oxides and salts thereof.

In the context of the present invention, preference is given to compounds of the formula (I-A) in which
A represents $CH_2$,
$R^1$ represents phenyl,
where phenyl is substituted up to three times by fluorine,
$R^2$ represents methyl, $R^3$ represents phenyl, pyridyl, pyrimidyl or 4-pyrazolyl,
  where phenyl may be substituted by 1 to 3 substituents independently of one another selected from the group consisting of fluorine, $(C_1-C_6)$-alkyl, hydroxycarbonyl, —(C=O)NR$^7$R$^8$, methylsulphonyl, ethylsulphonyl, amino, morpholinyl, piperidinyl, pyrrolidinyl and piperazinyl,
    in which amino may be substituted by 1 or 2 substituents independently of one another selected from $(C_1-C_6)$-alkyl, methylcarbonyl, ethylcarbonyl, methylsulphonyl and ethylsulphonyl,
    in which $(C_1-C_6)$-alkyl may be substituted by 1 or 2 substituents selected from the group consisting of fluorine, morpholinyl, piperidinyl, pyrrolidinyl, piperazinyl and amino,
      in which amino may be substituted by 1 or 2 substituents independently of one another selected from $(C_1-C_4)$-alkyl, methylcarbonyl, ethylcarbonyl, methylsulphonyl and ethylsulphonyl,
      and in which
      $R^7$ and $R^8$ each independently of one another represent hydrogen or cyclopropyl,
  where pyridyl and 4-pyrazolyl may be substituted by 1 or 2 substituents independently of one another selected from the group consisting of fluorine, chlorine, $(C_1-C_6)$-alkyl, methoxy, amino, hydroxycarbonyl, —(C=O)NR$^7$R$^8$, phenyl, pyridyl, pyrrolidinyl, piperidinyl, morpholinyl and piperazinyl,
    in which $(C_1-C_6)$-alkyl may be substituted by 1 to 3 substituents selected from the group consisting of fluorine, hydroxy, amino, hydroxycarbonyl, —(C=O)NR$^7$R$^8$, methoxy, phenyl, pyridyl, pyrazolyl, $(C_3-C_7)$-cycloalkyl, morpholinyl, piperidinyl, pyrrolidinyl and piperazinyl,
      in which pyrazolyl may be substituted by 1 or 2 methyl substituents,
      and in which
      $R^7$ and $R^8$ each independently of one another represent hydrogen, methyl, ethyl or cyclopropyl,
    in which amino may be substituted by 1 or 2 $(C_1-C_6)$-alkyl substituents,
      in which $(C_1-C_6)$-alkyl may be substituted by amino,
    in which phenyl, pyridyl and pyrimidyl may be substituted by 1 or 2 substituents selected from the group consisting of methyl, ethyl and fluorine,
    and in which
    $R^7$ and $R^8$ each independently of one another represent hydrogen, methyl or cyclopropyl,
$R^4$ represents hydrogen,
$R^5$ represents hydrogen or methyl,
$R^6$ represents hydrogen,
and the N-oxides, salts, solvates, salts of the N-oxides and solvates of the N-oxides and salts thereof.

In the context of the present invention, preference is given to compounds of the formula (I-A) in which
A represents $CH_2$,
$R^1$ represents a phenyl group of the formula

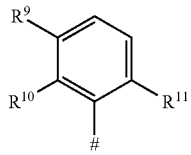

where
# represents the point of attachment to A,
and
$R^9$ represents hydrogen or fluorine,
$R^{10}$ represents fluorine,
$R^{11}$ represents fluorine,
$R^2$ represents methyl,
$R^3$ represents phenyl, 3-pyridyl, 4-pyridyl or 4-pyrazolyl,
  where phenyl in the 3-position may be substituted by fluorine, $(C_1-C_6)$-alkyl, hydroxycarbonyl, —(C=O)NR$^7$R$^8$, methylsulphonyl, ethylsulphonyl, amino, morpholinyl, piperidinyl, pyrrolidinyl and piperazinyl,
    in which amino may be substituted by 1 or 2 substituents independently of one another selected from $(C_1-C_6)$-alkyl, methylcarbonyl, ethylcarbonyl, methylsulphonyl and ethylsulphonyl,
    in which $(C_1-C_6)$-alkyl may be substituted by 1 or 2 substituents selected from the group consisting of fluorine, morpholinyl, piperidinyl, pyrrolidinyl, piperazinyl and amino,
      in which amino may be substituted by 1 or 2 substituents independently of one another selected from $(C_1-C_4)$-alkyl, methylcarbonyl, ethylcarbonyl, methylsulphonyl and ethylsulphonyl,
      and in which
      $R^7$ and $R^8$ each independently of one another represent hydrogen or cyclopropyl,
  where 3-pyridyl and 4-pyridyl may each be substituted by 1 or 2 substituents independently of one another selected from the group consisting of fluorine, chlorine, $(C_1-C_6)$-alkyl, methoxy, amino, hydroxycarbonyl, —(C=O)NR$^7$R$^8$, phenyl, pyridyl, pyrrolidinyl, piperidinyl, morpholinyl and piperazinyl,
    in which amino may be substituted by 1 or 2 $(C_1-C_6)$-alkyl substituents,
      in which $(C_1-C_6)$-alkyl may be substituted by amino,
    in which phenyl, pyridyl and pyrimidyl may be substituted by 1 or 2 substituents selected from the group consisting of methyl, ethyl and fluorine,
    and in which
    $R^7$ and $R^8$ each independently of one another represent hydrogen, methyl or cyclopropyl,
  where 4-pyrazolyl may be substituted at the 1-position by $(C_1-C_6)$-alkyl, phenyl or pyridyl,
    in which $(C_1-C_6)$-alkyl may be substituted by 1 to 3 substituents selected from the group consisting of fluorine, hydroxy, amino, methoxycarbonyl, ethoxycarbonyl, hydroxycarbonyl, —(C=O)NR$^7$R$^8$, methoxy, phenyl, pyridyl, pyrazolyl, $(C_3-C_7)$-cycloalkyl, morpholinyl, piperidinyl, pyrrolidinyl and piperazinyl,
      in which pyrazolyl may be substituted by 1 to 3 methyl substituents,
      in which
      $R^7$ and $R^8$ each independently of one another represent hydrogen, methyl, ethyl or cyclopropyl,
    in which phenyl and pyridyl may be substituted by 1 or 2 substituents selected from the group consisting of methyl, ethyl and fluorine,
$R^4$ represents hydrogen,
$R^5$ represents hydrogen or methyl,
$R^6$ represents hydrogen,
and the N-oxides, salts, solvates, salts of the N-oxides and solvates of the N-oxides and salts thereof.

Particular preference is given in the context of the present invention to compounds of the formula (I-A) in which A represents CH$_2$,
R$^1$ represents a phenyl group of the formula

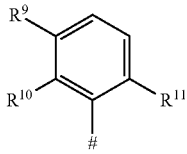

where
# represents the point of attachment to A,
and
R$^9$ represents hydrogen or fluorine,
R$^{10}$ represents fluorine,
R$^{11}$ represents fluorine,
R$^2$ represents methyl,
R$^3$ represents phenyl, 3-pyridyl, 4-pyridyl or 4-pyrazolyl,
  where phenyl in the 3-position may be substituted by (C$_1$-C$_6$)-alkyl, hydroxycarbonyl, —(C=O)NR$^7$R$^8$, methylsulphonyl, ethylsulphonyl, amino and pyrrolidinyl,
    in which amino may be substituted by 1 or 2 substituents independently of one another selected from (C$_1$-C$_6$)-alkyl, methylcarbonyl and methylsulphonyl,
    in which (C$_1$-C$_6$)-alkyl may be substituted by 1 or 2 substituents selected from the group consisting of fluorine, pyrrolidinyl and amino,
      in which amino may be substituted by 1 or 2 substituents independently of one another selected from (C$_1$-C$_4$)-alkyl, methylcarbonyl and methylsulphonyl,
    and in which
    R$^7$ and R$^8$ each independently of one another represent hydrogen or cyclopropyl,
  where 3-pyridyl and 4-pyridyl may each be substituted by 1 or 2 substituents independently of one another selected from the group consisting of fluorine, chlorine, (C$_1$-C$_6$)-alkyl, amino, hydroxycarbonyl, —(C=O)NR$^7$R$^8$, phenyl and piperazinyl,
    in which amino may be substituted by 1 or 2 (C$_1$-C$_6$)-alkyl substituents,
      in which (C$_1$-C$_6$)-alkyl may be substituted by amino,
    in which phenyl may be substituted by 1 or 2 substituents selected from the group consisting of methyl, ethyl and fluorine,
    and in which
    R$^7$ and R$^8$ each represent hydrogen,
  where 4-pyrazolyl may be substituted at the 1-position by (C$_1$-C$_6$)-alkyl or phenyl,
    in which (C$_1$-C$_6$)-alkyl may be substituted by 1 to 3 substituents selected from the group consisting of hydroxy, amino, methoxycarbonyl, hydroxycarbonyl, —(C=O)NR$^7$R$^8$, phenyl, pyrazolyl, (C$_3$-C$_7$)-cycloalkyl and morpholinyl,
      in which pyrazolyl may be substituted by 1 or 3 methyl substituents,
      in which
        R$^7$ represents hydrogen,
        R$^8$ represents cyclopropyl,
        in which phenyl and pyridyl may be substituted by 1 or 2 fluorine substituents,
R$^4$ represents hydrogen,
R$^5$ represents hydrogen or methyl,
R$^6$ represents hydrogen,
and the N-oxides, salts, solvates, salts of the N-oxides and solvates of the N-oxides and salts thereof.

In the context of the present invention, preference is given to compounds of the formula (I-B) in which
A represents CH$_2$ or CD$_2$,
R$^1$ represents or phenyl,
  where phenyl is substituted by 1 to 3 fluorine substituents,
R$^2$ represents methyl,
R$^3$ represents 5- or 6-membered heteroaryl,
  where 5- or 6-membered heteroaryl may be substituted by 1 to 3 substituents independently of one another selected from the group consisting of (C$_1$-C$_4$)-alkyl and amino,
    in which (C$_1$-C$_4$)-alkyl may be substituted by 1 to 3 substituents selected from the group consisting of hydroxy, amino, (C$_1$-C$_4$)-alkoxycarbonyl, hydroxycarbonyl, phenyl, 5-membered heteroaryl, (C$_3$-C$_7$)-cycloalkyl, morpholinyl and 1,1-dioxidothiomorpholin-4-yl,
    in which amino may be substituted by (C$_1$-C$_6$)-alkyl,
      in which (C$_1$-C$_6$)-alkyl may be substituted by amino,
or
R$^3$ represents a group of the formula

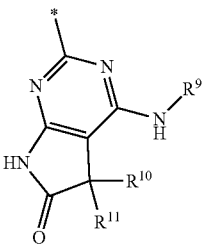

where
* represents the point of attachment to the imidazopyrazine,
R$^9$ represents hydrogen or (C$_1$-C$_6$)-alkyl,
  where (C$_1$-C$_6$)-alkyl may be substituted by amino,
R$^{10}$ represents methyl or ethyl,
R$^{11}$ represents methyl, ethyl or trifluoromethyl,
R$^4$ represents hydrogen,
R$^5$ represents hydrogen or methyl,
R$^6$ represents hydrogen,
and the N-oxides, salts, solvates, salts of the N-oxides and solvates of the N-oxides and salts thereof.

In the context of the present invention, preference is given to compounds of the formula (I-B) in which
A represents CH$_2$,
R$^1$ represents a phenyl group of the formula

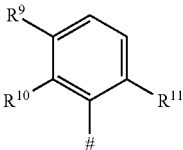

where
# represents the point of attachment to A,
and
R$^9$ represents hydrogen,
R$^{10}$ represents fluorine,
R$^{11}$ represents fluorine, $R^2$ represents methyl,
$R^3$ represents 4-pyrazolyl or 1,3,5-triazinyl,
    where 1,3,5-triazinyl is substituted two times by amino,
or
$R^3$ represents a group of the formula

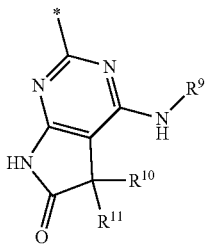

where
* represents the point of attachment to the imidazopyrazine,
$R^9$ represents hydrogen,
$R^{10}$ represents methyl,
$R^{11}$ represents methyl,
$R^4$ represents hydrogen,
$R^5$ represents methyl,
$R^6$ represents hydrogen,
and the N-oxides, salts, solvates, salts of the N-oxides and solvates of the N-oxides and salts thereof.

In the context of the present invention, preference is also given to compounds of the formula (I-A)

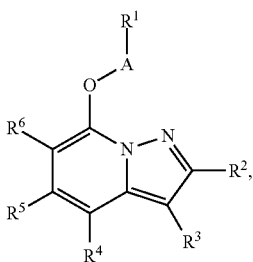

(I-A)

and the N-oxides, salts, solvates, salts of the N-oxides and solvates of the N-oxides and salts thereof.

In the context of the present invention, preference is also given to compounds of the formula (I-B)

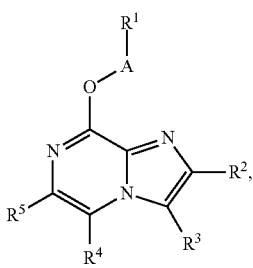

(I-B)

and the N-oxides, salts, solvates, salts of the N-oxides and solvates of the N-oxides and salts thereof.

In the context of the present invention, preference is also given to compounds of the formula (I-A) in which $R^1$ represents a phenyl group of the formula

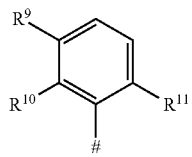

where
* represents the point of attachment to A,
and
$R^9$ represents hydrogen or fluorine,
$R^{10}$ represents fluorine,
$R^{11}$ represents fluorine,
and the N-oxides, salts, solvates, salts of the N-oxides and solvates of the N-oxides and salts thereof.

In the context of the present invention, preference is also given to compounds of the formula (I-A) in which
$R^2$ represents methyl,
and the N-oxides, salts, solvates, salts of the N-oxides and solvates of the N-oxides and salts thereof.

In the context of the present invention, preference is also given to compounds of the formula (I-A) in which
$R^3$ represents phenyl, 3-pyridyl, 4-pyridyl or 4-pyrazolyl,
    where phenyl in the 3-position may be substituted by $(C_1-C_6)$-alkyl, hydroxycarbonyl, —(C═O)NR$^7$R$^8$, methylsulphonyl, ethylsulphonyl, amino and pyrrolidinyl,
        in which amino may be substituted by 1 or 2 substituents independently of one another selected from $(C_1-C_6)$-alkyl, methylcarbonyl and methylsulphonyl,
            in which $(C_1-C_6)$-alkyl may be substituted by 1 or 2 substituents selected from the group consisting of fluorine, pyrrolidinyl and amino,
                in which amino may be substituted by 1 or 2 substituents independently of one another selected from $(C_1-C_4)$-alkyl, methylcarbonyl and methylsulphonyl,
        and in which
            $R^7$ and $R^8$ each independently of one another represent hydrogen or cyclopropyl,
    where 3-pyridyl and 4-pyridyl may each be substituted by 1 or 2 substituents independently of one another selected from the group consisting of fluorine, chlorine, $(C_1-C_6)$-alkyl, amino, hydroxycarbonyl, —(C═O)NR$^7$R$^8$ and piperazinyl,
        in which amino may be substituted by 1 or 2 $(C_1-C_6)$-alkyl substituents,
        in which $(C_1-C_6)$-alkyl may be substituted by amino,
        and in which
            $R^7$ and $R^8$ each represent hydrogen,
    where 4-pyrazolyl may be substituted at the 1-position by $(C_1-C_6)$-alkyl or phenyl,
        in which $(C_1-C_6)$-alkyl may be substituted by 1 to 3 substituents selected from the group consisting of hydroxy, amino, methoxycarbonyl, hydroxycarbonyl, —(C═O)NR$^7$R$^8$, phenyl, pyrazolyl, $(C_3-C_7)$-cycloalkyl and morpholinyl,
            in which pyrazolyl may be substituted by 1 or 3 methyl substituents, in which
R$^7$ represents hydrogen,
R$^8$ represents cyclopropyl,
in which phenyl and pyridyl may be substituted by 1 or 2 fluorine substituents,
and the N-oxides, salts, solvates, salts of the N-oxides and solvates of the N-oxides and salts thereof.

In the context of the present invention, preference is also given to compounds of the formula (I-A) in which
R$^3$ represents phenyl,
where phenyl in the 3-position may be substituted by (C$_1$-C$_6$)-alkyl, hydroxycarbonyl, —(C═O)NR$^7$R$^8$, methylsulphonyl, ethylsulphonyl, amino and pyrrolidinyl,
in which amino may be substituted by 1 or 2 substituents independently of one another selected from (C$_1$-C$_6$)-alkyl, methylcarbonyl and methylsulphonyl,
in which (C$_1$-C$_6$)-alkyl may be substituted by 1 or 2 substituents selected from the group consisting of fluorine, pyrrolidinyl and amino,
in which amino may be substituted by 1 or 2 substituents independently of one another selected from (C$_1$-C$_4$)-alkyl, methylcarbonyl and methylsulphonyl,
and in which
R$^7$ and R$^8$ each independently of one another represent hydrogen or cyclopropyl,
and the N-oxides, salts, solvates, salts of the N-oxides and solvates of the N-oxides and salts thereof.

In the context of the present invention, preference is also given to compounds of the formula (I-A) in which
R$^3$ represents 3-pyridyl or 4-pyridyl,
where 3-pyridyl and 4-pyridyl may each be substituted by 1 or 2 substituents independently of one another selected from the group consisting of fluorine, chlorine, (C$_1$-C$_6$)-alkyl, amino, hydroxycarbonyl, —(C═O)NR$^7$R$^8$ and piperazinyl,
in which amino may be substituted by 1 or 2 (C$_1$-C$_6$)-alkyl substituents,
in which (C$_1$-C$_6$)-alkyl may be substituted by amino,
and in which
R$^7$ and R$^8$ each represent hydrogen,
and the N-oxides, salts, solvates, salts of the N-oxides and solvates of the N-oxides and salts thereof.

In the context of the present invention, particular preference is also given to compounds of the formula (I-A) in which
R$^3$ represents 3-pyridyl,
where 3-pyridyl may be substituted by 1 or 2 substituents independently of one another selected from the group consisting of chlorine, methyl, hydroxycarbonyl and —(C═O)NR$^7$R$^8$,
in which
R$^7$ and R$^8$ each represent hydrogen,
and the N-oxides, salts, solvates, salts of the N-oxides and solvates of the N-oxides and salts thereof.

In the context of the present invention, particular preference is also given to compounds of the formula (I-A) in which
R$^3$ represents 4-pyridyl,
where 4-pyridyl may be substituted by 1 or 2 substituents independently of one another selected from the group consisting of fluorine, amino and piperazinyl,
in which amino may be substituted by 1 or 2 (C$_1$-C$_6$)-alkyl substituents,
in which (C$_1$-C$_6$)-alkyl may be substituted by amino,
and the N-oxides, salts, solvates, salts of the N-oxides and solvates of the N-oxides and salts thereof.

In the context of the present invention, preference is also given to compounds of the formula (I-A) in which
R$^3$ represents 4-pyrazolyl,
where 4-pyrazolyl may be substituted at the 1-position by (C$_1$-C$_6$)-alkyl or phenyl,
in which (C$_1$-C$_6$)-alkyl may be substituted by 1 to 3 substituents selected from the group consisting of hydroxy, amino, methoxycarbonyl, hydroxycarbonyl, —(C═O)NR$^7$R$^8$, phenyl, pyrazolyl, (C$_3$-C$_7$)-cycloalkyl and morpholinyl,
in which pyrazolyl may be substituted by 1 to 3 methyl substituents,
in which
R$^7$ represents hydrogen,
R$^8$ is cyclopropyl,
in which phenyl and pyridyl may be substituted by 1 or 2 fluorine substituents,
and the N-oxides, salts, solvates, salts of the N-oxides and solvates of the N-oxides and salts thereof.

In the context of the present invention, particular preference is also given to compounds of the formula (I-A) in which
R$^3$ represents 4-pyrazolyl,
where 4-pyrazolyl may be substituted at the 1-position by (C$_1$-C$_6$)-alkyl or phenyl,
in which (C$_1$-C$_6$)-alkyl may be substituted by hydroxy, amino, methoxycarbonyl, hydroxycarbonyl, —(C═O)NR$^7$R$^8$, phenyl, pyrazolyl, (C$_3$-C$_7$)-cycloalkyl or morpholinyl,
in which pyrazolyl may be substituted by 1 or 2 methyl substituents,
in which
R$^7$ represents hydrogen,
R$^8$ represents cyclopropyl,
in which phenyl may be substituted by fluorine,
and the N-oxides, salts, solvates, salts of the N-oxides and solvates of the N-oxides and salts thereof.

In the context of the present invention, preference is also given to compounds of the formula (I-A) in which
R$^5$ represents hydrogen or methyl,
and the N-oxides, salts, solvates, salts of the N-oxides and solvates of the N-oxides and salts thereof.

In the context of the present invention, particular preference is also given to compounds of the formula (I-A) in which
R$^5$ represents hydrogen,
and the N-oxides, salts, solvates, salts of the N-oxides and solvates of the N-oxides and salts thereof.

In the context of the present invention, particular preference is also given to compounds of the formula (I-A) in which
R$^5$ represents methyl,
and the N-oxides, salts, solvates, salts of the N-oxides and solvates of the N-oxides and salts thereof.

The individual radical definitions specified in the respective combinations or preferred combinations of radicals are, independently of the respective combinations of the radicals specified, also replaced as desired by radical definitions of other combinations.

Particular preference is given to combinations of two or more of the preferred ranges mentioned above.

The invention further provides a process for preparing the compounds of the formula (I-A) according to the invention, characterized in that a compound of the formula (II)

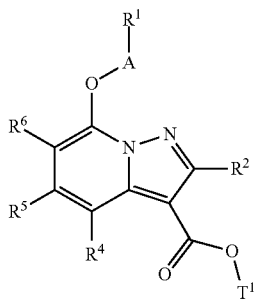
(II)

in which A, R¹, R², R⁴, R⁵ and R⁶ each have the meanings given above and

T¹ represents $(C_1\text{-}C_4)$-alkyl or benzyl, is reacted in an inert solvent in the presence of a suitable base or acid to give a carboxylic acid of the formula (III)

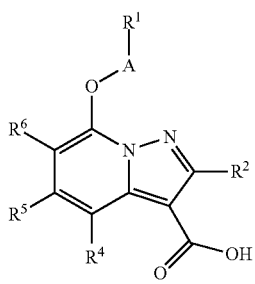
(III)

in which A, R¹, R², R⁴, R⁵ and R⁶ each have the meanings given above, and this is then converted with a halogen equivalent in the presence of a suitable base into a compound of the formula (IV)

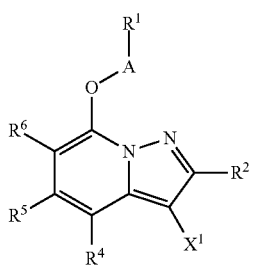
(IV)

in which A, R¹, R², R⁴, R⁵ and R⁶ each have the meanings given above and

X¹ represents chlorine, bromine or iodine, and this is subsequently reacted in an inert solvent, in the presence of a suitable transition metal catalyst, with a compound of the formula (V)

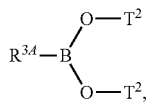
(V)

in which $R^{3A}$ has the meanings given above for R³ and

T² represents hydrogen or $(C_1\text{-}C_4)$-alkyl, or the two T² radicals together form a —C(CH₃)₂—C(CH₃)₂— bridge, to give a compound of the formula (I-A1)

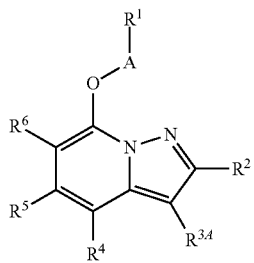
(I-A1)

in which A, R¹, R², R⁴, R⁵ and R⁶ each have the meanings given above, and these compounds are subsequently, if $R^{3A}$ represents

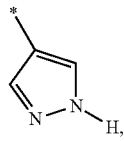
(VI)

reacted in an inert solvent in the presence of a suitable base with a compound of the formula (VII)

$R^{12}\text{—}X^1$ (VII)

in which

X¹ represents a suitable leaving group, in particular chlorine, bromine, iodine, mesylate, triflate or tosylate,
and R¹² represents $(C_1\text{-}C_6)$-alkyl,
in which $(C_1\text{-}C_6)$-alkyl may be substituted by 1 to 3 substituents selected from the group consisting of fluorine, cyano, hydroxy, amino, trifluoromethyl, difluoromethyl, $(C_1\text{-}C_4)$-alkylsulphonyl, $(C_1\text{-}C_4)$-alkylcarbonyl, $(C_1\text{-}C_4)$-alkoxycarbonyl, hydroxycarbonyl, —(C═O)NR⁷R⁸ $(C_1\text{-}C_4)$-alkoxy, phenoxy, phenyl, pyridyl, pyrimidyl, 5-membered heteroaryl, $(C_3\text{-}C_7)$-cycloalkyl, morpholinyl, piperidinyl, pyrrolidinyl, piperazinyl, 1,1-dioxidothiomorpholin-4-yl and azetidine,
in which 5-membered heteroaryl may be substituted by 1 to 3 substituents selected from the group consisting of halogen, $(C_1\text{-}C_4)$-alkyl and $(C_1\text{-}C_4)$-alkoxy,
in which
R⁷ and R⁸ each independently of one another represent hydrogen, $(C_1\text{-}C_4)$-alkyl or $(C_3\text{-}C_7)$-cycloalkyl,
in which piperidinyl may be substituted by 1 to 4 fluorine substituents,
in which phenyl may be substituted by 1 to 3 substituents selected from the group consisting of halogen, $(C_1\text{-}C_4)$-alkyl and $(C_1\text{-}C_4)$-alkoxy, in which azetidine may be substituted by hydroxy,
in which amino may be substituted by 1 or 2 ($C_1$-$C_4$)-alkyl substituents,
and
in which piperazinyl may be substituted by 1 to 3 substituents independently of one another selected from the group consisting of ($C_1$-$C_4$)-alkyl, ($C_3$-$C_7$)-cycloalkyl and trifluoromethyl,
to give a compound of the formula (I-A2)

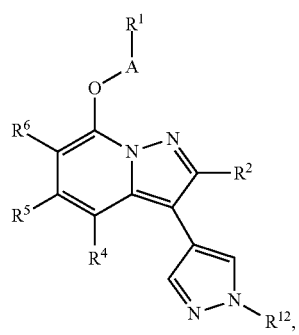

(I-A2)

in which A, $R^1$, $R^2$, $R^4$, $R^5$, $R^6$ and $R^{12}$ each have the meanings given above and
then any protective groups present are detached, and the resulting compounds of the formula (I-A) are optionally converted with the appropriate (i) solvents and/or (ii) acids or bases to the solvates, salts and/or solvates of the salts thereof.

The preparation process described can be illustrated by way of example by the following synthesis scheme (Scheme 1):

Scheme 1:

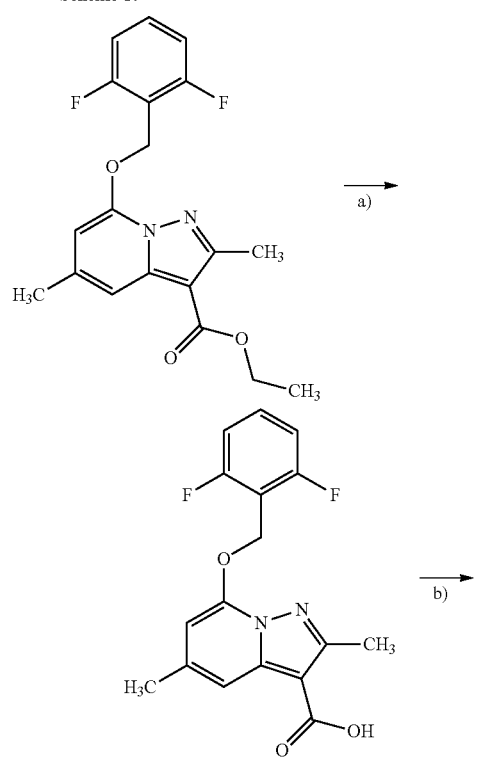

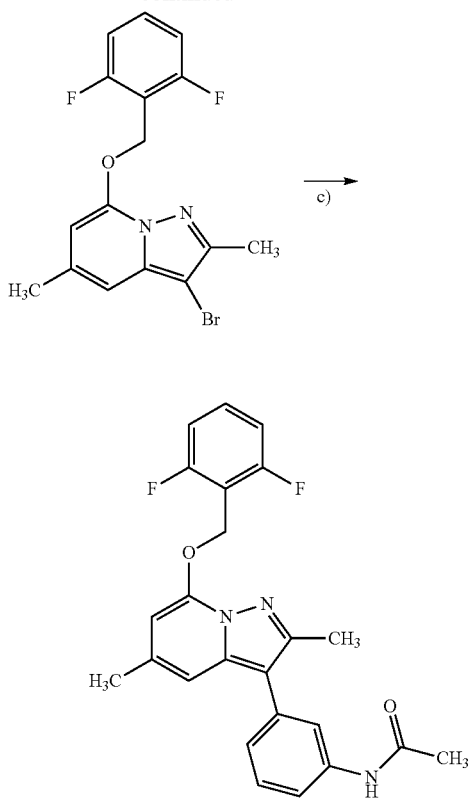

[a]: sodium hydroxide, 1,4-dioxane, 90° C.; b): N-bromosuccinimide, DMF, sodium bicarbonate, room temperature; c): (3-acetamidophenyl)boric acid, chloro(2-dicyclohexylphosphino-2',4',6'-triisopropyl-1,1'-biphenyl) [2-(2'-amino-1,1'-biphenyl)palladium (II) [CAS: 1310584-14-5], $K_3PO_4$, acetonitrile, 60° C. or 100° C.].

The invention further provides a process for preparing the compounds of the formula (I-B) according to the invention, characterized in that
a compound of the formula (VIII)

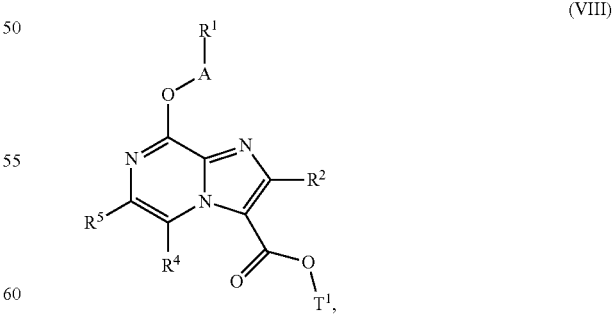

(VIII)

in which A, $R^1$, $R^2$, $R^4$ and $R^5$ are each as defined above and
$T^1$ represents ($C_1$-$C_4$)-alkyl or benzyl,
is reacted in an inert solvent in the presence of a suitable base or acid to give a carboxylic acid of the formula (IX)

(IX)

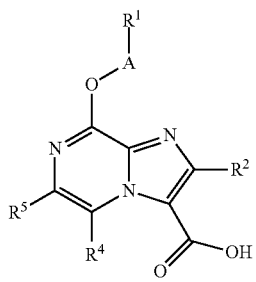

in which A, $R^1$, $R^2$, $R^4$ and $R^5$ each have the meanings given above,
and this is then converted with a halogen equivalent in the presence of a base into a compound of the formula (X)

(X)

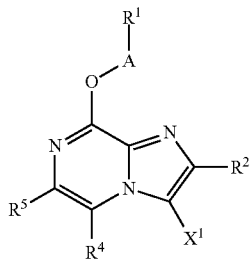

in which A, $R^1$, $R^2$, $R^4$ and $R^5$ each have the meanings given above and
$X^1$ represents chlorine, bromine or iodine,
and this is subsequently reacted in an inert solvent, in the presence of a suitable transition metal catalyst, with a compound of the formula (V), (V)

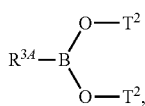

in which
$R^{3A}$ has the meanings given above for $R^3$ and
$T^2$ represents hydrogen or $(C_1$-$C_4)$-alkyl, or the two $T^2$ radicals together form a —$C(CH_3)_2$—$C(CH_3)_2$— bridge, then any protective groups present are detached, and the resulting compounds of the formula (I-B) are optionally converted with the appropriate (i) solvents and/or (ii) acids or bases to the solvates, salts and/or solvates of the salts thereof.

The compounds of the formulae (V) and (VII) are commercially available, known from the literature or can be prepared in analogy to literature processes.

The hydrolysis of the ester group $T^1$ in the compounds of the formula (II) or (III) is carried out by customary methods, by treating the esters in inert solvents with acids or bases, in which latter case the salts formed at first are converted to the free carboxylic acids by treating with acid. In the case of the tert-butyl esters, the ester hydrolysis is preferably carried out with acids. In the case of the benzyl esters, the ester cleavage is preferably carried out by hydrogenolysis with palladium on activated carbon or Raney nickel. Suitable inert solvents for this reaction are water or the organic solvents customary for ester hydrolysis. These preferably include alcohols such as methanol, ethanol, n-propanol, isopropanol, n-butanol or tert-butanol, or ethers such as diethyl ether, tetrahydrofuran, 2-methyltetrahydrofuran, dioxane or glycol dimethyl ether, or other solvents such as acetone, dichloromethane, dimethylformamide or dimethyl sulphoxide. It is also possible to use mixtures of the solvents mentioned. In the case of a basic ester hydrolysis, preference is given to using mixtures of water with dioxane, tetrahydrofuran, methanol and/or ethanol.

Suitable bases for the ester hydrolysis are the customary inorganic bases. These preferably include alkali metal or alkaline earth metal hydroxides, for example sodium hydroxide, lithium hydroxide, potassium hydroxide or barium hydroxide, or alkali metal or alkaline earth metal carbonates, such as sodium carbonate, potassium carbonate or calcium carbonate. Particular preference is given to sodium hydroxide or lithium hydroxide.

Suitable acids for the ester hydrolysis are generally sulfuric acid, hydrogen chloride/hydrochloric acid, hydrogen bromide/hydrobromic acid, phosphoric acid, acetic acid, trifluoroacetic acid, toluenesulfonic acid, methanesulfonic acid or trifluoromethanesulfonic acid, or mixtures thereof, optionally with addition of water. Preference is given to hydrogen chloride or trifluoroacetic acid in the case of the tert-butyl esters and to hydrochloric acid in the case of the methyl esters.

The ester hydrolysis is generally carried out within a temperature range from 0° C. to +100° C., preferably at +0° C. to +50° C.

These conversions can be performed at atmospheric, elevated or reduced pressure (for example from 0.5 to 5 bar). In general, the reaction is in each case carried out at atmospheric pressure.

Suitable solvents for process step (III)→(IV) or (IX)→(X) include alcohols such as methanol, ethanol, n-propanol, isopropanol, n-butanol or tert-butanol, or ethers such as diethyl ether, tetrahydrofuran, 2-methyltetrahydrofuran, dioxane or glycol dimethyl ether, or other solvents such as acetone, acetonitrile, N-methylpyrrolidine (NMP), dichloromethane, dimethylformamide or dimethyl sulphoxide. It is also possible to use mixtures of the solvents mentioned. Preference is given to using dimethylformamide or methylpyrrolidine.

The conversion (III)→(IV) or (IX)→(X) is optionally carried out in the presence of a suitable base. Suitable bases for this conversion are the customary inorganic or organic bases. These preferably include alkali metal hydroxides, for example lithium hydroxide, sodium hydroxide or potassium hydroxide, alkali metal or alkaline earth metal carbonates such as lithium carbonate, sodium carbonate, potassium carbonate, calcium carbonate or caesium carbonate, sodium bicarbonate, potassium bicarbonate, alkali metal alkoxides such as sodium methoxide or potassium methoxide or sodium tert-butoxide or potassium tert-butoxide, amides such as sodium amide, lithium bis(trimethylsilyl)amide, sodium bis(trimethylsilyl)amide or potassium bis(trimethylsilyl)amide or lithium diisopropylamide, or organic amines such as triethylamine, N-methylmorpholine, N-methylpiperidine, N,N-diisopropylethylamine, pyridine, 1,5-diazabicyclo[4.3.0]non-5-ene (DBN), 1,8-diazabicyclo[5.4.0]undec-7-ene (DBU) or 1,4-diazabicyclo[2.2.2]octane (DABCO®) or potassium phosphate. Preference is given to using sodium bicarbonate or potassium bicarbonate.

A suitable halogen source for the reaction (III)→(IV) or (IX)→(X) is, for example, N-bromosuccinimide, N-chlorosuccinimide, N-iodosuccinimide, chlorine, bromine or iodine. Preference is given to using N-bromosuccinimide.

The reaction (III)→(IV) or (IX)→(X) is generally carried out in a temperature range of from −20° C. to +100° C., preferably in the range from +0° C. to +50° C. The reaction can be performed at atmospheric, elevated or reduced pressure (for example in the range from 0.5 to 5 bar). In general, the reaction is carried out at atmospheric pressure.

The process step (IV)+(V)→(I-A1) or (X)+(V)→(1-B) is carried out in a solvent which is inert under the reaction conditions. Suitable solvents are, for example, alcohols such as methanol, ethanol, n-propanol, isopropanol, n-butanol or tert-butanol, ethers such as diethyl ether, dioxane, tetrahydrofuran, glycol dimethyl ether or diethylene glycol dimethyl ether, or other solvents such as 1,2-dimethoxyethane (DME), dimethylformamide (DMF), dimethyl sulphoxide (DMSO), N,N'-dimethylpropyleneurea (DMPU), N-methylpyrrolidone (NMP), pyridine, acetonitrile, toluene or else water. It is also possible to use mixtures of the solvents mentioned. Preference is given to acetonitrile and water.

The conversion (IV)+(V)→(I-A1) or (X)+(V)→(1-B) can optionally be carried out in the presence of a suitable palladium and/or copper catalyst. A suitable palladium catalyst is, for example, palladium(II) acetate, tetrakis(triphenylphosphine)palladium(0), bis(tri-tert-butylphosphine)palladium(0), bis(triphenylphosphine)palladium(II) chloride, bis(acetonitrile)palladium(II) chloride and [1,1'-bis(diphenylphosphino)ferrocene]dichloropalladium(II) and the corresponding dichloromethane complex, optionally in conjunction with additional phosphane ligands, for example (2-biphenyl)di-tert-butylphosphine, 2-dicyclohexylphosphino-2',6'-dimethoxybiphenyl (SPHOS), dicyclohexyl[2',4',6'-tris(1-methylethyl)biphenyl-2-yl]phosphane (XPHOS), bis(2-phenylphosphinophenyl) ether (DPEphos), 4,5-bis(diphenylphosphino)-9,9-dimethylxanthene (Xantphos) [cf., for example, Hassan J. et al., *Chem. Rev.* 102, 1359-1469 (2002)] or chloro(2-dicyclohexylphosphino-2',4',6'-triisopropyl-1,1'-biphenyl)[2-(2'-amino-1,1'-biphenyl)palladium (II) [CAS: 1310584-14-5].

The conversion (IV)+(V)→(I-A1) or (X)+(V)→(1-B) is optionally carried out in the presence of a suitable base. Suitable bases for this conversion are the customary inorganic or organic bases. These preferably include alkali metal hydroxides, for example lithium hydroxide, sodium hydroxide or potassium hydroxide, alkali metal or alkaline earth metal carbonates such as lithium carbonate, sodium carbonate, potassium carbonate, calcium carbonate or caesium carbonate, alkali metal alkoxides such as sodium methoxide or potassium methoxide, sodium ethoxide or potassium ethoxide or sodium or potassium tert-butoxide, alkali metal hydrides such as sodium hydride or potassium hydride, amides such as sodium amide, lithium bis(trimethylsilyl)amide, sodium bis(trimethylsilyl)amide or potassium bis(trimethylsilyl)amide or lithium diisopropylamide, or organic amines such as triethylamine, N-methylmorpholine, N-methylpiperidine, N,N-diisopropylethylamine, pyridine, 1,5-diazabicyclo[4.3.0]non-5-ene (DBN), 1,8-diazabicyclo[5.4.0]undec-7-ene (DBU) or 1,4-diazabicyclo[2.2.2]octane (DABCO®) or potassium phosphate. Preference is given to using potassium phosphate.

The reaction (IV)+(V)→(I-A1) or (X)+(V)→(1-B) is generally carried out in a temperature range from 0° C. to +200° C., preferably at from +60° C. to +120° C. The conversion can be carried out under atmospheric, elevated or reduced pressure (for example from 0.5 to 5 bar). In general, the reaction is carried out at atmospheric pressure.

Inert solvents for the process step (I-A1)+(VII)→(I-A2) are, for example, halohydrocarbons such as dichloromethane, trichloromethane, tetrachloromethane, trichloroethylene or chlorobenzene, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, or other solvents such as acetone, methyl ethyl ketone, ethyl acetate, acetonitrile, N,N-dimethylformamide, N,N-dimethylacetamide, dimethyl sulphoxide, N,N'-dimethylpropyleneurea (DMPU), N-methylpyrrolidone (NMP) or pyridine. It is also possible to use mixtures of the solvents mentioned. Preference is given to using dimethylformamide or dimethyl sulphoxide.

Suitable bases for the process step (I-A1)+(VII)→(I-A2) are the customary inorganic or organic bases. These preferably include alkali metal hydroxides, for example lithium hydroxide, sodium hydroxide or potassium hydroxide, alkali metal or alkaline earth metal carbonates such as lithium carbonate, sodium carbonate, potassium carbonate, calcium carbonate or caesium carbonate, optionally with addition of an alkali metal iodide, for example sodium iodide or potassium iodide, alkali metal alkoxides such as sodium methoxide or potassium methoxide, sodium ethoxide or potassium ethoxide or sodium or potassium tert-butoxide, alkali metal hydrides such as sodium hydride or potassium hydride, amides such as sodium amide, lithium bis(trimethylsilyl)amide or potassium bis(trimethylsilyl)amide or lithium diisopropylamide, or organic amines such as triethylamine, N-methylmorpholine, N-methylpiperidine, N,N-diisopropylethylamine, pyridine, 4-(N,N-dimethylamino)pyridine (DMAP), 1,5-diazabicyclo[4.3.0]non-5-ene (DBN), 1,8-diazabicyclo[5.4.0]undec-7-ene (DBU) or 1,4-diazabicyclo[2.2.2]octane (DABCO®). Preference is given to using potassium carbonate, caesium carbonate or sodium methoxide.

The reaction is generally carried out within a temperature range from 0° C. to +120° C., preferably at +20° C. to +80° C., optionally in a microwave. The reaction can be carried out under atmospheric, elevated or reduced pressure (for example from 0.5 to 5 bar).

The amino protecting group used is preferably tert-butoxycarbonyl (Boc) or benzyloxycarbonyl (Z). The protecting group used for a hydroxy or carboxyl function is preferably tert-butyl or benzyl. These protective groups are detached by customary methods, preferably by reaction with a strong acid such as hydrogen chloride, hydrogen bromide or trifluoroacetic acid in an inert solvent such as dioxane, diethyl ether, dichloromethane or acetic acid; it is optionally also possible to effect the detachment without an additional inert solvent. In the case of benzyl and benzyloxycarbonyl as protective groups, these may also be removed by hydrogenolysis in the presence of a palladium catalyst. The detachment of the protective groups mentioned can optionally be undertaken simultaneously in a one-pot reaction or in separate reaction steps.

The compounds of the formula (III) are known from the literature or can be prepared by

[A] converting a compound of the formula (XI)

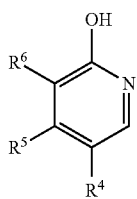
(XI)

in which $R^4$, $R^5$ and $R^6$ have the meaning given above,
in an inert solvent in the presence of a suitable base with a compound of the formula (XII)

(XII)

in which A and $R^1$ each have the meaning given above and
$X^1$ represents a suitable leaving group, in particular chlorine, bromine, iodine, mesylate, triflate or tosylate,
into a compound of the formula (XIII)

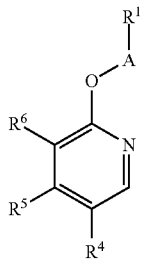
(XIII)

in which A, $R^1$, $R^4$, $R^5$ and $R^6$ each have the meanings given above,
then converting this with O-(2-mesitylenesulphonyl)hydroxylamine (MSH) into a compound (XIV)

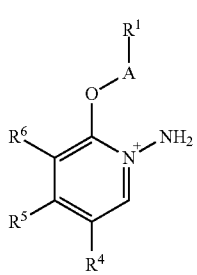
(XIV)

and then reacting this in an inert solvent with a compound of the formula (XV)

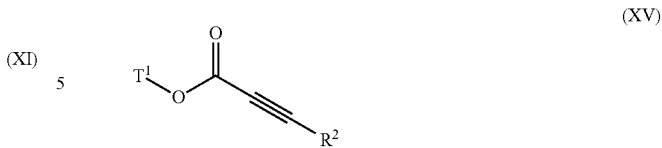
(XV)

in which $R^2$ and $T^1$ each have the meanings given above.
or
[B] converting a compound of the formula (XVI)

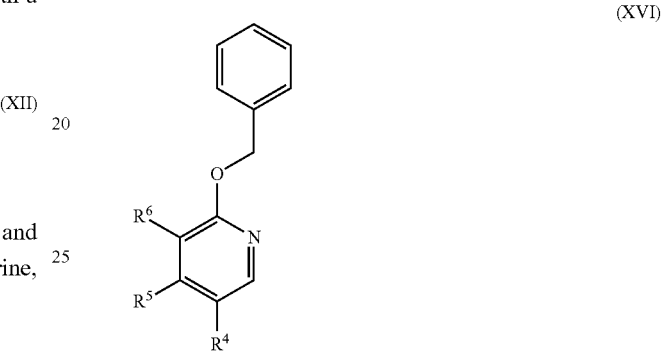
(XVI)

in which $R^4$, $R^5$ and $R^6$ each have the meaning given above with O-(2-mesitylenesulphonyl)hydroxylamine (MSH) into a compound (XVII)

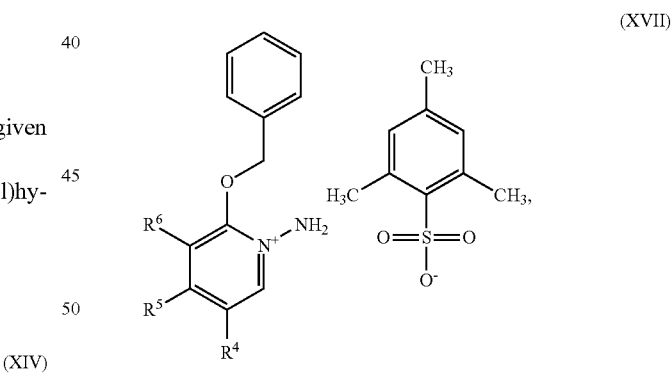
(XVII)

then reacting this in an inert solvent with a compound of the formula (IX)

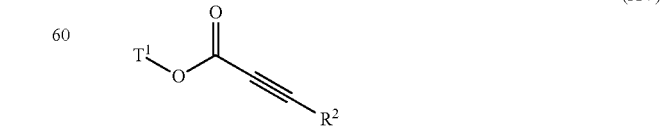
(XV)

in which $R^2$ and $T^1$ each have the meanings given above, into a compound (XVIII)

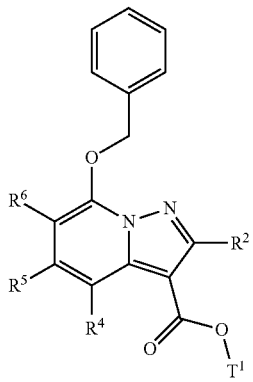

(XVIII)

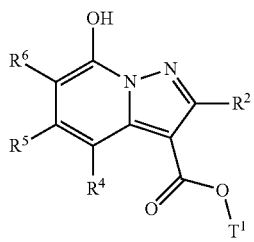

(XIX)

in which $R^2$, $R^4$, $R^5$ and $R^6$ each have the meanings given above and $T^1$ represents $(C_1$-$C_4)$-alkyl or benzyl, in an inert solvent under Mitsunobu conditions with a compound of the formula (XX)

$$R^1\text{—}A\diagdown_{OH,}$$

(XX)

in which A and $R^1$ each have the meaning given above.

in which $R^2$, $R^4$, $R^5$ and $R^6$ each have the meanings given above and $T^1$ represents $(C_1$-$C_4)$-alkyl or benzyl, subsequently detaching the benzyl group therefrom by the methods known to those skilled in the art and reacting the resulting compound (XIX)

The processes described are illustrated by way of example by the schemes below (Schemes 2 to 3):

Scheme 2:

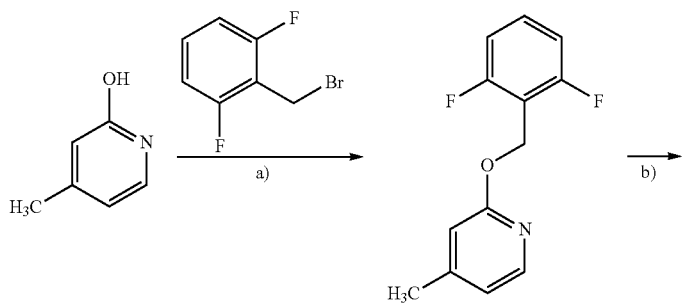

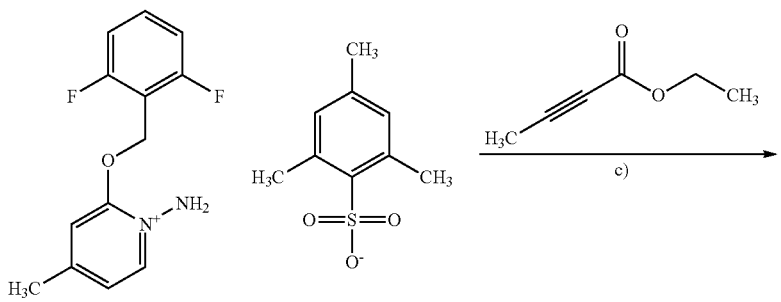

-continued

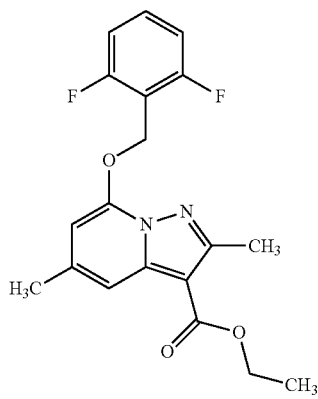

[(a) Ag₂CO₃, THF, reflux; (b) O-(2-mesitylenesulphonyl)hydroxylamine (MSH), dichloromethane, room temperature; (c) K₂CO₃, DMF, room temperature].

Scheme 3:

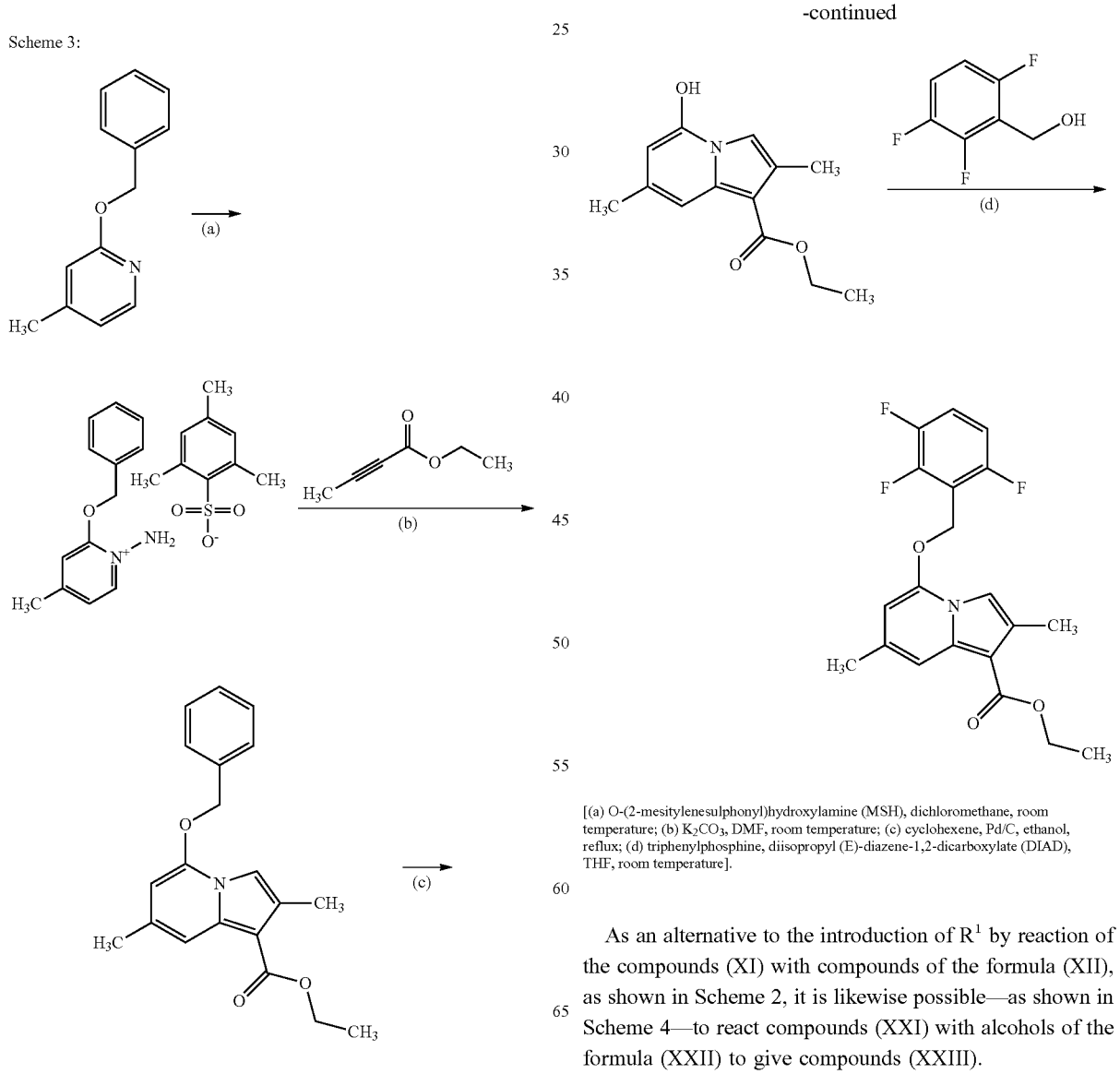

[(a) O-(2-mesitylenesulphonyl)hydroxylamine (MSH), dichloromethane, room temperature; (b) K₂CO₃, DMF, room temperature; (c) cyclohexene, Pd/C, ethanol, reflux; (d) triphenylphosphine, diisopropyl (E)-diazene-1,2-dicarboxylate (DIAD), THF, room temperature].

As an alternative to the introduction of $R^1$ by reaction of the compounds (XI) with compounds of the formula (XII), as shown in Scheme 2, it is likewise possible—as shown in Scheme 4—to react compounds (XXI) with alcohols of the formula (XXII) to give compounds (XXIII).

Scheme 4:

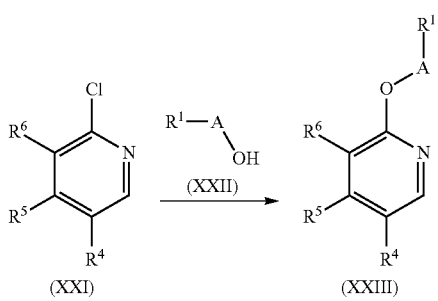

Typical reaction conditions for such reactions can be found in the specialist literature, for example Poon, K. W. C. Synlet 2005, 6, 841. Typically, conversion is effected in the presence of a base such as potassium hydroxide and sodium hydroxide, optionally with addition of an 18-crown-6 ether, in an inert solvent, for example THF or toluene, at a temperature between 0° C. and the boiling point of the solvent used.

Inert solvents for the process step (XI)+(XII)→(XIII) are, for example, ethers such as diethyl ether, dioxane, tetrahydrofuran, dimethoxymethane, glycol dimethyl ether or diethylene glycol dimethyl ether, or other solvents such as acetone, methyl ethyl ketone, ethyl acetate, acetonitrile, N,N-dimethylformamide, N,N-dimethylacetamide, dimethyl sulphoxide, N,N'-dimethylpropyleneurea (DMPU), N-methylpyrrolidone (NMP). It is also possible to use mixtures of the solvents mentioned. Preference is given to using dimethoxyethane or tetrahydrofuran.

Suitable bases for the process step (XI)+(XII)→(XIII) are the customary inorganic or organic bases. These preferably include alkali metal hydroxides, for example lithium hydroxide, sodium hydroxide or potassium hydroxide, carbonates such as lithium carbonate, sodium carbonate, potassium carbonate, calcium carbonate, silver carbonate or caesium carbonate, optionally with addition of an alkali metal iodide, for example sodium iodide or potassium iodide, alkali metal alkoxides such as sodium methoxide or potassium methoxide, sodium ethoxide or potassium ethoxide or sodium or potassium tert-butoxide, alkali metal hydrides such as sodium hydride or potassium hydride, amides such as sodium amide, lithium bis(trimethylsilyl)amide or potassium bis(trimethylsilyl)amide or lithium diisopropylamide, or organic amines such as triethylamine, N-methylmorpholine, N-methylpiperidine, N,N-diisopropylethylamine, pyridine, 4-(N,N-dimethylamino)pyridine (DMAP), 1,5-diazabicyclo[4.3.0]non-5-ene (DBN), 1,8-diazabicyclo[5.4.0]undec-7-ene (DBU) or 1,4-diazabicyclo[2.2.2]octane (DABCO®). Preference is given to using sodium tert-butoxide, potassium tert-butoxide, silver carbonate or caesium carbonate.

The reaction is generally carried out within a temperature range from 0° C. to +120° C., preferably at +20° C. to +80° C., optionally in a microwave. The reaction can be carried out under atmospheric, elevated or reduced pressure (for example from 0.5 to 5 bar).

Inert solvents for the process step (XIII)→(XIV) or (XVI)→(XVII) are, for example, dichloromethane, 1,2-dichloroethane, or other solvents such as acetone, methyl ethyl ketone, ethyl acetate, acetonitrile, N,N-dimethylformamide, N,N-dimethylacetamide, dimethyl sulphoxide, N,N'-dimethylpropyleneurea (DMPU), N-methylpyrrolidone (NMP). It is also possible to use mixtures of the solvents mentioned. Preference is given to using dichloromethane.

The reaction is generally carried out in a temperature range of from 0° C. to +120° C., preferably at +20° C. to +80° C. The reaction can be performed at atmospheric, elevated or reduced pressure (for example from 0.5 to 5 bar).

Inert solvents for the ring closure to give the pyrazolo[1,5-a]pyridine skeleton (XIV)+(XV)→(II) or (XVII)+(XV)→(XVIII) are the customary organic solvents. These preferably include alcohols such as methanol, ethanol, n-propanol, isopropanol, n-butanol, n-pentanol or tert-butanol, or ethers such as diethyl ether, tetrahydrofuran, 2-methyltetrahydrofuran, dioxane or glycol dimethyl ether, or other solvents such as acetone, dichloromethane, 1,2-dichloroethane, acetonitrile, dimethylformamide or dimethyl sulphoxide. It is also possible to use mixtures of the solvents mentioned. Preference is given to using ethanol.

The ring closure is generally carried out within a temperature range from +20° C. to +150° C., preferably at +20° C. to +100° C., optionally in a microwave.

The ring closure (XIV)+(XV)→(II) is optionally carried out in the presence of dehydrating reaction additives, for example in the presence of molecular sieve (pore size 3 Å or 4 Å) or using a water separator. The reaction (XIV)+(XV)→(II) is carried out using an excess of the reagent of the formula (XV), for example with 1 to 20 equivalents of the reagent (XV), optionally with addition of bases (for example sodium bicarbonate), in which case the addition of this reagent can take place all at once or in several portions.

The removal of the benzyl group in the reaction step (XVIII)→(XIX) is carried out here by customary methods known from protecting group chemistry, preferably by hydrogenolysis in the presence of a palladium catalyst, for example palladium on activated carbon, in an inert solvent, for example ethanol or ethyl acetate [see also, for example, T. W. Greene and P. G. M. Wuts, *Protective Groups in Organic Synthesis*, Wiley, New York, 1999].

The Mitsunobu condensation (XIX)+(XX)→(II) is carried out in the presence of an activating reagent, for example diethyl (E)-diazene-1,2-dicarboxylate (DEAD) or diisopropyl (E)-diazene-1,2-dicarboxylate (DIAD), and of a phosphine reagent, e.g. triphenylphosphine or tributylphosphine, in an inert solvent, e.g. THF, dichloromethane, toluene or DMF, at a temperature between 0° C. and the boiling point of the solvent used.

The compounds of the formula (VIII) are known from the literature or can be prepared by
[C] converting a compound of the formula (XXIV)

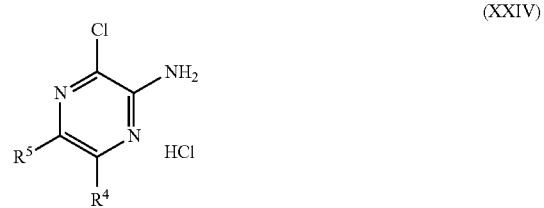

in which $R^4$ and $R^5$ each have the meaning given above in an inert solvent in the presence of a suitable base with a compound of the formula (XXV)

in which A and $R^1$ each have the meaning given above and $X^1$ represents hydroxy,
to give a compound of the formula (XXVI)

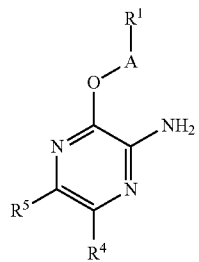

(XXVI)

in which A, $R^1$, $R^4$ and $R^5$ each have the meanings given above,
and then reacting this in an inert solvent with a compound of the formula (XXVII)

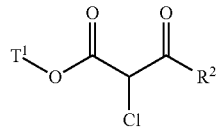

(XXVII)

in which $R^2$ and $T^1$ each have the meanings given above.

The process described is illustrated in an exemplary manner by the scheme below (Scheme 5):

Scheme 5:

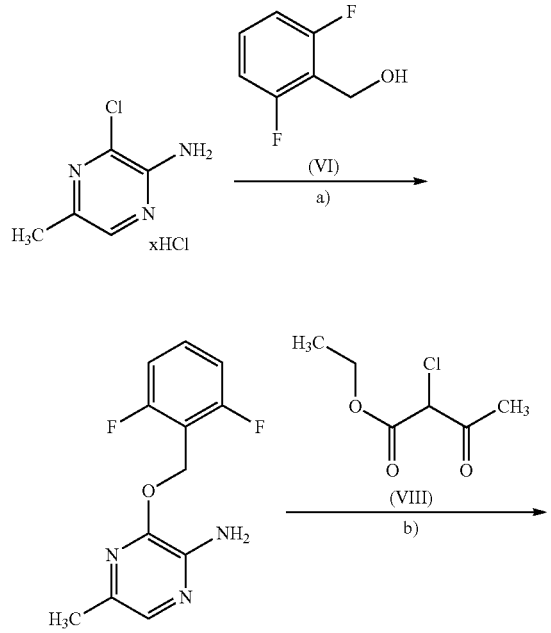

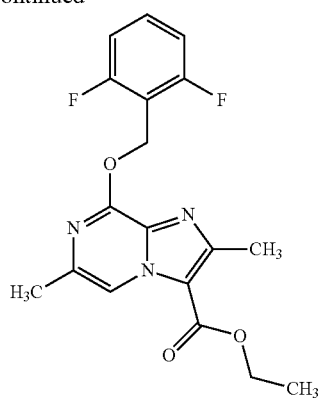

[(a) potassium tert-butoxide, 1,2-dimethoxyethane, 80° C.; (b) ethanol, molecular sieve, reflux].

The synthesis sequence shown can be modified such that the respective reaction steps are carried out in a different order. An example of such a modified synthesis sequence is shown in Scheme 6.

Scheme 6:

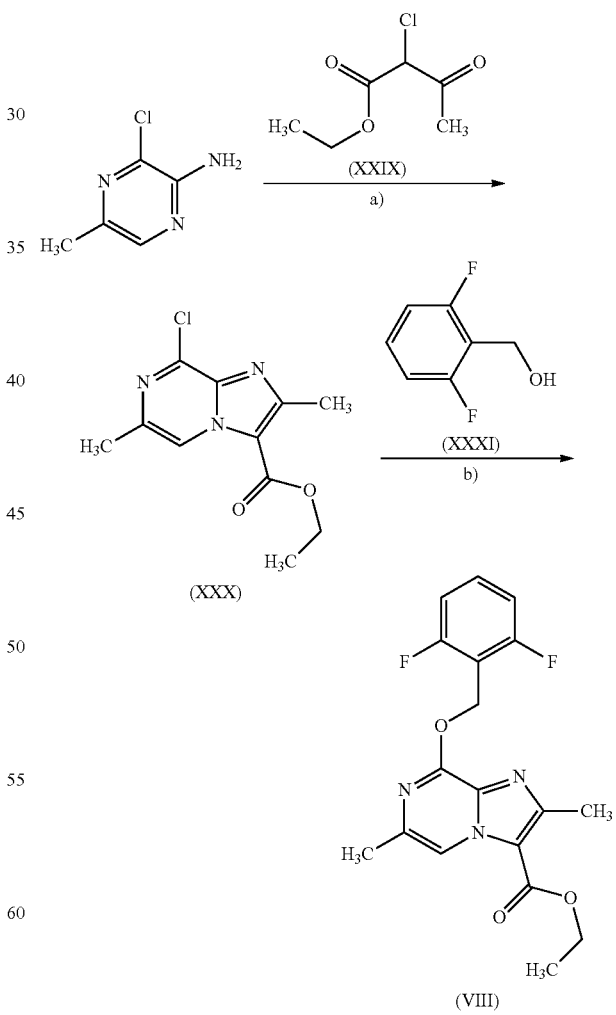

[a): EtOH, molecular sieve, reflux; b): potassium tert-butoxide, 1,2-dimethoxyethane, 80° C.].

Inert solvents for the process step (XXIV)+(XXV)→(XXVI) or (XXX)+(XXXI)→(VIII) are, for example, ethers such as diethyl ether, dioxane, tetrahydrofuran, dimethoxymethane, glycol dimethyl ether or diethylene glycol dimethyl ether, or other solvents such as acetone, methyl ethyl ketone, ethyl acetate, acetonitrile, N,N-dimethylformamide, N,N-dimethylacetamide, dimethyl sulphoxide, N,N'-dimethylpropyleneurea (DMPU), N-methylpyrrolidone (NMP). It is also possible to use mixtures of the solvents mentioned. Preference is given to using dimethoxyethane.

Suitable bases for the process step (XXIV)+(XXV)→(XXVI) or (XXX)+(XXXI)→(VIII) are the customary inorganic or organic bases. These preferably include alkali metal hydroxides, for example lithium hydroxide, sodium hydroxide or potassium hydroxide, alkali metal or alkaline earth metal carbonates such as lithium carbonate, sodium carbonate, potassium carbonate, calcium carbonate or caesium carbonate, optionally with addition of an alkali metal iodide, for example sodium iodide or potassium iodide, alkali metal alkoxides such as sodium methoxide or potassium methoxide, sodium ethoxide or potassium ethoxide or sodium or potassium tert-butoxide, alkali metal hydrides such as sodium hydride or potassium hydride, amides such as sodium amide, lithium bis(trimethylsilyl)amide or potassium bis(trimethylsilyl)amide or lithium diisopropylamide, or organic amines such as triethylamine, N-methylmorpholine, N-methylpiperidine, N,N-diisopropylethylamine, pyridine, 4-(N,N-dimethylamino)pyridine (DMAP), 1,5-diazabicyclo[4.3.0]non-5-ene (DBN), 1,8-diazabicyclo[5.4.0]undec-7-ene (DBU) or 1,4-diazabicyclo[2.2.2]octane (DABCO®). Preference is given to using sodium tert-butoxide or potassium tert-butoxide.

The reaction is generally carried out within a temperature range from 0° C. to +120° C., preferably at +20° C. to +80° C., optionally in a microwave. The reaction can be carried out under atmospheric, elevated or reduced pressure (for example from 0.5 to 5 bar).

Inert solvents for the ring closure to give the imidazo[1,2-a]pyrazine skeleton (XXVI)+(XXVII)→(VIII) or (XXVIII)+(XXIX)→(XXX) are the customary organic solvents. These preferably include alcohols such as methanol, ethanol, n-propanol, isopropanol, n-butanol, n-pentanol or tert-butanol, or ethers such as diethyl ether, tetrahydrofuran, 2-methyltetrahydrofuran, dioxane or glycol dimethyl ether, or other solvents such as acetone, dichloromethane, 1,2-dichloroethane, acetonitrile, dimethylformamide or dimethyl sulphoxide. It is also possible to use mixtures of the solvents mentioned. Preference is given to using ethanol or dimethylformamide.

The ring closure is generally carried out within a temperature range from +50° C. to +150° C., preferably at +50° C. to +100° C., optionally in a microwave.

The ring closure (XXVI)+(XXVII)→(VIII) or (XXVIII)+(XXIX)→(XXX) is optionally effected in the presence of dehydrating reaction additives, for example in the presence of a molecular sieve (pore size 3 Å or 4 Å) or by means of a water separator. The reaction (XVI)+(XVII)→(VIII) or (XXVIII)+(XXIX)→(XXX) is carried out using an excess of the reagent of the formula (XXVII), for example with 1 to 20 equivalents of the reagent (XXVII), optionally with addition of bases (for example sodium bicarbonate), in which case the addition of this reagent can be carried out all at once or in several portions.

Further compounds of the invention can optionally also be prepared by conversions of functional groups of individual substituents, especially those listed for $R^3$, proceeding from the compounds of the formula (I-A) or (I-B) obtained by the above processes. These conversions are performed by customary methods known to those skilled in the art and include, for example, reactions such as nucleophilic and electrophilic substitutions, oxidations, reductions, hydrogenations, transition metal-catalysed coupling reactions, eliminations, alkylation, amination, esterification, ester hydrolysis, etherification, ether hydrolysis, formation of carbonamides, and introduction and removal of temporary protective groups.

The compounds of the invention have valuable pharmacological properties and can be used for prevention and treatment of diseases in humans and animals. The compounds of the invention offer a further treatment alternative and thus enlarge the field of pharmacy.

The compounds of the invention bring about vasorelaxation and inhibition of platelet aggregation, and lead to a decrease in blood pressure and to a rise in coronary blood flow. These effects are mediated by a direct stimulation of soluble guanylate cyclase and an intracellular rise in cGMP. In addition, the compounds of the invention enhance the action of substances which increase the cGMP level, for example EDRF (endothelium-derived relaxing factor), NO donors, protoporphyrin IX, arachidonic acid or phenylhydrazine derivatives.

The compounds of the invention are suitable for the treatment and/or prophylaxis of cardiovascular, pulmonary, thromboembolic and fibrotic disorders.

Accordingly, the compounds according to the invention can be used in medicaments for the treatment and/or prophylaxis of cardiovascular disorders such as, for example, high blood pressure (hypertension), resistant hypertension, acute and chronic heart failure, coronary heart disease, stable and unstable angina pectoris, peripheral and cardiac vascular disorders, arrhythmias, atrial and ventricular arrhythmias and impaired conduction such as, for example, atrioventricular blocks degrees I-III (AB block I-III), supraventricular tachyarrhythmia, atrial fibrillation, atrial flutter, ventricular fibrillation, ventricular flutter, ventricular tachyarrhythmia, Torsade de pointes tachycardia, atrial and ventricular extrasystoles, AV-junctional extrasystoles, sick sinus syndrome, syncopes, AV-nodal re-entry tachycardia, Wolff-Parkinson-White syndrome, of acute coronary syndrome (ACS), autoimmune cardiac disorders (pericarditis, endocarditis, valvolitis, aortitis, cardiomyopathies), shock such as cardiogenic shock, septic shock and anaphylactic shock, aneurysms, boxer cardiomyopathy (premature ventricular contraction (PVC)), for the treatment and/or prophylaxis of thromboembolic disorders and ischaemias such as myocardial ischaemia, myocardial infarction, stroke, cardiac hypertrophy, transient and ischaemic attacks, preeclampsia, inflammatory cardiovascular disorders, spasms of the coronary arteries and peripheral arteries, oedema formation such as, for example, pulmonary oedema, cerebral oedema, renal oedema or oedema caused by heart failure, peripheral circulatory disturbances, reperfusion damage, arterial and venous thromboses, microalbuminuria, myocardial insufficiency, endothelial dysfunction, to prevent restenoses, for example after thrombolysis therapies, percutaneous transluminal angioplasties (PTA), transluminal coronary angioplasties (PTCA), heart transplants and bypass operations, and also micro- and macrovascular damage (vasculitis), increased levels of fibrinogen and of low-density lipoprotein (LDL) and increased concentrations of plasminogen activator inhibitor 1 (PAI-1), and also for the treatment and/or prophylaxis of erectile dysfunction and female sexual dysfunction.

In the context of the present invention, the term "heart failure" encompasses both acute and chronic manifestations of heart failure, and also more specific or related types of disease, such as acute decompensated heart failure, right heart failure, left heart failure, global failure, ischaemic cardiomyopathy, dilated cardiomyopathy, hypertrophic cardiomyopathy, idiopathic cardiomyopathy, congenital heart defects, heart failure associated with heart valve defects, mitral valve stenosis, mitral valve insufficiency, aortic valve stenosis, aortic valve insufficiency, tricuspid valve stenosis, tricuspid valve insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, diastolic heart failure and systolic heart failure and acute phases of worsening of existing chronic heart failure (worsening heart failure).

In addition, the compounds of the invention can also be used for the treatment and/or prophylaxis of arteriosclerosis, impaired lipid metabolism, hypolipoproteinaemias, dyslipidaemias, hypertriglyceridaemias, hyperlipidaemias, hypercholesterolaemias, abetelipoproteinaemia, sitosterolaemia, xanthomatosis, Tangier disease, adiposity, obesity and of combined hyperlipidaemias and metabolic syndrome.

The compounds of the invention can also be used for the treatment and/or prophylaxis of primary and secondary Raynaud's phenomenon, microcirculation impairments, claudication, peripheral and autonomic neuropathies, diabetic microangiopathies, diabetic retinopathy, diabetic ulcers on the extremities, gangrene, CREST syndrome, erythematosis, onychomycosis, rheumatic disorders and for promoting wound healing.

The compounds according to the invention are furthermore suitable for treating urological disorders such as, for example, benign prostate syndrome (BPS), benign prostate hyperplasia (BPH), benign prostate enlargement (BPE), bladder outlet obstruction (BOO), lower urinary tract syndromes (LUTS, including Feline Urological Syndrome (FUS)), disorders of the urogenital system including neurogenic over-active bladder (OAB) and (IC), incontinence (UI) such as, for example, mixed urinary incontinence, urge urinary incontinence, stress urinary incontinence or overflow urinary incontinence (MUI, UUI, SUI, OUI), pelvic pain, benign and malignant disorders of the organs of the male and female urogenital system.

The compounds of the invention are also suitable for the treatment and/or prophylaxis of kidney disorders, in particular of acute and chronic renal insufficiency and acute and chronic renal failure. In the context of the present invention, the term "renal insufficiency" encompasses both acute and chronic manifestations of renal insufficiency, and also underlying or related renal disorders such as renal hypoperfusion, intradialytic hypotension, obstructive uropathy, glomerulopathies, glomerulonephritis, acute glomerulonephritis, glomerulosclerosis, tubulointerstitial diseases, nephropathic disorders such as primary and congenital kidney disease, nephritis, immunological kidney disorders such as kidney transplant rejection and immunocomplex-induced kidney disorders, nephropathy induced by toxic substances, nephropathy induced by contrast agents, diabetic and non-diabetic nephropathy, pyelonephritis, renal cysts, nephrosclerosis, hypertensive nephrosclerosis and nephrotic syndrome which can be characterized diagnostically, for example by abnormally reduced creatinine and/or water excretion, abnormally elevated blood concentrations of urea, nitrogen, potassium and/or creatinine, altered activity of renal enzymes, for example glutamyl synthetase, altered urine osmolarity or urine volume, elevated microalbuminuria, macroalbuminuria, lesions on glomerulae and arterioles, tubular dilatation, hyperphosphataemia and/or need for dialysis. The present invention also encompasses the use of the compounds of the invention for the treatment and/or prophylaxis of sequelae of renal insufficiency, for example pulmonary edema, heart failure, uremia, anemia, electrolyte disorders (for example hyperkalemia, hyponatremia) and disorders in bone and carbohydrate metabolism.

In addition, the compounds of the invention are also suitable for the treatment and/or prophylaxis of asthmatic disorders, pulmonary arterial hypertension (PAH) and other forms of pulmonary hypertension (PH) including left-heart disease-, HIV-, sickle cell anaemia-, thromboembolism- (CTEPH), sarcoidosis-, COPD- or pulmonary fibrosis-associated pulmonary hypertension, chronic-obstructive pulmonary disease (COPD), acute respiratory distress syndrome (ARDS), acute lung injury (ALI), alpha-1-antitrypsin deficiency (AATD), pulmonary fibrosis, pulmonary emphysema (for example pulmonary emphysema induced by cigarette smoke) and cystic fibrosis (CF).

The compounds described in the present invention are also active compounds for control of central nervous system disorders characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory losses, vascular dementia, craniocerebral trauma, stroke, dementia occurring after strokes (post-stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, demyelinization, multiple sclerosis, thalamic degeneration, Creutzfeldt-Jakob dementia, HIV dementia, schizophrenia with dementia or Korsakoff's psychosis. They are also suitable for the treatment and/or prophylaxis of central nervous system disorders such as states of anxiety, tension and depression, CNS-related sexual dysfunctions and sleep disturbances, and for controlling pathological disturbances of the intake of food, stimulants and addictive substances.

In addition, the compounds of the invention are also suitable for controlling cerebral blood flow and are effective agents for controlling migraine. They are also suitable for the prophylaxis and control of sequelae of cerebral infarct (Apoplexia cerebri) such as stroke, cerebral ischemias and skull-brain trauma. The compounds of the invention can likewise be used for controlling states of pain and tinnitus.

In addition, the compounds of the invention have anti-inflammatory action and can therefore be used as anti-inflammatory agents for the treatment and/or prophylaxis of sepsis (SIRS), multiple organ failure (MODS, MOF), inflammatory disorders of the kidney, chronic intestinal inflammations (IBD, Crohn's disease, UC), pancreatitis, peritonitis, rheumatoid disorders, inflammatory skin disorders and inflammatory eye disorders.

Furthermore, the compounds of the invention can also be used for the treatment and/or prophylaxis of autoimmune diseases.

The compounds of the invention are also suitable for the treatment and/or prophylaxis of fibrotic disorders of the internal organs, for example the lung, the heart, the kidney, the bone marrow and in particular the liver, and also dermatological fibroses and fibrotic eye disorders. In the context of the present invention, the term fibrotic disorders includes in particular the following terms: hepatic fibrosis, cirrhosis of the liver, pulmonary fibrosis, endomyocardial fibrosis, nephropathy, glomerulonephritis, interstitial renal fibrosis, fibrotic damage resulting from diabetes, bone marrow fibrosis and similar fibrotic disorders, scleroderma, morphea, keloids, hypertrophic scarring (also following surgical procedures), naevi, diabetic retinopathy, proliferative vitroretinopathy and disorders of the connective tissue (for example sarcoidosis).

The compounds of the invention are also suitable for controlling postoperative scarring, for example as a result of glaucoma operations.

The compounds of the invention can also be used cosmetically for ageing and keratinizing skin.

Moreover, the compounds according to the invention are suitable for the treatment and/or prophylaxis of hepatitis, neoplasms, osteoporosis, glaucoma and gastroparesis.

The present invention further provides for the use of the compounds according to the invention for the treatment and/or prophylaxis of disorders, especially the disorders mentioned above.

The present invention further provides for the use of the compounds of the invention for the treatment and/or prophylaxis of heart failure, angina pectoris, hypertension, pulmonary hypertension, ischaemias, vascular disorders, renal insufficiency, thromboembolic disorders, fibrotic disorders and arteriosclerosis.

The present invention further provides the compounds of the invention for use in a method for the treatment and/or prophylaxis of heart failure, angina pectoris, hypertension, pulmonary hypertension, ischaemias, vascular disorders, renal insufficiency, thromboembolic disorders, fibrotic disorders and arteriosclerosis.

The present invention further provides for the use of the compounds of the invention for production of a medicament for the treatment and/or prophylaxis of disorders, especially the aforementioned disorders.

The present invention further provides for the use of the compounds of the invention for production of a medicament for the treatment and/or prophylaxis of heart failure, angina pectoris, hypertension, pulmonary hypertension, ischaemias, vascular disorders, renal insufficiency, thromboembolic disorders, fibrotic disorders and arteriosclerosis.

The present invention further provides a method for the treatment and/or prophylaxis of disorders, in particular the disorders mentioned above, using an effective amount of at least one of the compounds of the invention.

The present invention further provides a method for the treatment and/or prophylaxis of heart failure, angina pectoris, hypertension, pulmonary hypertension, ischaemias, vascular disorders, renal insufficiency, thromboembolic disorders, fibrotic disorders and arteriosclerosis using an effective amount of at least one of the compounds of the invention.

The compounds according to the invention can be used alone or, if required, in combination with other active ingredients. The present invention further provides medicaments comprising at least one of the compounds of the invention and one or more further active compounds, especially for the treatment and/or prophylaxis of the aforementioned disorders. Preferred examples of suitable combination active ingredients include:

organic nitrates and NO donors, for example sodium nitroprusside, nitroglycerin, isosorbide mononitrate, isosorbide dinitrate, molsidomine or SIN-1, and inhaled NO; and/or compounds which inhibit the breakdown of cyclic guanosine monophosphate (cGMP), for example inhibitors of phosphodiesterases (PDE) 1, 2 and/or 5, especially PDE 5 inhibitors such as sildenafil, vardenafil and tadalafil; and/or agents having antithrombotic activity, for example and with preference from the group of the platelet aggregation inhibitors, the anticoagulants or the profibrinolytic substances; and/or hypotensive active compounds, by way of example and with preference from the group of the calcium antagonists, angiotensin AII antagonists, ACE inhibitors, endothelin antagonists, renin inhibitors, alpha-receptor blockers, beta-receptor blockers, mineralocorticoid receptor antagonists, neutral endopeptidase (NEP) inhibitors and combinations of these groups and the diuretics; and/or lipid metabolism modifiers, by way of example and with preference from the group of the thyroid receptor agonists, cholesterol synthesis inhibitors, by way of example and with preference HMG-CoA reductase or squalene synthesis inhibitors, of the ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein(a) antagonists; and/or antifibrotic agents, by way of example and with preference from the group of the kinase inhibitors or TGF-beta or TNF-alpha modulators.

Antithrombotic agents are preferably understood to mean compounds from the group of the platelet aggregation inhibitors, the anticoagulants or the profibrinolytic substances.

In a preferred embodiment of the invention, the compounds of the invention are administered in combination with a platelet aggregation inhibitor, by way of example and with preference aspirin, clopidogrel, ticlopidine or dipyridamole.

In a preferred embodiment of the invention, the compounds of the invention are administered in combination with a thrombin inhibitor, by way of example and with preference ximelagatran, dabigatran, melagatran, bivalirudin or clexane.

In a preferred embodiment of the invention, the compounds of the invention are administered in combination with a GPIIb/IIIa antagonist, by way of example and with preference tirofiban or abciximab.

In a preferred embodiment of the invention, the compounds according to the invention are administered in combination with a factor Xa inhibitor, by way of example and with preference rivaroxaban (BAY 59-7939), edoxaban (DU-176b), apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds of the invention are administered in combination with heparin or with a low molecular weight (LMW) heparin derivative.

In a preferred embodiment of the invention, the compounds of the invention are administered in combination with a vitamin K antagonist, by way of example and with preference coumarin.

Hypotensive agents are preferably understood to mean compounds from the group of the calcium antagonists, angiotensin AII antagonists, ACE inhibitors, endothelin antagonists, renin inhibitors, alpha-receptor blockers, beta-receptor blockers, mineralocorticoid receptor antagonists, neutral endopeptidase (NEP) inhibitors, and the diuretics.

In a preferred embodiment of the invention, the compounds of the invention are administered in combination with a calcium antagonist, by way of example and with preference nifedipine, amlodipine, verapamil or diltiazem.

In a preferred embodiment of the invention, the compounds of the invention are administered in combination with an alpha-1-receptor blocker, by way of example and with preference prazosin.

In a preferred embodiment of the invention, the compounds of the invention are administered in combination with a beta-receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist, by way of example and with preference losartan, candesartan, valsartan, telmisartan or embursatan or a dual angiotensin AII antagonist/NEP inhibitor, for example and with preference LCZ696 (valsartan/sacubitril).

In a preferred embodiment of the invention, the compounds of the invention are administered in combination with an ACE inhibitor, by way of example and with preference enalapril, captopril, lisinopril, ramipril, delapril, fosinopril, quinopril, perindopril or trandopril.

In a preferred embodiment of the invention, the compounds of the invention are administered in combination with an endothelin antagonist, by way of example and with preference bosentan, darusentan, ambrisentan or sitaxsentan.

In a preferred embodiment of the invention, the compounds of the invention are administered in combination with a renin inhibitor, by way of example and with preference aliskiren, SPP-600 or SPP-800.

In a preferred embodiment of the invention, the compounds of the invention are administered in combination with a mineralocorticoid receptor antagonist, by way of example and with preference spironolactone or eplerenone.

In a preferred embodiment of the invention, the compounds of the invention are administered in combination with a loop diuretic, for example furosemide, torasemide, bumetanide and piretanide, with potassium-sparing diuretics, for example amiloride and triamterene, with aldosterone antagonists, for example spironolactone, potassium canrenoate and eplerenone, and also thiazide diuretics, for example hydrochlorothiazide, chlorthalidone, xipamide and indapamide.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-alpha, PPAR-gamma and/or PPAR-delta agonists, cholesterol absorption inhibitors, polymeric bile acid adsorbers, bile acid reabsorption inhibitors, lipase inhibitors and the lipoprotein(a) antagonists.

In a preferred embodiment of the invention, the compounds of the invention are administered in combination with a CETP inhibitor, by way of example and with preference dalcetrapib, BAY 60-5521, anacetrapib or CETP vaccine (CETi-1).

In a preferred embodiment of the invention, the compounds of the invention are administered in combination with a thyroid receptor agonist, by way of example and with preference D-thyroxine, 3,5,3'-triiodothyronine (T3), CGS 23425 or axitirome (CGS 26214).

In a preferred embodiment of the invention, the compounds of the invention are administered in combination with an HMG-CoA reductase inhibitor from the class of statins, by way of example and with preference lovastatin, simvastatin, pravastatin, fluvastatin, atorvastatin, rosuvastatin or pitavastatin.

In a preferred embodiment of the invention, the compounds of the invention are administered in combination with a squalene synthesis inhibitor, by way of example and with preference BMS-188494 or TAK-475.

In a preferred embodiment of the invention, the compounds of the invention are administered in combination with an ACAT inhibitor, by way of example and with preference avasimibe, melinamide, pactimibe, eflucimibe or SMP-797.

In a preferred embodiment of the invention, the compounds of the invention are administered in combination with an MTP inhibitor, by way of example and with preference implitapide, BMS-201038, R-103757 or JTT-130.

In a preferred embodiment of the invention, the compounds of the invention are administered in combination with a PPAR-gamma agonist, by way of example and with preference pioglitazone or rosiglitazone.

In a preferred embodiment of the invention, the compounds of the invention are administered in combination with a PPAR-delta agonist, by way of example and with preference GW 501516 or BAY 68-5042.

In a preferred embodiment of the invention, the compounds of the invention are administered in combination with a cholesterol absorption inhibitor, by way of example and with preference ezetimibe, tiqueside or pamaqueside.

In a preferred embodiment of the invention, the compounds of the invention are administered in combination with a lipase inhibitor, by way of example and with preference orlistat.

In a preferred embodiment of the invention, the compounds of the invention are administered in combination with a polymeric bile acid adsorber, by way of example and with preference cholestyramine, colestipol, colesolvam, CholestaGel or colestimide.

In a preferred embodiment of the invention, the compounds of the invention are administered in combination with a bile acid reabsorption inhibitor, by way of example and with preference ASBT (=IBAT) inhibitors, for example AZD-7806, S-8921, AK-105, BARI-1741, SC-435 or SC-635.

In a preferred embodiment of the invention, the compounds of the invention are administered in combination with a lipoprotein(a) antagonist, by way of example and with preference gemcabene calcium (CI-1027) or nicotinic acid.

In a preferred embodiment of the invention, the compounds of the invention are administered in combination with a kinase inhibitor, by way of example and with preference nintedanib.

In a preferred embodiment of the invention, the compounds according to the invention are administered with an TGF-beta or TNF-alpha modulator, by way of example and with preference pirfenidone.

The present invention further provides medicaments which comprise at least one compound of the invention, typically together with one or more inert, non-toxic, pharmaceutically suitable excipients, and for the use thereof for the aforementioned purposes.

The compounds according to the invention can act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The compounds according to the invention can be administered in administration forms suitable for these administration routes.

Suitable administration forms for oral administration are those which work according to the prior art and release the compounds of the invention rapidly and/or in a modified manner and which contain the compounds of the invention in crystalline and/or amorphized and/or dissolved form, for example tablets (uncoated or coated tablets, for example with gastric juice-resistant or retarded-dissolution or insoluble coatings which control the release of the compound of the invention), tablets or films/oblates which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can be accomplished with avoidance of a resorption step (for example by an intravenous, intraarterial, intracardiac, intraspinal or intralumbar route) or with inclusion of a resorption (for example by an intramuscular, subcutaneous, intracutaneous, percutaneous or intraperitoneal route). Administration forms suitable for parenteral administration include preparations for injection and infusion in the form of solutions, suspensions, emulsions, lyophilizates or sterile powders.

For the other administration routes, suitable examples are inhalable medicament forms (including powder inhalers, nebulizers), nasal drops, solutions or sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

Preference is given to oral or parenteral administration, especially oral administration.

The compounds according to the invention can be converted to the administration forms mentioned. This can be accomplished in a manner known per se by mixing with inert, non-toxic, pharmaceutically suitable auxiliaries. These excipients include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), colourants (e.g. inorganic pigments, for example iron oxides) and flavour and/or odour correctors.

In general, it has been found to be advantageous in the case of parenteral administration to administer amounts of about 0.001 to 1 mg/kg, preferably about 0.01 to 0.5 mg/kg, of body weight to achieve effective results. In the case of oral administration, the dose is about 0.001 to 2 mg/kg, preferably about 0.001 to 1 mg/kg, of body weight.

It may nevertheless be necessary in some cases to deviate from the stated amounts, specifically as a function of body weight, route of administration, individual response to the active ingredient, nature of the preparation and time or interval over which administration takes place. Thus in some cases it may be sufficient to manage with less than the abovementioned minimum amount, while in other cases the upper limit mentioned must be exceeded. In the case of administration of greater amounts, it may be advisable to divide them into several individual doses over the day.

The working examples which follow illustrate the invention. The invention is not restricted to the examples.

Unless stated otherwise, the percentages in the tests and examples which follow are percentages by weight; parts are parts by weight. Solvent ratios, dilution ratios and concentration data for liquid/liquid solutions are based in each case on volume.

A. EXAMPLES

Abbreviations and Acronyms abs. absolute (=dried)
aq. aqueous solution
calc. calculated
Boc tert-butyloxycarbonyl
br. broad signal (NMR coupling pattern)
CAS No. Chemical Abstracts Service number
Cbz benzyloxycarbonyl
$\delta$ shift in the NMR spectrum (stated in ppm)
d doublet (NMR coupling pattern)
TLC thin-layer chromatography
DCI direct chemical ionization (in MS)
DMAP 4-N,N-dimethylaminopyridine
DMF dimethylformamide
DMSO dimethyl sulphoxide
EDCI N-[3-(dimethylamino)propyl]-N'-ethylcarbodiimide
ent enantiomerically pure
eq. equivalent(s)
ESI electrospray ionization (in MS)
Et ethyl
h hour(s)
HATU N-[(dimethylamino)(3H-[1,2,3]triazolo[4,5-b]-pyridine-3-yloxy)methylene]-N-methylmethanaminium hexafluorophosphate
HOBT 1H-benzotriazol-1-ol
HPLC high-pressure, high-performance liquid chromatography
HRMS high-resolution mass spectrometry
ID internal diameter
conc. concentrated
LC-MS liquid chromatography-coupled mass spectrometry
LiHMDS lithium hexamethyldisilazide
m multiplet
Me methyl
min minute(s)
MS mass spectrometry
NMR nuclear magnetic resonance spectrometry
PDA photodiode array detector
$Pd_2dba_3$ tris(dibenzylideneacetone)dipalladium
Ph phenyl
q quartet (NMR coupling pattern)
quint. quintet (NMR coupling pattern)
rac racemic
rel relative stereochemistry R$_F$ retention factor (in thin-layer chromatography)
RT room temperature
R$_t$ retention time (in HPLC)
s singlet (NMR coupling pattern)
t triplet (NMR coupling pattern)
TFA Trifluoroacetic acid
THF tetrahydrofuran
TBTU (benzotriazol-1-yloxy)bisdimethylaminomethylium fluoroborate
UPLC-MS ultra-pressure liquid chromatography-coupled mass spectrometry
UV ultraviolet spectrometry
v/v volume to volume ratio (of a solution)
Xantphos 4,5-bis(diphenylphosphino)-9,9-dimethylxanthene
XPHOS dicyclohexyl(2',4',6'-triisopropylbiphenyl-2-yl)phosphine LC-MS and HPLC Methods:

Method 1 (LC-MS):
Instrument: Micromass Quattro Premier with Waters UPLC Acquity; column: Thermo Hypersil GOLD 1.9 50×1 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→1.5 min 10% A→2.2 min 10% A; oven: 50° C.; flow rate: 0.33 ml/min; UV detection: 210 nm Method 2 (LC-MS):
Instrument: Waters ACQUITY SQD UPLC system; column: Waters Acquity UPLC HSS T3 1.8μ 50×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; oven: 50° C.; flow rate: 0.40 ml/min; UV detection: 210-400 nm.

Method 3 (LC-MS):
Instrument: Micromass Quattro Premier with Waters UPLC Acquity; column: Thermo Hypersil GOLD 1.9 50×1 mm; mobile phase A: 1 l of water+0.5 ml of 50% strength formic acid, mobile phase B: 1 l of acetonitrile+0.5 ml of 50% strength formic acid; gradient: 0.0 min 97% A→0.5 min 97% A→3.2 min 5% A→4.0 min 5% A; oven: 50° C.; flow rate: 0.3 ml/min; UV detection: 210 nm.

Method 4 (Preparative HPLC):
Chromatorex C18 10μ 250×20 mm gradient: A=water+0.5% HCOOH, B=CH$_3$CN, 0 min=5% B, 3 min=5% B pre-rinse without substance, then injection, 5 min=5% B, 25 min=30% B, 38 min=30% B, 38.1 min=95% B, 43 min=95% B, 43.01 min=5% B, 48.0 min=5% B flow rate 20 ml/min, wavelength 210 nm.

Method 5 (Preparative HPLC):
Chromatorex C18 10μ 250×20 mm gradient: A=water+0.5% HCOOH, B=CH$_3$CN, 0 min=5% B, 3 min=5% B pre-rinse without substance, then injection, 5 min=5% B, 25 min=50% B, 38.1 min=50% B, 38 min=95% B, 43 min=95% B, 43.01 min=5% B, 48.0 min=5% B flow rate 20 ml/min, wavelength 210 nm.

Method 6 (Preparative HPLC):
XBridge Prep. C18 5μ 50×19 mm gradient: A=water+0.5% NH$_4$OH, B=CH$_3$CN, 0 min=5% B, 3 min=5% B pre-rinse without substance, then injection, 5 min=5% B, 25 min=50% B, 38 min=50% B, 38.1 min=95% B, 43 min=95% B, 43.01 min=5% B, 48.0 min=5% B flow rate 15 ml/min, wavelength 210 nm.

Method 7 (LC-MS):
MS instrument: Waters (Micromass) QM; HPLC instrument: Agilent 1100 series; column: Agilent ZORBAX Extend-C18 3.0×50 mm 3.5 micron; mobile phase A: 1 l of water+0.01 mol of ammonium carbonate, mobile phase B: 1 l of acetonitrile; gradient: 0.0 min 98% A→0.2 min 98% A→3.0 min 5% A→4.5 min 5% A; oven: 40° C.; flow rate: 1.75 ml/min; UV detection: 210 nm.

Method 8 (LC-MS):
Instrument: Waters ACQUITY SQD UPLC system; column: Waters Acquity UPLC HSS T3 1.8μ 30×2 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; oven: 50° C.; flow rate: 0.60 ml/min; UV detection: 208-400 nm.

Method 9 (Preparative HPLC):
MS instrument: Waters, HPLC instrument: Waters (column Waters X-Bridge C18, 18 mm×50 mm, 5 m, mobile phase A: water+0.05% triethylamine, mobile phase B: acetonitrile (ULC)+0.05% triethylamine, with gradient; flow rate: 40 ml/min; UV detection: DAD; 210-400 nm).
or:
MS instrument: Waters, HPLC instrument: Waters (column Phenomenex Luna 5μ C18(2) 100 A, AXIA Tech. 50×21.2 mm, mobile phase A: water+0.05% formic acids, mobile phase B: acetonitrile (ULC)+0.05% formic acid, with gradient; flow rate: 40 ml/min; UV detection: DAD; 210-400 nm).

Method 10 (LC-MS):
MS instrument: Waters SQD; HPLC instrument: Waters UPLC; column: Zorbax SB-Aq (Agilent), 50 mm×2.1 mm, 1.8 m; mobile phase A: water+0.025% formic acid, mobile phase B: acetonitrile (ULC)+0.025% formic acid; gradient: 0.0 min 98% A—0.9 min 25% A—1.0 min 5% A—1.4 min 5% A—1.41 min 98% A—1.5 min 98% A; oven: 40° C.; flow rate: 0.600 ml/min; UV detection: DAD; 210 nm.

Method 11 (MS):
Instrument: Waters ZQ 2000; electrospray ionization; mobile phase A: 1 l of water+0.25 ml of 99% strength formic acid, mobile phase B: 1 l of acetonitrile+0.25 ml of 99% strength formic acid; 25% A, 75% B; flow rate: 0.25 ml/min.

Method 12 (DCI-MS):
Instrument: Thermo Fisher-Scientific DSQ; chemical ionization; reactant gas NH$_3$; source temperature: 200° C.; ionization energy 70 eV.

Method 13 (LC-MS):
MS instrument: Waters (Micromass) Quattro Micro; HPLC instrument: Agilent 1100 series; column: YMC-Triart C18 3μ 50×3 mm; mobile phase A: 1 l of water+0.01 mol of ammonium carbonate, mobile phase B: 1 l of acetonitrile; gradient: 0.0 min 100% A—2.75 min 5% A—4.5 min 5% A; oven: 40° C.; flow rate: 1.25 ml/min; UV detection: 210 nm.

Method 14 (GC-MS):
Instrument: Thermo Scientific DSQII, Thermo Scientific Trace GC Ultra; column: Restek RTX-35MS, 15 m×200 μm×0.33 μm; constant flow rate with helium: 1.20 ml/min; oven: 60° C.; inlet: 220° C.; gradient: 60° C., 30° C./min→300° C. (maintain for 3.33 min).

Method 15 (LC-MS, Analytical):
Instrument: Agilent MS Quad 6150; HPLC: Agilent 1290; column: Waters Acquity UPLC HSS T3 1.8μ 50×2.1 mm; mobile phase A: 1 l of water+0.25 ml of 99% strength formic acid, mobile phase B: 1 l of acetonitrile+0.25 ml of 99% strength formic acid; gradient: 0.0 min 90% A→0.3 min 90% A→1.7 min 5% A→3.0 min 5% A; oven: 50° C.; flow rate: 1.20 ml/min; UV detection: 205-305 nm.

Method 16 (LC-MS, Analytical):

MS instrument type: Thermo Scientific FT-MS; instrument type UHPLC+: Thermo Scientific UltiMate 3000; column: Waters, HSST3, 2.1×75 mm, C18 1.8 μm; mobile phase A: 1 l of water+0.01% formic acid; mobile phase B: 1 l of acetonitrile+0.01% formic acid; gradient: 0.0 min 10% B→2.5 min 95% B→3.5 min 95% B; oven: 50° C.; flow rate: 0.90 ml/min; UV detection: 210 nm/optimum integration path 210-300 nm.

Unless stated otherwise, the percentages in the tests and examples which follow are percentages by weight; parts are parts by weight. Solvent ratios, dilution ratios and concentration data for liquid/liquid solutions are based in each case on volume.

The multiplicities of proton signals in $^1$H NMR spectra reported in the paragraphs which follow represent the signal form observed in each case and do not take account of any higher-order signal phenomena. In all $^1$H NMR spectra data, the chemical shifts δ are stated in ppm.

Additionally, the starting materials, intermediates and working examples may be present as hydrates. There was no quantitative determination of the water content. In certain cases, the hydrates may affect the $^1$H NMR spectrum and possibly shift and/or significantly broaden the water signal in the $^1$H NMR.

In $^1$H NMR spectra, the methyl group of the chemical system "2-methylpyrazolo[1,5-a]pyridine" appears as a singlet (frequently in DMSO-$d_6$ and in the range of 2.40-2.60 ppm) and is clearly distinguishable as such, is superposed by the solvent signals or is completely under the signals of the solvents. In the $^1$H NMR spectra, this signal can be assumed to be present.

When compounds of the invention are purified by preparative HPLC by the above-described methods in which the mobile phases contain additives, for example trifluoroacetic acid, formic acid or ammonia, the compounds of the invention may be obtained in salt form, for example as trifluoroacetate, formate or ammonium salt, if the compounds of the invention contain a sufficiently basic or acidic functionality. Such a salt can be converted to the corresponding free base or acid by various methods known to the person skilled in the art.

In the case of the synthesis intermediates and working examples of the invention described hereinafter, any compound specified in the form of a salt of the corresponding base or acid is generally a salt of unknown exact stoichiometric composition, as obtained by the respective preparation and/or purification process. Unless specified in more detail, additions to names and structural formulae, such as "hydrochloride", "trifluoroacetate", "sodium salt" or "x HCl", "x $CF_3CO_2H$", "x $Na^+$" should not therefore be understood in a stoichiometric sense in the case of such salts, but have merely descriptive character with regard to the salt-forming components present therein.

This applies correspondingly if synthesis intermediates or working examples or salts thereof were obtained in the form of solvates, for example hydrates, of unknown stoichiometric composition (if they are of a defined type) by the preparation and/or purification processes described.

Starting Compounds and Intermediates:

Example 1A

2-[(2,6-Difluorobenzyl)oxy]-4-methylpyridine

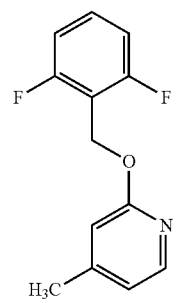

A mixture of 5.00 g (24.2 mmol, 1.0 eq.) of 2,6-difluorobenzyl bromide [CAS No: 85118-00-9] and 3.16 g (29.0 mmol, 1.2 eq.) of 2-hydroxy-4-methylpyridine [CAS No: 13466-41-6] was dissolved in 50 ml of THF. 7.99 g (29.0 mmol, 1.2 eq.) of silver carbonate were added to the solution, and the mixture was heated at reflux with exclusion of light overnight. Subsequently, the reaction mixture was filtered through kieselguhr, eluting with ethyl acetate, and the filtrate was concentrated. The crude product was purified by means of Biotage Isolera (100 g silica gel cartridge, cyclohexane/ethyl acetate gradient, 0% to 10% ethyl acetate). This gave 3.51 g of the title compound (61% of theory).

TLC (silica gel, cyclohexane/ethyl acetate 10:1): $R_f$=0.50
LC-MS (Method 2): $R_t$=1.17 min
MS (ESpos): m/z=236 (M+H)$^+$
$^1$H-NMR (400 Mhz, DMSO-$d_6$): δ [ppm]=2.26 (s, 3H), 5.35 (s, 2H), 6.66 (s, 1H), 6.86 (d, 1H), 7.12-7.21 (m, 2H), 7.47-7.56 (m, 1H), 8.06 (d, 1H).

Example 2A

1-Amino-2-[(2,6-difluorobenzyl)oxy]-4-methylpyridinium 2,4,6-trimethylbenzenesulphonate

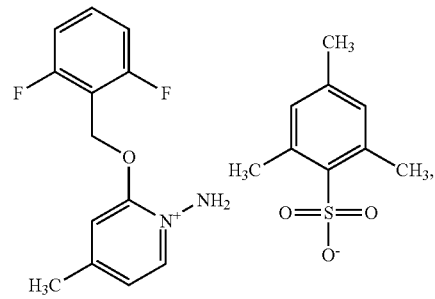 [SMILES: Cc1cc[n+](N)c(OCc2c(F)cccc2F)c1 ; Cc1cc(C)c(S(=O)(=O)[O-])c(C)c1]

A mixture of 3.4 ml (43.9 mmol, 10 eq.) of trifluoroacetic acid and 0.33 ml water was cooled to −5° C. At this temperature, 1.88 g (6.59 mmol, 1.5 eq.) of ethyl (1E)-N-[(mesitylsulphonyl)oxy]ethanimidoate [CAS No: 38202-27-6] were added in portions. After 1.5 h, 30 ml of ice-water were added, the mixture was stirred briefly, and the precipitated O-(2-mesitylenesulphonyl)hydroxylamine (MSH) was filtered off using a precooled frit and washed with 30 ml of ice-water. The water-moist O-(2-mesitylenesulphonyl)hydroxylamine was dissolved in 12 ml of dichloromethane, dried with magnesium sulphate and filtered, and the filtrate was added dropwise directly to a solution of 1.03 g (4.39 mmol, 1.0 eq.) of 2-[(2,6-difluorobenzyl)oxy]-4-methylpyridine from Example 1A in 2 ml of dichloromethane. The mixture was stirred at RT overnight. Subsequently, diethyl ether was added dropwise, and the precipitate obtained was filtered off, washed with diethyl ether and dried. 1.3 g of the title compound were isolated (59% of theory, purity 90%).

$^1$H-NMR (400 Mhz, DMSO-$d_6$): δ [ppm]=2.17 (s, 3H), 2.46-2.57 (s, 3H and s, 6H superposed by the solvent signal), 5.64 (s, 2H), 6.74 (s, 2H), 7.23-7.48 (m, 4H), 7.60-7.70 (m, 1H), 7.86 (br s, 1H), 8.44 (d, 1H).

Example 3A

Ethyl 7-[(2,6-difluorobenzyl)oxy]-2,5-dimethylpyrazolo[1,5-a]pyridine-3-carboxylate

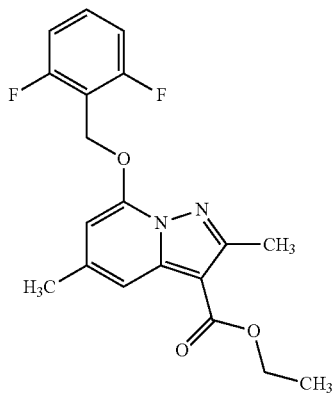 [SMILES: CCOC(=O)c1c(C)nn2c(OCc3c(F)cccc3F)cc(C)cc12]

1.62 g (3.60 mmol, 1.0 eq.) of 1-amino-2-[(2,6-difluorobenzyl)oxy]-4-methylpyridinium 2,4,6-trimethylbenzenesulphonate from Example 2A were dissolved in 36 ml of DMF, and 0.84 ml (7.19 mmol, 2.0 eq.) of ethyl but-2-ynoate [CAS No: 4341-76-8] were added. 0.994 g (7.19 mmol, 2.0 eq.) of potassium carbonate was added and the mixture was stirred at RT for 1.5 h. Subsequently, the mixture was poured onto 150 ml of water and stirred briefly, and the precipitated solids were filtered off, washed with water and dried. This gave 440 mg of the title compound (45% of theory, 87%).

LC-MS (Method 2): $R_t$=1.22 min

MS (ESpos): m/z=361 (M+H)$^+$

Example 4A

7-[(2,6-Difluorobenzyl)oxy]-2,5-dimethylpyrazolo[1,5-a]pyridine-3-carboxylic acid

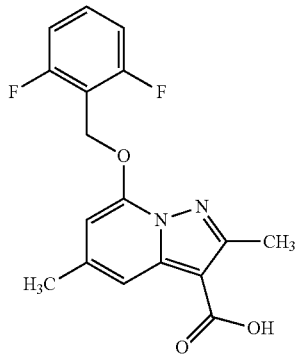 [SMILES: Cc1cc(OCc2c(F)cccc2F)n2nc(C)c(C(=O)O)c2c1]

4.9 ml (4.88 mmol, 4.0 eq.) of 1 N aqueous sodium hydroxide solution were added to a solution of 0.440 g (1.22 mmol, 1 eq.) of ethyl 7-[(2,6-difluorobenzyl)oxy]-2,5-dimethylpyrazolo[1,5-a]pyridine-3-carboxylate from Example 3A in 12.7 ml of dioxane, and the mixture was stirred at 90° C. for 36 h. Subsequently, the reaction mixture was concentrated and the precipitated solids were filtered off. The filtrate was acidified with 6 N aqueous hydrochloric acid and stirred briefly, and the precipitated solids were filtered off, washed with water and dried. This gave 248 mg of the title compound (61% of theory, purity 60%), which was converted further without further purification.

LC-MS (Method 2): $R_t$=0.96 min

MS (ESpos): m/z=333 (M+H)$^+$

Example 5A 2-(Benzyloxy)-4-methylpyridine

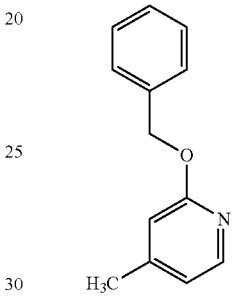

A mixture of 13.6 ml (114 mmol, 1.0 eq.) of benzyl bromide and 15.0 g (137 mmol, 1.2 eq.) of 2-hydroxy-4-methylpyridine [CAS No: 13466-41-6] was dissolved in 470 ml of THF. 37.9 g (137 mmol, 1.2 eq.) of silver carbonate were added to the solution, and the mixture was heated at reflux with exclusion of light overnight. Subsequently, the reaction mixture was filtered through kieselguhr, eluting with ethyl acetate, and the filtrate was concentrated. The crude product was purified by silica gel chromatography (700 g of silica gel, cyclohexane/ethyl acetate 95:5). This gave 21.4 g of the title compound (94% of theory).

TLC (silica gel, cyclohexane/ethyl acetate 9:1): $R_F$=0.41

LC-MS (Method 2): $R_t$=1.12 min

MS (ESpos): m/z=200 (M+H)$^+$ $^1$H-NMR (400 Mhz, DMSO-$d_6$): δ [ppm]=2.27 (s, 3H), 5.33 (s, 2H), 6.70 (s, 1H), 6.83 (d, 1H), 7.27-7.45 (m, 5H), 8.02 (d, 1H).

Example 6A

1-Amino-2-(benzyloxy)-4-methylpyridinium 2,4,6-trimethylbenzenesulphonate

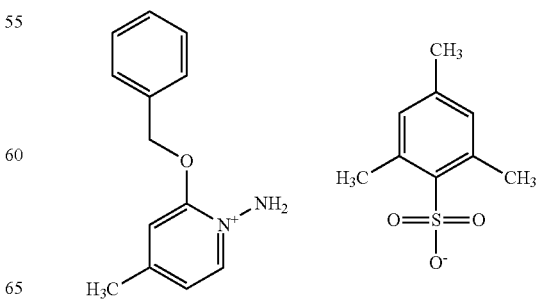

A mixture of 18.0 ml of trifluoroacetic acid (233 mmol, 10 eq.) and 2.66 ml of water was cooled to −5° C. At this temperature, 9.99 g (35.0 mmol, 1.5 eq.) of ethyl (1E)-N-[(mesitylsulphonyl)oxy]ethanimidoate [CAS No: 38202-27-6] were added a little at a time. After 1.5 h, 150 ml of ice-water were added, and the mixture was stirred briefly and extracted with 100 ml of dichloromethane. The organic phase was dried with magnesium sulphate and filtered, and the resulting solution of O-(2-mesitylenesulphonyl)hydroxylamine (MSH) was added dropwise directly to a solution, cooled to 0° C., of 4.65 g (23.3 mmol, 1.0 eq.) of 2-(benzyloxy)-4-methylpyridine from Example 5A in 50 ml of dichloromethane. The mixture was stirred at RT for 2 h. Subsequently, 1 l of diethyl ether was added dropwise, and precipitated solids were filtered off, washed with 250 ml of diethyl ether and dried. 4.6 g of the title compound were isolated (48% of theory).

LC-MS (Method 2): R$_t$=0.45 min;
MS (ESpos): m/z=215 (C$_{13}$H$_{15}$N$_2$O) (M)$^+$; R$_t$=0.57 min;
MS (ESneg): m/z=199 (C$_9$H$_{11}$O$_3$S)$^-$;

Example 7A

Ethyl 7-(benzyloxy)-2,5-dimethylpyrazolo[1,5-a]pyridine-3-carboxylate

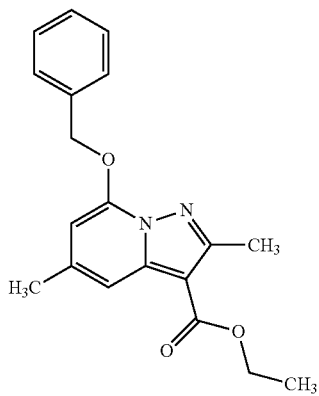 [SMILES: CCOC(=O)c1c(C)nn2c(OCc3ccccc3)cc(C)cc12]

11.7 g (28.2 mmol, 1.0 eq.) of 1-amino-2-(benzyloxy)-4-methylpyridinium 2,4,6-trimethylbenzenesulphonate from Example 6A were dissolved in 280 ml of DMF, and 6.6 ml (56 mmol, 2.0 eq.) of ethyl but-2-ynoate [CAS No: 4341-76-8] were added. 7.8 g (56 mmol, 2.0 eq.) of potassium carbonate was added and the mixture was stirred at RT for 1 h. Subsequently, 3.9 g (28 mmol, 1 eq.) of potassium carbonate was added and the mixture was stirred at RT for a further 16 h. Then the mixture was poured onto 540 ml of water and stirred briefly, and the precipitated solids were filtered off, washed with 220 ml of water and dried. This gave 3.1 g of the title compound (34% of theory, purity 87%).

LC-MS (Method 2): R$_t$=1.20 min
MS (ESpos): m/z=325 (M+H)$^+$
$^1$H-NMR (400 Mhz, DMSO-d$_6$): δ [ppm]=1.34 (t, 3H), 2.43 (s, 3H), 4.27 (q, 2H), 5.43 (s, 2H), 6.60 (d, 1H), 7.37-7.49 (m, 4H), 7.52-7.59 (m, 2H), [s, 3H under solvent signal].

Example 8A

Ethyl 7-hydroxy-2,5-dimethylpyrazolo[1,5-a]pyridine-3-carboxylate

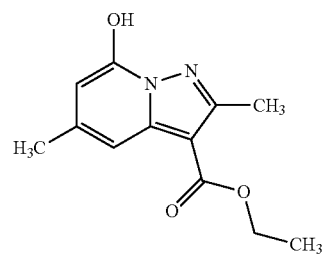 [SMILES: CCOC(=O)c1c(C)nn2c(O)cc(C)cc12]

2 g (5.98 mmol) of ethyl 7-(benzyloxy)-2,5-dimethylpyrazolo[1,5-a]pyridine-3-carboxylate from Example 7A were initially charged in 80 ml of ethanol under argon, and 636 mg (0.59 mmol, 10%) of palladium on activated carbon and 18 ml (179.42 mmol) of cyclohexene were added. The reaction mixture was stirred under reflux for 2.5 hours. Then the reaction mixture was filtered through kieselguhr and washed with ethanol, and the filtrate was concentrated. The residue was taken up in DMSO and acetonitrile and purified by preparative HPLC (RP18 column, mobile phase: acetonitrile/water gradient with addition of 0.1% TFA). The product fractions were combined, concentrated and lyophilized. This gave 1.2 g of the target compound (86% of theory).

LC-MS (Method 7): R$_t$=1.60 min
MS (ESpos): m/z=235 (M+H)$^+$
$^1$H-NMR (500 Mhz, DMSO-d$_6$): δ=1.33 (t, 3H), 2.35 (s, 3H), 2.54 (s, 3H; obscured under solvent peak), 4.26 (q, 2H), 6.17 (d, 1H), 7.26 (s, 1H).

Example 9A

Ethyl 2,5-dimethyl-7-[(2,3,6-trifluorobenzyl)oxy]pyrazolo[1,5-a]pyridine-3-carboxylate

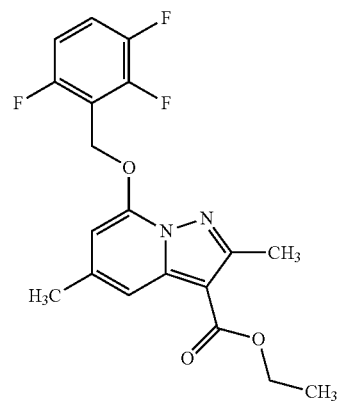 [SMILES: CCOC(=O)c1c(C)nn2c(OCc3c(F)ccc(F)c3F)cc(C)cc12]

1.2 g (5.25 mmol) of ethyl 7-hydroxy-2,5-dimethylpyrazolo[1,5-a]pyridine-3-carboxylate from Example 8A were dissolved in 48 ml of THF. 1.7 g (10.50 mmol) of 2,3,6-trifluorobenzyl alcohol and 2.9 g (11.03 mmol) of triphenylphosphine were added. Subsequently, 2.2 ml (11.03 mmol) of diisopropyl (E)-diazene-1,2-dicarboxylate were added to the solution, which was stirred at RT for 1 h. 120 ml of tert-butyl methyl ether were added, then the mixture was stirred briefly, and the solids formed were filtered off and dried under high vacuum. This gave 1.2 g of the target compound (62% of theory).

LC-MS (Method 2): $R_t$=1.22 min

MS (ESpos): m/z=379 (M+H)$^+$ $^1$H-NMR (500 Mhz, DMSO-$d_6$): δ=1.34 (t, 3H), 2.46 (s, 3H), 2.51 (s, 3H; obscurred under solvent peak), 4.28 (d, 2H), 5.51 (s, 2H), 6.70 (s, 1H), 7.29-7.37 (m, 1H), 7.48 (s, 1H), 7.66-7.76 (m, 1H).

Example 10A 2,5-Dimethyl-7-[(2,3,6-trifluorobenzyl)oxy]pyrazolo[1,5-a]pyridine-3-carboxylic acid

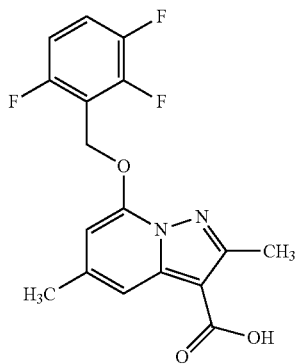 [SMILES: Cc1cc(OCc2c(F)ccc(F)c2F)n2nc(C)c(C(=O)O)c2c1]

700 mg (1.81 mmol) of ethyl 2,5-dimethyl-7-[(2,3,6-trifluorobenzyl)oxy]pyrazolo[1,5-a]pyridine-3-carboxylate from Example 9A were initially charged in 18 ml of dioxane and heated to 90° C. 4.5 ml of dioxane and 7.25 ml (14.50 mmol) of 2 N aqueous sodium hydroxide solution were added, and the reaction mixture was stirred at 90° C. for two days. Another 3.63 ml (7.26 mmol) of 2 N aqueous sodium hydroxide solution were added and the mixture was stirred at 90° C. for a further 2 hours. 15 ml of 1 N aqueous hydrochloric acid were added, and the reaction solution was stirred for 30 min. In the course of this, solids precipitated out. This suspension was filtered, and the solids filtered off were washed with a little water and dried under high vacuum. This gave 358 mg of the target compound (54% of theory).

LC-MS (Method 2): $R_t$=0.97 min

MS (ESpos): m/z=351 (M+H)$^+$

Example 11A

Methyl 2-cyclopropyl-7-[(2,6-difluorobenzyl)oxy]-5-methylpyrazolo[1,5-a]pyridine-3-carboxylate

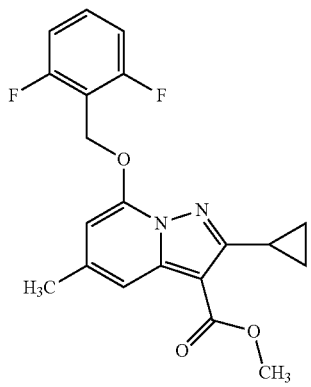 [SMILES: COC(=O)c1c(C2CC2)nn2c(OCc3c(F)cccc3F)cc(C)cc12]

1.0 g (2.22 mmol) of 1-amino-2-[(2,6-difluorobenzyl)oxy]-4-methylpyridinium 2,4,6-trimethylbenzenesulphonate from Example 2A were dissolved in 7.2 ml of DMF, and 496 mg (4.00 mmol) of methyl 3-cyclopropylprop-2-ynoate were added. 552 mg (4.00 mmol) of potassium carbonate was added and the mixture was stirred at RT for 3 h. Subsequently, the mixture was poured onto 50 ml of water and stirred briefly, and the precipitated solids were filtered off, washed with water and dried. This gave 384 mg of the title compound (46% of theory).

LC-MS (Method 2): $R_t$=1.20 min

MS (ESpos): m/z=373 (M+H)$^+$ $^1$H-NMR (500 Mhz, DMSO-$d_6$): δ [ppm]=0.88-0.94 (m, 2H), 0.95-1.00 (m, 2H), 2.43 (s, 3H), 2.70-2.77 (m, 1H), 3.83 (s, 3H), 5.46 (s, 2H), 6.66 (s, 1H), 7.21-7.27 (m, 2H), 7.48 (s, 1H), 7.57-7.64 (m, 1H).

Example 12A

2-Cyclopropyl-7-[(2,6-difluorobenzyl)oxy]-5-methylpyrazolo[1,5-a]pyridine-3-carboxylic acid

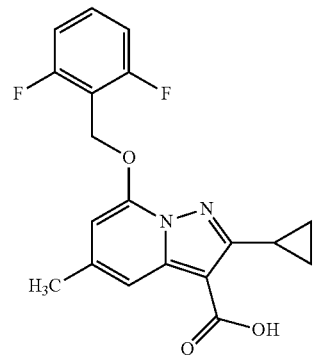 [SMILES: Cc1cc(OCc2c(F)cccc2F)n2nc(C3CC3)c(C(=O)O)c2c1]

10.2 ml (10.2 mmol) of 1 N aqueous sodium hydroxide solution were added to a solution of 384 mg (1.02 mmol) of methyl 2-cyclopropyl-7-[(2,6-difluorobenzyl)oxy]-5-methylpyrazolo[1,5-a]pyridine-3-carboxylate from Example 99A in 10.6 ml of dioxane, and the mixture was stirred at 100° C. for 7 h. The reaction solution was cooled and adjusted to pH 2 with 1 N hydrochloric acid. The solids that precipitated out were filtered off and dried under high vacuum. More 1 N hydrochloric acid was added to the filtrate. The solids that precipitated out were filtered off and dried under high vacuum together with the previously isolated solids. A total of 361 mg of the title compound (74% by LC-MS, 73% of theory) were obtained and were converted without further purification.

LC-MS (Method 2): $R_t$=1.00 min

MS (ESpos): m/z=359 (M+H)$^+$ $^1$H-NMR (400 Mhz, DMSO-$d_6$): δ [ppm]=0.87-0.99 (m, 4H), 2.42 (s, 3H), 2.73-2.82 (m, 1H), 5.45 (s, 2H), 6.61 (s, 1H), 7.20-7.28 (m, 2H), 7.48 (s, 1H), 7.55-7.65 (m, 1H), 12.29 (br. s, 1H).

Example 13A

3-[(2,6-Difluorobenzyl)oxy]-5-methylpyrazine-2-amine

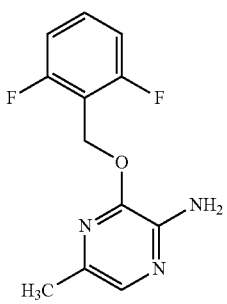 [SMILES: Cc1cnc(N)c(OCc2c(F)cccc2F)n1]

4.86 g of potassium tert-butoxide (43.3 mmol, 3.0 eq.) were added to a solution of 2.71 g of (2,6-difluorophenyl)methanol [CAS No.: 19064-18-7] (18.8 mmol, 1.3 eq.) in 120 ml of 1,2-dimethoxyethane, and the mixture was stirred at RT for 60 min. Subsequently, 2.60 g of 2-amino-3-chloro-5-methylpyrazine hydrochloride [CAS No.: 89182-14-9] (14.4 mmol, 1.0 eq.) were added and the mixture was stirred at 80° C. overnight. After cooling to room temperature, saturated aqueous sodium hydrogencarbonate solution was added and the aqueous phase was extracted three times with dichloromethane. The combined organic phases were washed with saturated aqueous sodium chloride solution, dried over magnesium sulphate, filtered and concentrated. The residue was purified by means of Biotage Isolera (340 g silica gel cartridge, cyclohexane/ethyl acetate gradient, 10%→72% ethyl acetate). This gave 1.77 g of the title compound (39% of theory, purity 85%).

LC-MS (Method 2): $R_t$=0.94 min
MS (ESpos): m/z=252 (M+H)$^+$
$^1$H-NMR (400 Mhz, DMSO-d$_6$): δ [ppm]=2.20 (s, 3H), 5.35 (s, 2H), 5.88 (s, 2H), 7.09-7.23 (m, 2H), 7.37 (s, 1H), 7.46-7.57 (m, 1H).

Example 14A

Ethyl 8-[(2,6-difluorobenzyl)oxy]-2,6-dimethylimidazo[1,2-a]pyrazine-3-carboxylate

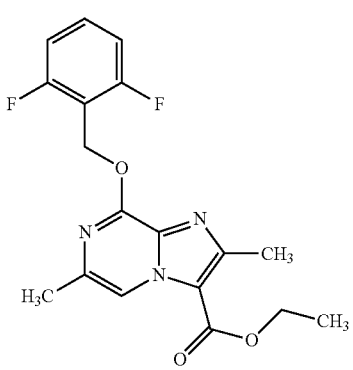 [SMILES: CCOC(=O)c1c(C)nc2c(OCc3c(F)cccc3F)nc(C)cn12]

4 A molecular sieve and 11.1 g of ethyl 2-chloroacetoacetate [CAS No.: 609-15-4] (70.5 mmol, 10 eq.) were added to a solution of 1.77 g of 3-[(2,6-difluorobenzyl)oxy]-5-methylpyrazine-2-amine (7.05 mmol, 1.0 eq.) from Example 13A in 50 ml of ethanol, and the mixture was heated at reflux overnight. Subsequently, 11.1 g of ethyl 2-chloroacetoacetate (70.5 mmol, 10.0 eq) were added and the mixture was heated to reflux overnight. Then the mixture was filtered, the filtrate was concentrated, the residue obtained was extracted by stirring with diethyl ether and filtered, and the filtrate was concentrated. The residue was purified twice by means of Biotage Isolera (120 g silica gel cartridge, cyclohexane/ethyl acetate gradient). 0.81 g of the title compound was isolated (16% of theory; 52% purity).

LC-MS (Method 2): $R_t$=1.28 min
MS (ESpos): m/z=362 (M+H)$^+$

Example 15A

8-[(2,6-Difluorobenzyl)oxy]-2,6-dimethylimidazo[1,2-a]pyrazine-3-carboxylic acid

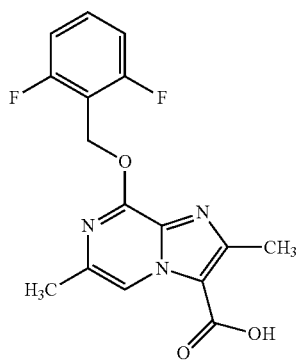 [SMILES: Cc1cn2c(C(=O)O)c(C)nc2c(OCc2c(F)cccc2F)n1]

5.8 ml of 1 N aqueous sodium hydroxide solution (5.8 mmol, 5 eq.) were added to a solution of 800 mg of ethyl 8-[(2,6-difluorobenzyl)oxy]-2,6-dimethylimidazo[1,2-a]pyrazine-3-carboxylate (52% purity, 1.15 mmol, 1.0 eq.) from Example 14A in 10 ml of dioxane, and the mixture was stirred at RT for 2 h. Subsequently, the mixture was concentrated, the residue was taken up in water and insoluble solid was filtered off. The filtrate was acidified with 1 N aqueous hydrochloric acid, and the solid formed was filtered off and dried. 354 mg of the title compound were isolated (83% of theory; 90% purity).

LC-MS (Method 2): $R_t$=0.99 min
MS (ESpos): m/z=334 (M+H)$^+$
$^1$H-NMR (400 Mhz, DMSO-d$_6$): δ [ppm]=2.41 (s, 3H), 2.54 (s, 3H hidden under solvent peak), 5.55 (s, 2H), 7.12-7.28 (m, 2H), 7.49-7.64 (m, 1H), 8.64 (s, 1H), 13.20-13.66 (br s, 1H).

Example 16A

2-Methyl-2-nitropropyl trifluoromethanesulphonate

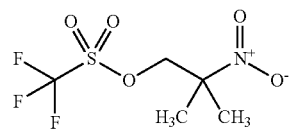

1.0 g (8.40 mmol) of 2-methyl-2-nitropropan-1-ol was initially charged in 20 ml of dichloromethane, 1.0 ml (12.59 mmol) of pyridine was added, the mixture was cooled to 0° C. and 1.85 ml (10.91 mmol) of trifluoromethanesulphonic anhydride was added slowly. The mixture was then stirred at 0° C. for 1 h. The course of the reaction was monitored by TLC (cyclohexane/ethyl acetate 7/3, staining reagent: potassium permanganate stain). The reaction solution was washed in each case once with water and saturated aqueous sodium chloride solution. The organic phase was dried over sodium sulphate and filtered and the filtrate was concentrated. This gave 2.18 g of the target compound (99% of theory). The target compound was stored at −18° C. and used without further purification.

MS (Method 12):

MS (ESpos): m/z=269 (M+NH$_4$)$^+$ $^1$H-NMR (400 Mhz, DMSO-d$_6$) δ=1.64 (s, 6H), 5.13 (s, 2H).

Example 17A

3-Bromo-7-[(2,6-difluorobenzyl)oxy]-2,5-dimethyl-pyrazolo[1,5-a]pyridine

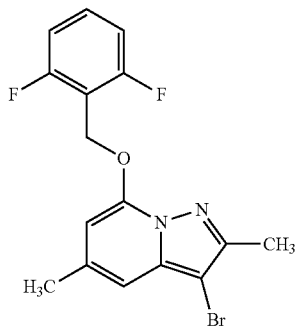 [SMILES: Cc1cc(OCc2c(F)cccc2F)n2nc(C)c(Br)c2c1]

3.79 g (45.14 mmol) of sodium bicarbonate were added to a solution of 5.0 g (15.1 mmol) of 7-[(2,6-difluorobenzyl)oxy]-2,5-dimethylpyrazolo[1,5-a]pyridine-3-carboxylic acid from Example 4A in 60 ml of DMF. At RT, a solution of 2.81 g (15.80 mmol) of N-bromosuccinimide in 40 ml of DMF was, very slowly [2.6 ml/h], added dropwise using a syringe pump. Subsequently, another 134 mg (0.75 mmol) of N-bromosuccinimide in 2 ml of DMF were, very slowly [2.6 ml/h], added dropwise at RT using a syringe pump. The reaction solution was diluted with dichloromethane and then washed twice with water. The combined aqueous phases were reextracted twice with dichloromethane. The combined organic phases were dried over sodium sulfate, filtered and concentrated. The residue was stirred with water, and the solid obtained was filtered off and dried under high vacuum. 4.80 g of the title compound were isolated (84% of theory).

LC-MS (Method 2): R$_t$=1.25 min

MS (ESpos): m/z=367 (M+H)$^+$ $^1$H-NMR (400 Mhz, DMSO-d$_6$): δ [ppm]=2.30 (s, 3H), 2.40 (s, 3H), 5.43 (s, 2H), 6.49 (s, 1H), 6.92 (s, 1H), 7.20-7.30 (m, 2H), 7.57-7.67 (m, 1H).

Example 18A

3-Bromo-2,5-dimethyl-7-[(2,3,6-trifluorobenzyl)oxy]pyrazolo[1,5-a]pyridine

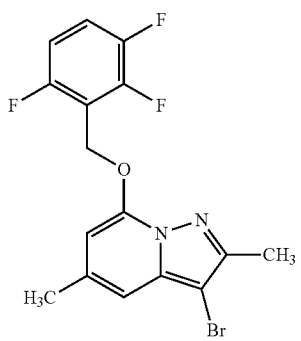 [SMILES: Cc1cc(OCc2c(F)ccc(F)c2F)n2nc(C)c(Br)c2c1]

70 mg (0.84 mmol) of sodium bicarbonate were added to a solution of 103 mg (0.28 mmol) of 2,5-dimethyl-7-[(2,3,6-trifluorobenzyl)oxy]pyrazolo[1,5-a]pyridine-3-carboxylic acid from Example 10A in 1.1 ml of DMF. At RT, a solution of 52 mg (0.29 mmol) of N-bromosuccinimide in 0.75 ml of DMF was, very slowly [2.6 ml/h], added dropwise using a syringe pump. The reaction solution was diluted with dichloromethane and then washed twice with water. The combined aqueous phases were reextracted twice with dichloromethane. The combined organic phases were dried over sodium sulfate, filtered and concentrated. The residue was stirred with water, and the solid obtained was filtered off and dried under high vacuum. 65 mg of the title compound were isolated (43% of theory; 71% purity).

LC-MS (Method 2): R$_t$=1.29 min

MS (ESpos): m/z=385 (M+H)$^+$

Example 19A

3-Bromo-2-cyclopropyl-7-[(2,6-difluorobenzyl)oxy]-5-methylpyrazolo[1,5-a]pyridine

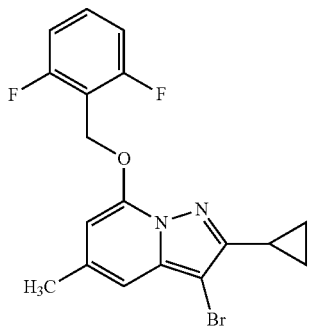 [SMILES: Cc1cc(OCc2c(F)cccc2F)n2nc(C3CC3)c(Br)c2c1]

1.79 g (21.35 mmol) of sodium bicarbonate were added to a solution of 3.0 g (6.2 mmol; purity 74%) of 2-cyclopropyl-7-[(2,6-difluorobenzyl)oxy]-5-methylpyrazolo[1,5-a]pyridine-3-carboxylic acid from Example 12A in 28.4 ml of DMF. At RT, a solution of 1.10 g (6.2 mmol) of N-bromosuccinimide in 19 ml of DMF was, very slowly [2.6 ml/h], added dropwise using a syringe pump. The reaction solution was diluted with dichloromethane and then washed twice with water. The combined aqueous phases were reextracted twice with dichloromethane. The combined organic phases were dried over sodium sulfate, filtered and concentrated. The residue was stirred with water, and the solid obtained was filtered off and dried under high vacuum. 2.70 g of the title compound was isolated (98% of theory; 90% purity).

LC-MS (Method 15): $R_t$=1.64 min
MS (ESpos): m/z=393 (M+H)$^+$

Example 20A

3-Bromo-8-[(2,6-difluorobenzyl)oxy]-2,6-dimethyl-imidazo[1,2-a]pyrazine

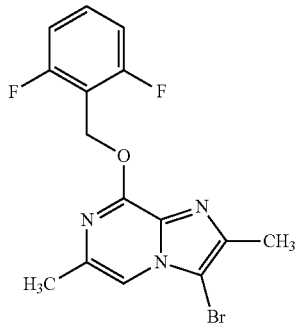 [SMILES: Cc1cn2c(Br)c(C)nc2c(OCc2c(F)cccc2F)n1]

91 mg (1.08 mmol) of sodium bicarbonate were added to a solution of 120 mg (0.32 mmol, purity 90%) of 8-[(2,6-difluorobenzyl)oxy]-2,6-dimethylimidazo[1,2-a]pyrazine-3-carboxylic acid from Example 15A in 1.4 ml of DMF. At RT, a solution of 57 mg (0.32 mmol) of N-bromosuccinimide in 1.0 ml of DMF was added dropwise over 40 min, and stirring of the mixture was continued at RT for 5 min. The reaction solution was diluted with dichloromethane and then washed twice with water. The combined aqueous phases were reextracted twice with dichloromethane. The combined organic phases were concentrated. The residue was stirred with water, and the solid obtained was filtered off and dried under high vacuum. 118 mg of the title compound were isolated (98% of theory).

LC-MS (Method 2): $R_t$=1.21 min
MS (ESpos): m/z=368 (M+H)$^+$
$^1$H-NMR (400 Mhz, DMSO-$d_6$): δ [ppm]=2.30 (s, 3H), 2.39 (s, 3H), 5.55 (s, 2H), 7.17-7.24 (m, 2H), 7.52-7.62 (m, 1H), 7.84 (s, 1H).

Example 21A

7-[(2,6-Difluorobenzyl)oxy]-2,5-dimethyl-3-[1-(2-methyl-2-nitropropyl)-1H-pyrazol-4-yl]pyrazolo[1,5-a]pyridine

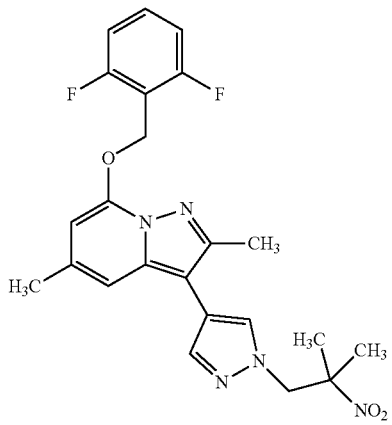 [SMILES: Cc1cc(OCc2c(F)cccc2F)n2nc(C)c(-c3cnn(CC(C)(C)[N+](=O)[O-])c3)c2c1]

40 mg (0.11 mmol) of 7-[(2,6-difluorobenzyl)oxy]-2,5-dimethyl-3-(1H-pyrazol-4-yl)pyrazolo[1,5-a]pyridine from Example 1 were initially charged in 0.65 ml of DMF, 41 mg (0.13 mmol) of caesium carbonate and 89 mg (0.32 mmol) of 2-methyl-2-nitropropyl trifluoromethanesulphonate Example 16A were added and the mixture was stirred at RT for 2 h. Another 89 mg (0.32 mmol) of 2-methyl-2-nitropropyl trifluoromethanesulphonate were then added and the mixture was stirred at RT for 1 h. Once more, 21 mg (0.06 mmol) of caesium carbonate and 89 mg (0.32 mmol) of 2-methyl-2-nitropropyl trifluoromethanesulphonate were added, and the mixture was stirred at RT overnight. Acetonitrile/water/TFA was added and the reaction mixture was purified by preparative HPLC (RP18 column, mobile phase: acetonitrile/water gradient with addition of 0.1% TFA). This gave 28 mg of the target compound (58% of theory).

LC-MS (Method 2): $R_t$=1.15 min
MS (ESpos): m/z=456 (M+H)$^+$

Example 22A

Ethyl 7-(cyclohexylmethoxy)-2,5-dimethylpyrazolo[1,5-a]pyridine-3-carboxylate

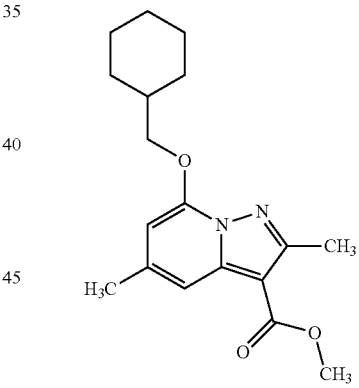

0.5 g (2.13 mmol) of ethyl 7-hydroxy-2,5-dimethylpyrazolo[1,5-a]pyridine-3-carboxylate from Example 8A, 416 mg (2.35 mmol) of (bromomethyl)cyclohexane and 1.53 g (4.70 mmol) of caesium carbonate were initially charged in 31 ml of DMF, and the mixture was stirred at 100° C. overnight. The reaction mixture was poured into 260 ml of water. The precipitate was filtered off. This gave 196 mg of the target compound (28% of theory). The aqueous phase was extracted three times with ethyl acetate. The combined organic phases were dried over sodium sulfate, filtered and concentrated. This gave another 425 mg of the target compound (55% of theory; purity 92%).

LC-MS (Method 2): $R_t$=1.33 min
MS (ESpos): m/z=331 (M+H)$^+$

Example 23A 7-(Cyclohexylmethoxy)-2,5-dimethylpyrazolo[1,5-a]pyridine-3-carboxylic acid

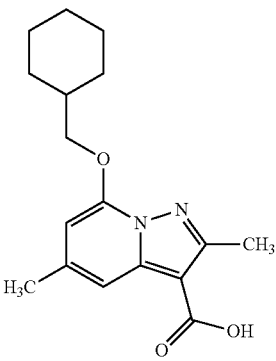

425 mg (1.18 mmol; purity 92%) of ethyl 7-(cyclohexylmethoxy)-2,5-dimethylpyrazolo[1,5-a]pyridine-3-carboxylate from Example 22A were initially charged in 12.3 ml of dioxane, and the mixture was heated to 90° C. 9.47 ml (9.47 mmol) of aqueous 1N sodium hydroxide solution were added and the reaction mixture was stirred at 90° C. for 8 h. The reaction solution was cooled and adjusted to pH 2 with 2N aqueous hydrochloric acid. The mixture was stirred at RT for 30 min. The suspension was filtered, and the solids filtered off were washed with a little water and dried under high vacuum. 10 ml of acetonitrile were added to the solid, the mixture was stirred and the solid was filtered off and dried under high vacuum. This gave 178 mg of the target compound (50% of theory).

LC-MS (Method 2): $R_t$=1.08 min
MS (ESpos): m/z=303 (M+H)$^+$

Example 24A

3-Bromo-7-(cyclohexylmethoxy)-2,5-dimethylpyrazolo[1,5-a]pyridine

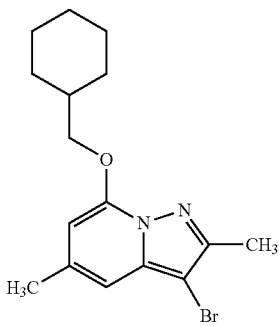

148 mg (1.77 mmol) of sodium bicarbonate were added to a mixture of 178 mg (0.59 mmol) of 7-(cyclohexylmethoxy)-2,5-dimethylpyrazolo[1,5-a]pyridine-3-carboxylic acid from Example 23A in 2.34 ml of DMF. At RT, a solution of 105 mg (0.59 mmol) of N-bromosuccinimide in 1.56 ml of DMF was, very slowly [2.6 ml/h], added dropwise using a syringe pump. Subsequently, once more a solution of 5.3 mg (0.029 mmol) of N-bromosuccinimide in 77 µl of DMF was, very slowly, added to the reaction solution over 75 min. The mixture was stirred at RT for 30 min, diluted with dichloromethane and then washed twice with water. The combined aqueous phases were reextracted twice with dichloromethane. The combined organic phases were dried over sodium sulphate, filtered and concentrated by rotary evaporation. The residue was stirred with water, and the solid obtained was filtered off and dried under high vacuum. 179 mg of the title compound were isolated (78% of theory; 87% purity).

LC-MS (Method 2): $R_t$=1.47 min
MS (ESpos): m/z=337 (M+H)$^+$

Example 25A

7-[(2,6-Difluorobenzyl)oxy]-2,5-dimethylpyrazolo[1,5-a]pyridine-3-carboxamide

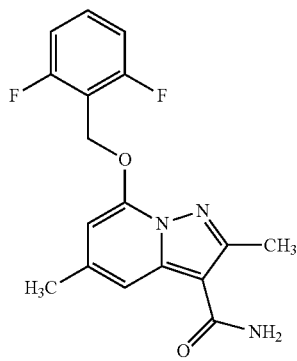 [SMILES: Cc1cc(OCc2c(F)cccc2F)n2nc(C)c(C(N)=O)c2c1]

Under argon, 0.80 g (2.19 mmol, purity 91%) of 7-[(2,6-difluorobenzyl)oxy]-2,5-dimethylpyrazolo[1,5-a]pyridine-3-carboxylic acid from Example 4A in 24 ml of DMF/dichloroethane (1/1) were initially charged, and 546 mg (2.85 mmol) of 1-(3-dimethylaminopropyl)-3-ethylcarbodiimide hydrochloride and 436 mg (2.85 mmol) of 1-hydroxy-1H-benzotriazole hydrate (HOBT) were added successively at RT and the mixture was stirred at RT for 10 min. 586 mg (10.95 mmol) of ammonium chloride and 2.67 ml (15.34 mmol) of N,N-diisopropylethylamine were then added, and the mixture was stirred at RT for 10 min and at 40° C. for 10 min. Subsequently, another 126 mg (0.66 mmol) of 1-(3-dimethylaminopropyl)-3-ethylcarbodiimide hydrochloride and 101 mg (0.66 mmol) of 1-hydroxy-1H-benzotriazole hydrate (HOBT) were added, and the mixture was stirred at 40° C. for 30 min. The mixture was concentrated, water was added to the residue and the mixture was stirred for 1 h. The solid formed was dried under reduced pressure. This gave 721 mg (84% of theory; purity 85%) of the title compound which was reacted further without purification.

LC-MS (Method 15): $R_t$=1.05 min
MS (ESpos): m/z=332 (M+H)$^+$

Example 26A

7-[(2,6-Difluorobenzyl)oxy]-2,5-dimethylpyrazolo[1,5-a]pyridine-3-carbonitrile

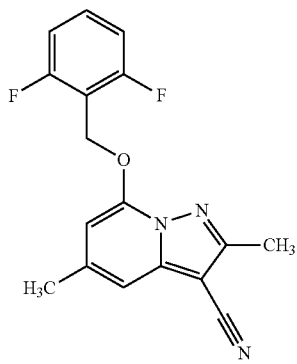 [SMILES: Cc1cc(OCc2c(F)cccc2F)n2nc(C)c(C#N)c2c1]

721 mg (1.85 mmol; purity 85%) of 7-[(2,6-difluorobenzyl)oxy]-2,5-dimethylpyrazolo[1,5-a]pyridine-3-carboxamide from Example 25A were initially charged in 8.6 ml of THF, and 0.39 ml (4.81 mmol) of pyridine was added. 0.68 ml (4.81 mmol) of trifluoroacetic anhydride were then added dropwise, and the mixture was stirred at RT for 5 h. The mixture was then added to water and stirred at RT for 30 min. The resulting solid was filtered off, washed with water and dried under reduced pressure. This gave 605 mg (87% of theory; purity 83%) of the title compound.

LC-MS (Method 2): $R_t$=1.09 min
MS (ESpos): m/z=314 (M+H)$^+$

Example 27A

7-[(2,6-Difluorobenzyl)oxy]-N-hydroxy-2,5-dimethylpyrazolo[1,5-a]pyridine-3-carboximidamide

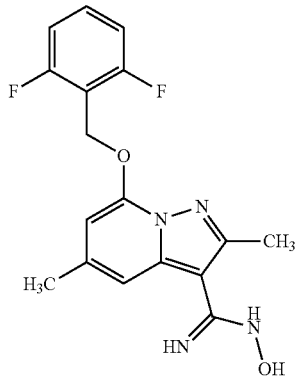 [SMILES: Cc1cc(OCc2c(F)cccc2F)n2nc(C)c(C(=N)NO)c2c1]

250 mg (0.66 mmol; purity 83%) of 7-[(2,6-difluorobenzyl)oxy]-2,5-dimethylpyrazolo[1,5-a]pyridine-3-carbonitrile from Example 26A were suspended in 9.2 ml of ethanol, 368 mg (5.3 mmol) of hydroxylamine hydrochloride and 0.74 ml (5.3 mmol) of triethylamine were added and the mixture was stirred at 80° C. overnight. The mixture was then concentrated under reduced pressure, 8.9 of water and 0.45 ml of ethanol were added and the mixture was stirred for 1 h. The solid formed was filtered off, washed with 2.2 ml of water and dried under high vacuum. The residue was taken up in acetonitrile, water and trifluoroacetic acid were added and the mixture was purified by preparative HPLC (RP18 column, mobile phase: acetonitrile/water gradient with addition of 0.1% TFA). 73 mg (31% of theory) of the title compound were obtained.

LC-MS (Method 2): $R_t$=0.62 min
MS (ESpos): m/z=347 (M+H)$^+$

Example 28A

7-[(2,6-Difluorobenzyl)oxy]-2,5-dimethylpyrazolo[1,5-a]pyridine-3-carboximidamide acetate

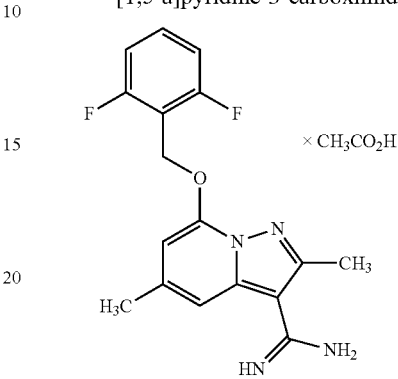

73 mg (0.21 mmol) of 7-[(2,6-difluorobenzyl)oxy]-N-hydroxy-2,5-dimethylpyrazolo[1,5-a]pyridine-3-carboximidamide from Example 27A were initially charged in 2.1 ml of acetic acid, and 23.4 µl (0.25 mmol) of acetic anhydride were added. 16 mg of palladium/carbon (10%, moist) were then added, and the mixture was hydrogenated at atmospheric pressure for 5 h. The mixture was filtered through a Millipore filter and washed with ethyl acetate. After concentration, twice in each case 2 ml of toluene were added to the residue, and the mixture was concentrated under reduced pressure. The residue was dried under high vacuum. This gave 65 mg (73% of theory; purity 91%) of the title compound.

LC-MS (Method 2): $R_t$=0.62 min
MS (ESpos): m/z=331 (M-CH$_3$CO$_2$H+H)$^+$

Example 29A

2-{7-[(2,6-Difluorobenzyl)oxy]-2,5-dimethylpyrazolo[1,5-a]pyridin-3-yl}-4-iodo-5,5-dimethyl-5,7-dihydro-6H-pyrrolo[2,3-d]pyrimidin-6-one

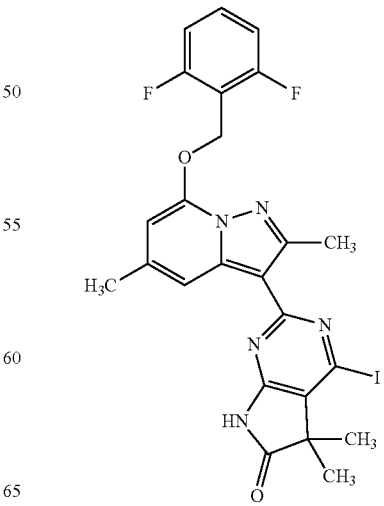

Under argon, 70 mg (0.12 mmol) of 4-amino-2-{7-[(2,6-difluorobenzyl)oxy]-2,5-dimethylpyrazolo[1,5-a]pyridin-3-yl}-5,5-dimethyl-5,7-dihydro-6H-pyrrolo[2,3-d]pyrimidin-6-one trifluoroacetate from Example 34 were initially charged in 1.5 ml of abs. dioxane, at RT, 59 μl (0.74 mmol) of diiodomethane, 121 mg (1.03 mmol) of isopentyl nitrite and 200 mg of 4 A molecular sieve were added and the mixture was stirred at 85° C. overnight. The reaction mixture was subsequently filtered, the residue (molecular sieve) was rinsed with ethyl acetate and the solvent was evaporated. The residue was then diluted with acetonitrile/water, and a little TFA was added. The solution was purified by preparative HPLC (RP18 column, mobile phase: acetonitrile/water gradient with addition of 0.1% TFA). The product fractions were concentrated, saturated sodium bicarbonate solution was added and the mixture was extracted three times with ethyl acetate. The solvent was removed on a rotary evaporator. 23 mg (31% of theory) of the title compound were obtained.

LC-MS (Method 16): $R_t$=2.48 min
MS (ESpos): m/z=576 (M+H)$^+$

WORKING EXAMPLES

Example 1

7-[(2,6-Difluorobenzyl)oxy]-2,5-dimethyl-3-(1H-pyrazol-4-yl)pyrazolo[1,5-a]pyridine

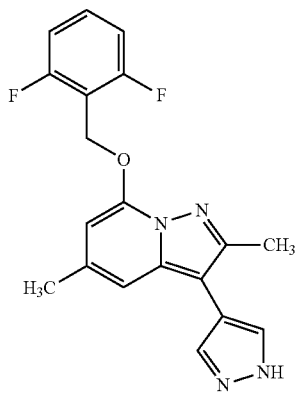 [SMILES: Cc1cc(OCc2c(F)cccc2F)n2nc(C)c(-c3cn[nH]c3)c2c1]

1.0 g (2.64 mmol) of 3-bromo-7-[(2,6-difluorobenzyl)oxy]-2,5-dimethylpyrazolo[1,5-a]pyridine from Example 17A and 1.17 g (3.96 mmol) of tert-butyl 4-(4,4,5,5-tetramethyl-1,3,2-dioxaborolan-2-yl)-1H-pyrazole-1-carboxylate were initially charged in 32 ml of abs. acetonitrile and gassed with argon. 104 mg (0.13 mmol) of chloro(2-dicyclohexylphosphino-2',4',6'-triisopropyl-1,1'-biphenyl)[2-(2'-amino-1,1'-biphenyl)palladium (II) [CAS: 1310584-14-5] were then added, followed by 15.9 ml (7.93 mmol) of aqueous 0.5 M potassium phosphate solution (oxygen-free). The reaction mixture was stirred vigorously at 60° C. for 12 h. Another 583 mg (1.98 mmol) of tert-butyl 4-(4,4,5,5-tetramethyl-1,3,2-dioxaborolan-2-yl)-1H-pyrazole-1-carboxylate and 104 mg (0.13 mmol) of chloro(2-dicyclohexylphosphino-2',4',6'-triisopropyl-1,1'-biphenyl)[2-(2'-amino-1,1'-biphenyl)palladium (II) [CAS: 1310584-14-5] were added. The reaction mixture was stirred vigorously at 60° C. for 5 h. The reaction solution was cooled, dichloromethane was added and the mixture was washed three times with water. The combined aqueous phases were reextracted twice with dichloromethane. The combined organic phases were dried over sodium sulphate, filtered and concentrated. The residue was purified in several portions by preparative HPLC (RP18 column, mobile phase: acetonitrile/water gradient with addition of 0.1% TFA). The product-containing fractions were concentrated, the residue was taken up in dichloromethane and a little methanol and washed twice with aqueous saturated sodium bicarbonate solution. The combined aqueous phases were reextracted twice with dichloromethane. The combined organic phases were dried over sodium sulfate, filtered and concentrated. This gave 231 mg (19% of theory) of the title compound.

LC-MS (Method 2): $R_t$=0.87 min
MS (ESpos): m/z=355 (M+H)$^+$
$^1$H-NMR (500 Mhz, DMSO-d$_6$): δ [ppm]=2.34-2.40 (m, 6H), 5.43 (s, 2H), 6.38 (s, 1H), 7.13 (s, 1H), 7.22-7.30 (m, 2H), 7.57-7.67 (m, 1H), 7.76 (br. s, 1H), 7.98 (br. s, 1H), 12.98 (br. s, 1H).

The example compounds shown in Table 1 were prepared analogously to Example 1 by reacting 3-bromo-7-[(2,6-difluorobenzyl)oxy]-2,5-dimethylpyrazolo[1,5-a]pyridine from Example 17A with the appropriate boronic acids or boronic esters, commercially available or known from the literature (1.5-2.5 equivalents), aqueous potassium phosphate solution (3 equivalents) and chloro(2-dicyclohexylphosphino-2',4',6'-triisopropyl-1,1'-biphenyl)[2-(2'-amino-1,1'-biphenyl)palladium (II) [CAS: 1310584-14-5] (0.05-0.1 equivalents) under the reaction conditions described (solvent: acetonitrile; reaction time: 4-24 h; temperature: 60° C.).

In general, at the start of the reaction 0.05 equivalents of chloro(2-dicyclohexylphosphino-2',4',6'-triisopropyl-1,1'-biphenyl)[2-(2'-amino-1,1'-biphenyl)palladium (II) [CAS: 1310584-14-5] and 1.5 equivalents of boronic acid or boronic ester were used. In the case of incomplete conversion, another 0.05 equivalents of chloro(2-dicyclohexylphosphino-2',4',6'-triisopropyl-1,1'-biphenyl)[2-(2'-amino-1,1'-biphenyl)palladium (II) [CAS: 1310584-14-5] and 1.0 equivalents of boronic acid or boronic ester were added to the reaction mixture.

Exemplary Work-Up of the Reaction Mixture:

The reaction solution was cooled, water and dichloromethane (or ethyl acetate) was added and the mixture was washed three times with water. The combined aqueous phases were reextracted twice with dichloromethane (or ethyl acetate). The combined organic phases were dried over sodium sulphate, filtered and concentrated. The residue was purified by preparative HPLC (RP18 column, mobile phase: acetonitrile/water gradient with addition of 0.1% TFA). The product-containing fractions were concentrated, the residue was taken up in dichloromethane and a little methanol and washed twice with aqueous saturated sodium bicarbonate solution. The combined aqueous phases were reextracted twice with dichloromethane. The combined organic phases were dried over sodium sulphate, filtered and concentrated.

The crude product was optionally purified again by thick-layer chromatography (solvent: dichloromethane/methanol=100/1 or 50/1 or 20/1 or dichloromethane/cyclohexane=10/1).

TABLE 1

| Example No. | IUPAC name (Yield) | Analytical data |
|---|---|---|
| 2 | 1-(3-{7-[(2,6-Difluorobenzyl)oxy]-2,5-dimethylpyrazolo[1,5-a]pyridin-3-yl}phenyl)ethanone | LC-MS (Method 2): R$_t$ = 1.16 min MS (ESpos): m/z = 407 (M + H)$^+$ |

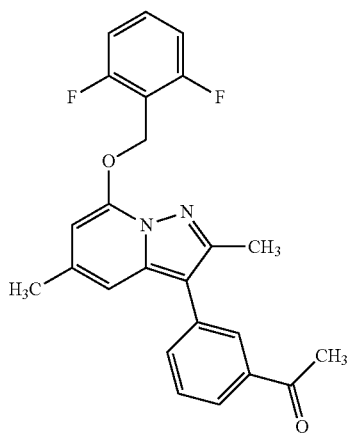 [SMILES: CC(=O)c1cccc(-c2c(C)nn3c(OCc4c(F)cccc4F)cc(C)cc23)c1]

The boronic acid was used.
(62% of theory)

| | 1-(3-{7-[(2,6-Difluorobenzyl)oxy]-2,5-dimethylpyrazolo[1,5-a]pyridin-3-yl}phenyl)acetamide | LC-MS (Method 2): R$_t$ = 1.02 min MS (ESpos): m/z = 422 (M + H)$^+$ |
|---|---|---|
| 3 | | |

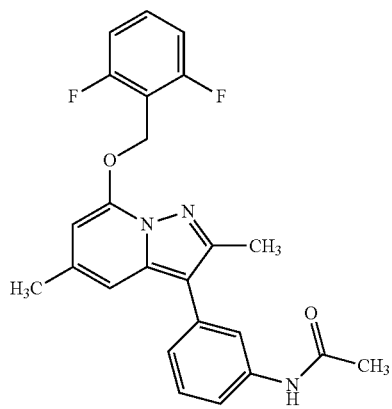 [SMILES: CC(=O)Nc1cccc(-c2c(C)nn3c(OCc4c(F)cccc4F)cc(C)cc23)c1]

The boronic acid was used.
(30% of theory)

TABLE 1-continued

| Example No. | IUPAC name (Yield) | Analytical data |
|---|---|---|
| 4 | 7-[(2,6-Difluorobenzyl)oxy]-2,5-dimethyl-3-[5-(morpholin-4-ylmethyl)-3-thienyl]pyrazolo[1,5-a]pyridine | LC-MS (Method 2): R$_t$ = 0.80 min MS (ESpos): m/z = 470 (M + H)$^+$ $^1$H-NMR (400 Mhz, DMSO-d$_6$) δ = 2.36-2.48 (m, 10H), 3.57-3.65 (m, 4H), 3.73 (s, 2H), 5.43 (s, 2H), 6.42 (s, 1H), 7.13 (s, 1H), 7.20 (s, 1H), 7.22-7.30 (m, 2H), 7.40 (s, 1H), 7.58-7.67 (m, 1H). |

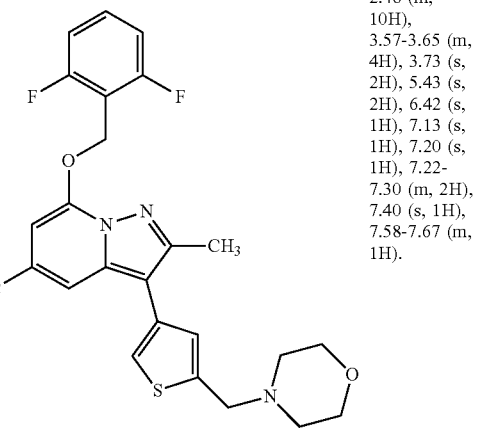

The boronic acid pinacol ester was used.
(58% of theory)

| 5 | 7-[(2,6-Difluorobenzyl)oxy]-2,5-dimethyl-3-{1-[2-(morpholin-4-yl)ethyl]-1H-pyrazol-4-yl}pyrazolo[1,5-a]pyridine | LC-MS (Method 2): R$_t$ = 0.71min MS (ESpos): m/z = 468 (M + H)$^+$ $^1$H-NMR (400 Mhz, DMSO-d$_6$) δ = 2.36-2.48 (m, 10H), 2.70-2.82 (m, 2H), 3.53-3.65 (m, 4H), 4.24-4.34 (m, 2H), 5.43 (s, 2H), 6.38 (s, 1H), 7.13 (s, 1H), 7.22-7.30 (m, 2H), 7.58-7.67 (m, 1H), 7.70 (s, 1H), 8.02 (s, 1H). |
|---|---|---|

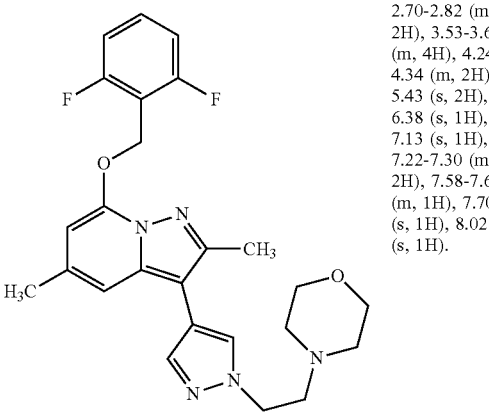

The boronic acid pinacol ester was used.
(38% of theory)

TABLE 1-continued

| Example No. | IUPAC name (Yield) | Analytical data |
|---|---|---|
| 6 | 3-(1-Benzyl-1H-pyrazol-4-yl)-7-[(2,6-difluorobenzyl)oxy]-2,5-dimethylpyrazolo[1,5-a]pyridine | LC-MS (Method 2): $R_t$ = 1.21 min MS (ESpos): m/z = 445 (M + H)+ |

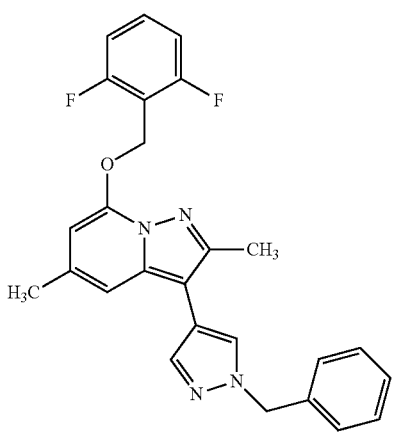 [SMILES: Cc1cc(OCc2c(F)cccc2F)n2nc(C)c(-c3cnn(Cc4ccccc4)c3)c2c1]

The boronic acid pinacol ester was used.
(68% of theory)

| | | |
|---|---|---|
| 7 | 7-[(2,6-Difluorobenzyl)oxy]-3-[3-(ethylsulphonyl)phenyl]-2,5-dimethylpyrazolo[1,5-a]pyridine | LC-MS (Method 2): $R_t$ = 1.14 min MS (ESpos): m/z = 457 (M + H)+ |

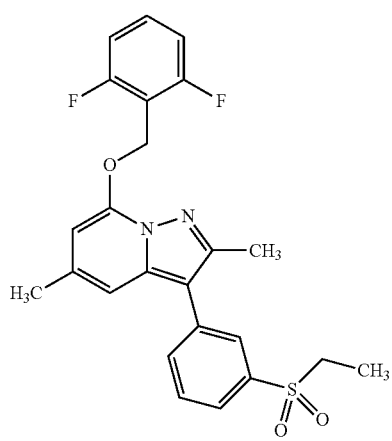 [SMILES: CCS(=O)(=O)c1cccc(-c2c(C)nn3c(OCc4c(F)cccc4F)cc(C)cc23)c1]

The boronic acid was used.
(65% of theory)

TABLE 1-continued

| Example No. | IUPAC name (Yield) | Analytical data |
|---|---|---|
| 8 | 7-[(2,6-Difluorobenzyl)oxy]-3-[1-(4-fluorophenyl)-1H-pyrazol-4-yl]-2,5-dimethylpyrazolo[1,5-a]pyridine | LC-MS (Method 2): $R_t$ = 1.27 min MS (ESpos): m/z = 449 (M + H)+ |

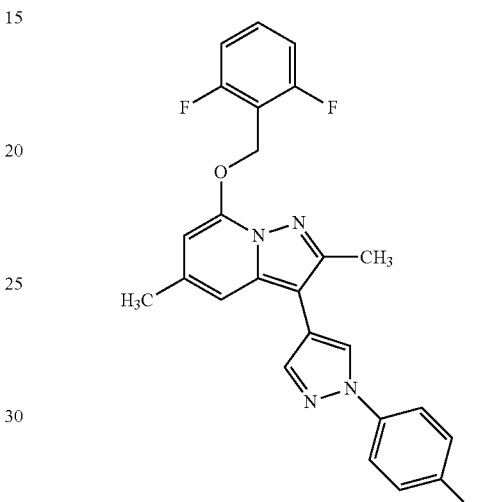

The boronic acid was used.
(18% of theory)

| | | |
|---|---|---|
| 9 | 3-(6-Chloro-5-methylpyridin-3-yl)-7-[(2,6-difluorobenzyl)oxy]-2,5-dimethylpyrazolo[1,5-a]pyridine | LC-MS (Method 2): $R_t$ = 1.30 min MS (ESpos): m/z = 414 (M + H)+ |

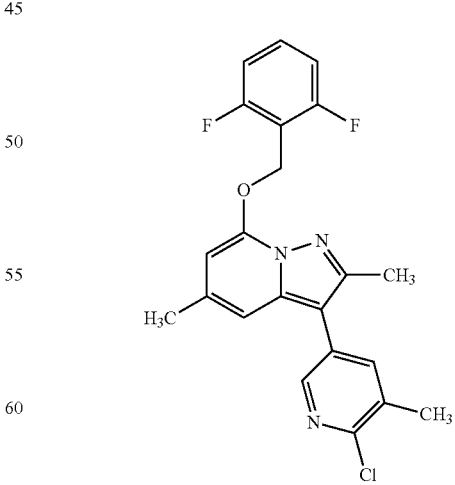

The boronic acid was used.
(4% of theory)

TABLE 1-continued

| Example No. | IUPAC name (Yield) | Analytical data |
|---|---|---|
| 10 | N-(3-{7-[(2,6-Difluorobenzyl)oxy]-2,5-dimethylpyrazolo[1,5-a]pyridin-3-yl}benzyl)-N-methylethanamine | LC-MS (Method 2): $R_t$ = 0.81 min MS (ESpos): m/z = 436 (M + H)⁺ |

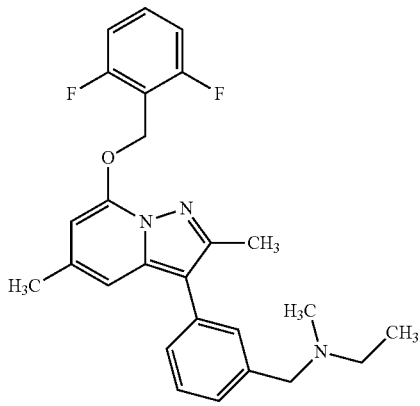 [SMILES: CCN(C)Cc1cccc(-c2c(C)nn3c(OCc4c(F)cccc4F)cc(C)cc23)c1]

The boronic acid was used.
(36% of theory)

| 11 | 7-[(2,6-Difluorobenzyl)oxy]-2,5-dimethyl-3-[3-(pyrrolidin-1-ylmethyl)phenyl]pyrazolo[1,5-a]pyridine | LC-MS (Method 2): $R_t$ = 0.81 min MS (ESpos): m/z = 448 (M + H)⁺ |

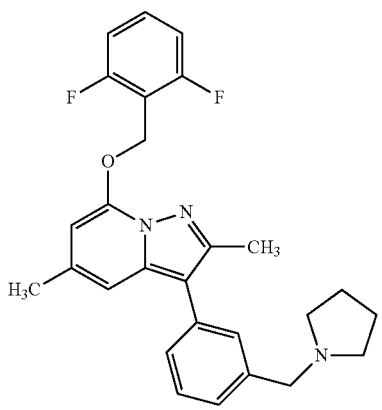 [SMILES: Cc1cc(OCc2c(F)cccc2F)n2nc(C)c(-c3cccc(CN4CCCC4)c3)c2c1]

The boronic acid was used.
(34% of theory)

TABLE 1-continued

| Example No. | IUPAC name (Yield) | Analytical data |
|---|---|---|
| 12 | 3-{7-[(2,6-Difluorobenzyl)oxy]-2,5-dimethylpyrazolo[1,5-a]pyridin-3-yl}benzamide | LC-MS (Method 2): $R_t$ = 0.95 min MS (ESpos): m/z = 408 (M + H)⁺ |

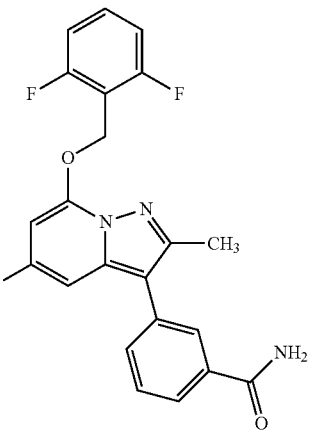

The boronic acid pinacol ester was used.
(49% of theory)

| 13 | N-(3-{7-[(2,6-Difluorobenzyl)oxy]-2,5-dimethylpyrazolo[1,5-a]pyridin-3-yl}phenyl)methansulphonamide | LC-MS (Method 2): $R_t$ = 1.10 min MS (ESpos): m/z = 458 (M + H)⁺ |

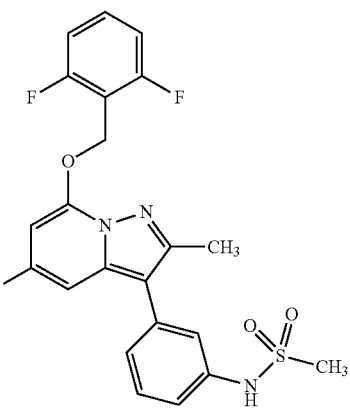

The boronic acid pinacol ester was used.
(24% of theory)

TABLE 1-continued

| Example No. | IUPAC name (Yield) | Analytical data |
|---|---|---|
| 14 | 7-[(2,6-Difluorobenzyl)oxy]-2,5-dimethyl-3-[3-(pyrrolidin-1-yl)phenyl]pyrazolo[1,5-a]pyridine<br><br>The boronic acid was used.<br>(48% of theory) | LC-MS (Method 2):<br>$R_t$ = 1.51 min<br>MS (ESpos):<br>m/z = 434 (M + H)$^+$<br>$^1$H-NMR (500 Mhz, DMSO-$d_6$) δ = 1.94-2.02 (m, 4H), 2.35-2.42 (m, 6H), 3.23-3.33 (m, 4H, superposed by solvent peak), 5.43 (s, 2H), 6.38 (s, 1H), 6.49 (d, 1H), 6.53 (s, 1H), 6.65 (d, 1H), 7.08 (s, 1H), 7.20-7.30 (m, 3H), 7.58-7.67 (m, 1H). |
| 15 | 7-[(2,6-Difluorobenzyl)oxy]-2,5-dimethyl-3-[2-(piperazin-1-yl)pyridin-4-yl]pyrazolo[1,5-a]pyridine<br><br>The boronic acid pinacol ester was used.<br>(33% of theory) | LC-MS (Method 2):<br>$R_t$ = 0.72 min<br>MS (ESpos):<br>m/z = 450 (M + H)$^+$ |

Example 16

1-(4-{7-[(2,6-Difluorobenzyl)oxy]-2,5-dimethylpyrazolo[1,5-a]pyridin-3-yl}-1H-pyrazol-1-yl)-2-methylpropane-2-amine

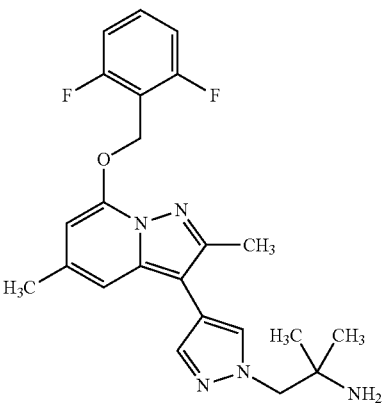 [SMILES: Cc1cc(OCc2c(F)cccc2F)n2nc(C)c(-c3cnn(CC(C)(C)N)c3)c2c1]

About 102 mg of Raney nickel (50% aqueous suspension) were added to 35 mg (0.08 mmol) of 7-[(2,6-difluorobenzyl)oxy]-2,5-dimethyl-3-[1-(2-methyl-2-nitropropyl)-1H-pyrazol-4-yl]pyrazolo[1,5-a]pyridine from Example 21A in 1 ml of ethanol, and the mixture was hydrogenated under atmospheric pressure at room temperature overnight. The reaction mixture was filtered through Celite and the filter cake was washed with dichloromethane and 2 N ammonia solution in methanol. The filtrate was concentrated and the residue was purified by thick-layer chromatography (mobile phase: dichloromethane/2 N ammonia in methanol (45/1)). This gave 20 mg of the target compound (60% of theory).

LC-MS (Method 2): $R_t$=0.72 min
MS (ESpos): m/z=426 (M+H)$^+$
$^1$H-NMR (500 Mhz, DMSO-$d_6$) δ=1.02 (s, 6H), 1.69 (br. s, 2H), 2.36-2.41 (m, 6H), 4.02 (s, 2H), 5.42 (s, 2H), 6.38 (s, 1H), 7.12-7.15 (m, 1H), 7.23-7.30 (m, 2H), 7.59-7.66 (m, 1H), 7.73 (s, 1H), 7.97 (s, 1H).

Example 17

7-[(2,6-Difluorobenzyl)oxy]-3-(2,5-difluoropyridin-4-yl)-2,5-dimethylpyrazolo[1,5-a]pyridine

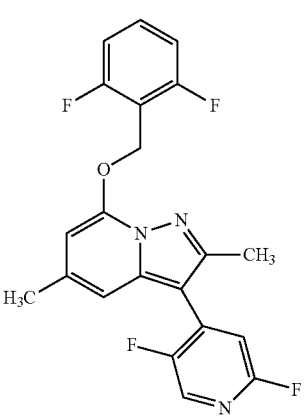 [SMILES: Cc1cc(OCc2c(F)cccc2F)n2nc(C)c(-c3cc(F)ncc3F)c2c1]

Under argon, 79 mg (0.50 mmol) of (2,5-difluoropyridin-4-yl)boric acid, 126 mg (0.59 mmol) of potassium phosphate and 10 mg (0.02 mmol) of bis(tri-tert-butylphosphine)palladium(0) were added in succession to 75 mg (0.20 mmol) of 3-bromo-7-[(2,6-difluorobenzyl)oxy]-2,5-dimethylpyrazolo[1,5-a]pyridine (Example 17A) in a mixture of 1.44 ml of ethanol, 0.72 ml of water and 0.72 ml of toluene. The suspension was degassed with argon and then stirred at 120° C. for 30 min. After the reaction had ended, the reaction mixture was concentrated and the residue was taken up in ethyl acetate/water and extracted. The aqueous phase was extracted twice with ethyl acetate. The combined organic phases were dried over sodium sulphate, filtered, concentrated and dried under high vacuum. The residue was purified by preparative HPLC (RP18 column, mobile phase: acetonitrile/water gradient with addition of 0.1% TFA). The product-containing fractions were concentrated, the residue was taken up in dichloromethane and washed twice with aqueous saturated sodium bicarbonate solution. The combined aqueous phases were reextracted twice with dichloromethane. The combined organic phases were dried over sodium sulfate, filtered and concentrated. This gave 75 mg of the target compound (91% of theory).

LC-MS (Method 2): $R_t$=1.19 min

MS (ESpos): m/z=402 (M+H)$^+$

Example 18

Ethyl 5-{7-[(2,6-difluorobenzyl)oxy]-2,5-dimethylpyrazolo[1,5-a]pyridin-3-yl}nicotinate

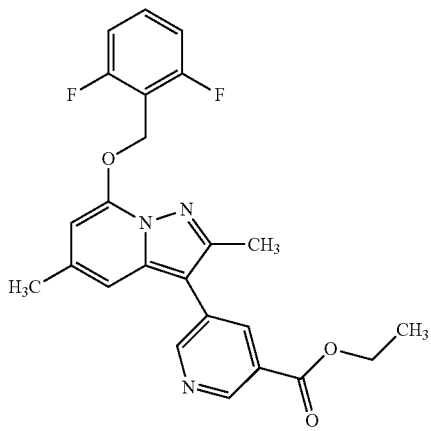 [SMILES: CCOC(=O)c1cncc(-c2c(C)nn3c(OCc4c(F)cccc4F)cc(C)cc23)c1]

Under argon, 60 mg (0.22 mmol) of ethyl 5-(4,4,5,5-tetramethyl-1,3,2-dioxaborolan-2-yl)nicotinate, 92 mg (0.43 mmol) of potassium phosphate and 7 mg (0,014 mmol) of bis(tri-tert-butylphosphine)palladium(0) were added in succession to 53 mg (0.14 mmol) of 3-bromo-7-[(2,6-difluorobenzyl)oxy]-2,5-dimethylpyrazolo[1,5-a]pyridine (Example 17A) in a mixture of 0.26 ml of ethanol, 0.53 ml of water and 0.53 ml of toluene. The suspension was degassed with argon and then stirred at 120° C. for 30 min. After the reaction had ended, the reaction mixture was concentrated and the residue was taken up in ethyl acetate/water and extracted. The aqueous phase was extracted twice with ethyl acetate. The combined organic phases were dried over sodium sulphate, filtered, concentrated and dried under high vacuum. The residue was purified by preparative HPLC (RP18 column, mobile phase: acetonitrile/water gradient with addition of 0.1% TFA). The product-containing fractions were concentrated and purified once more by thick-layer chromatography (mobile phase: dichloromethane/methanol=100/1). This gave 34 mg of the target compound (52% of theory).

LC-MS (Method 2): $R_t$=1.18 min

MS (ESpos): m/z=438 (M+H)$^+$

Example 19

8-[(2,6-Difluorobenzyl)oxy]-2,6-dimethyl-3-(1H-pyrazol-4-yl)imidazo[1,2-a]pyrazine trifluoroacetate

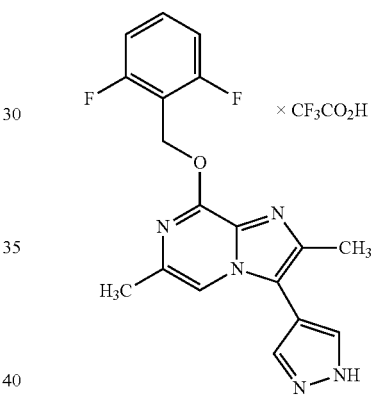

40 mg (0.11 mmol) of 3-bromo-8-[(2,6-difluorobenzyl)oxy]-2,6-dimethylimidazo[1,2-a]pyrazine from Example 20A and 48 mg (0.16 mmol) of tert-butyl 4-(4,4,5,5-tetramethyl-1,3,2-dioxaborolan-2-yl)-1H-pyrazole-1-carboxylate were initially charged in 1.3 ml of abs. acetonitrile and gassed with argon. 4.3 mg (0.01 mmol) of chloro(2-dicyclohexylphosphino-2',4',6'-triisopropyl-1,1'-biphenyl)[2-(2'-amino-1,1'-biphenyl)palladium (II) [CAS: 1310584-14-5] were then added, followed by 0.65 ml (0.33 mmol) of aqueous 0.5 M potassium phosphate solution (oxygen-free). The reaction mixture was stirred at 60° C. overnight. The reaction solution was cooled, TFA was added and the product was purified by preparative HPLC (RP18 column, mobile phase: acetonitrile/water gradient with addition of 0.1% TFA). 2.4 mg (4% of theory, purity 90%) of the title compound were isolated.

LC-MS (Method 2): $R_t$=0.79 min

MS (ESpos): m/z=356 (M-TFA+H)$^+$ $^1$H-NMR (400 Mhz, DMSO-$d_6$): δ [ppm]=2.34-2.40 (m, 6H), 5.57 (s, 2H), 7.17-7.24 (m, 2H), 7.52-7.62 (m, 1H), 7.86 (s, 1H), 7.95-8.15 (m, 2H).

Example 20

6-{8-[(2,6-Difluorobenzyl)oxy]-2,6-dimethylimidazo[1,2-a]pyrazin-3-yl}-1,3,5-triazine-2,4-diamine trifluoroacetate

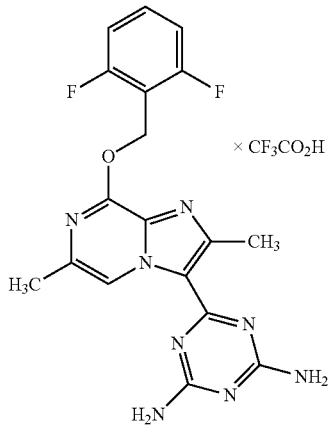 [SMILES: Cc1cn2c(-c3nc(N)nc(N)n3)c(C)nc2c(OCc2c(F)cccc2F)n1]

Under argon, 40 mg (0.29 mmol) of imidodicarbonimidediamide hydrochloride [biguanide hydrochloride] were initially charged in 0.87 ml abs. methanol, 138 mg (0.15 ml, 0.64 mmol) of sodium methoxide (25% in methanol) were added and the mixture was stirred at 50° C. for 30 min. Subsequently, 70 mg (0.19 mmol) of ethyl 8-[(2,6-difluorobenzyl)oxy]-2,6-dimethylimidazo[1,2-a]pyrazine-3-carboxylate from Example 14A were added and the mixture was stirred under reflux overnight. After cooling, water and TFA were added and the mixture was purified by preparative HPLC (RP18 column, mobile phase: acetonitrile/water gradient with addition of 0.1% TFA). The product-containing fractions were concentrated, dissolved in dichloromethane and washed with saturated aqueous sodium bicarbonate solution. The aqueous phase was extracted twice with dichloromethane with addition of a little methanol. The combined organic phases were dried over sodium sulphate and filtered, the filtrate was concentrated and the residue was stirred with water. The precipitate was filtered off with suction and dried under high vacuum. This gave 3.7 mg of the target compound (3.7% of theory).

LC-MS (Method 2): $R_t$=0.85 min
MS (ESpos): m/z=399 (M-TFA+H)$^+$

Example 21

Methyl 3-(4-{7-[(2,6-difluorobenzyl)oxy]-2,5-dimethylpyrazolo[1,5-a]pyridin-3-yl}-1H-pyrazol-1-yl)propanoate trifluoroacetate

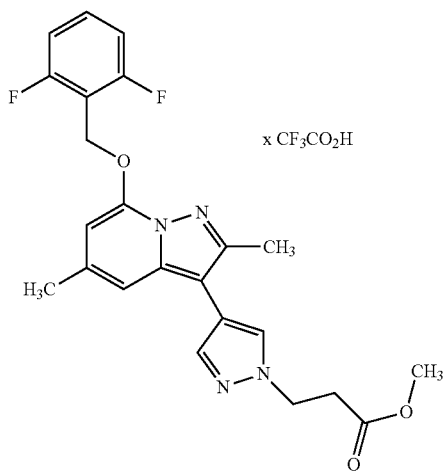 [SMILES: COC(=O)CCn1cc(-c2c(C)nn3c(OCc4c(F)cccc4F)cc(C)cc23)cn1]

202 mg (0.62 mmol) of caesium carbonate, 4 mg (0.02 mmol) of potassium iodide and 52 mg (0.31 mmol) of methyl 3-bromopropanoate were added to 90 mg (0.24 mmol) of 7-[(2,6-difluorobenzyl)oxy]-2,5-dimethyl-3-(1H-pyrazol-4-yl)pyrazolo[1,5-a]pyridine from Example 1 in 1.5 ml of DMF, and the mixture was stirred at 60° C. for 2 h. After cooling, the mixture was purified by preparative HPLC (RP18 column, mobile phase: acetonitrile/water gradient with addition of 0.1% TFA). This gave 71 mg of the target compound (53% of theory).

LC-MS (Method 2): $R_t$=1.04 min
MS (ESpos): m/z=441 (M-TFA+H)$^+$
$^1$H-NMR (400 Mhz, DMSO-$d_6$) δ=2.35-2.43 (m, 6H), 2.94 (t, 2H), 3.62 (s, 3H), 4.41 (t, 2H), 5.42 (s, 2H), 6.38 (s, 1H), 7.14 (s, 1H), 7.26 (t, 2H), 7.57-7.67 (m, 1H), 7.72 (s, 1H), 8.00 (s, 1H).

Example 22

3-(4-{7-[(2,6-Difluorobenzyl)oxy]-2,5-dimethylpyrazolo[1,5-a]pyridin-3-yl}-1H-pyrazol-1-yl)propanoic acid trifluoroacetate

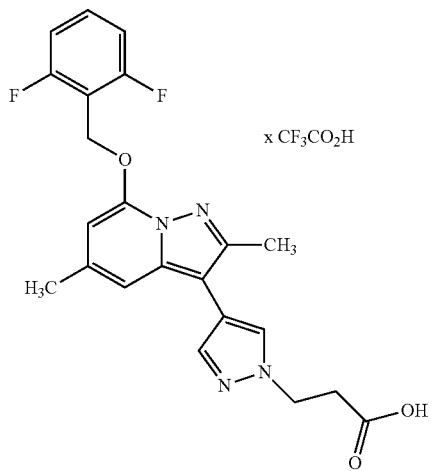 [SMILES: Cc1cc(OCc2c(F)cccc2F)n2nc(C)c(-c3cnn(CCC(=O)O)c3)c2c1]

0.32 ml (0.32 mmol) of 1 N aqueous lithium hydroxide solution was added to 60 mg (0.11 mmol) of methyl 3-(4-{7-[(2,6-difluorobenzyl)oxy]-2,5-dimethylpyrazolo[1,5-a]pyridin-3-yl}-1H-pyrazol-1-yl)propanoate trifluoroacetate from Example 21 in 2.30 ml of THF/methanol (5/1), and the mixture was stirred at room temperature for 2 h. 0.34 ml of 1 N aqueous hydrochloric acid was added and the reaction solution was then purified by preparative HPLC (RP18 column, mobile phase: acetonitrile/water gradient with addition of 0.1% TFA). This gave 52 mg of the target compound (87% of theory).

LC-MS (Method 2): $R_t$=0.92 min
MS (ESpos): m/z=427 (M-TFA+H)$^+$
$^1$H-NMR (400 Mhz, DMSO-$d_6$) δ=2.33-2.42 (m, 6H), 2.86 (t, 2H), 4.37 (t, 2H), 5.41 (s, 2H), 6.38 (s, 1H), 7.14 (s, 1H), 7.27 (t, 2H), 7.57-7.67 (m, 1H), 7.72 (s, 1H), 8.00 (s, 1H), 12.39 (br. s, 1H).

Example 23

N-Cyclopropyl-3-(4-{7-[(2,6-difluorobenzyl)oxy]-2,5-dimethylpyrazolo[1,5-a]pyridin-3-yl}-1H-pyrazol-1-yl)propanamide

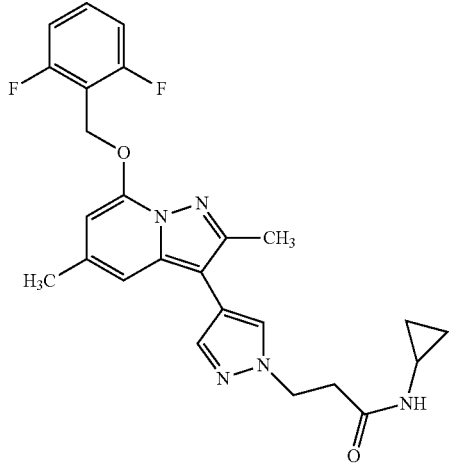 [SMILES: Cc1cc(OCc2c(F)cccc2F)n2nc(C)c(-c3cnn(CCC(=O)NC4CC4)c3)c2c1]

25 mg (0.05 mmol) of 3-(4-{7-[(2,6-difluorobenzyl)oxy]-2,5-dimethylpyrazolo[1,5-a]pyridin-3-yl}-1H-pyrazol-1-yl)propanoic acid trifluoroacetate from Example 22, 23 mg (0.06 mmol) of HATU and 0.04 ml (0.23 mmol) of N,N-diisopropylethylamine in 0.16 ml of DMF were stirred at RT for 20 min, 6 µl (0.09 mmol) of cyclopropylamine were added and the mixture was stirred at RT for 1.5 h. Acetonitrile, water and TFA were added and the reaction solution was purified by preparative HPLC (RP18 column, mobile phase: acetonitrile/water gradient with addition of 0.1% TFA). The product-containing fractions were concentrated, dissolved in dichloromethane and washed twice with saturated aqueous sodium bicarbonate solution. The aqueous phase was extracted twice with dichloromethane. The combined organic phases were dried over sodium sulphate and filtered, and the filtrate was concentrated. This gave 20 mg of the target compound (91% of theory).

LC-MS (Method 2): $R_t$=0.93 min
MS (ESpos): m/z=466 (M+H)$^+$
$^1$H-NMR (500 Mhz, DMSO-d$_6$) δ=0.30-0.36 (m, 2H), 0.57-0.61 (m, 2H), 2.34-2.40 (m, 6H), 2.58-2.67 (m, 3H), 4.38 (t, 2H), 5.42 (s, 2H), 6.38 (s, 1H), 7.12 (s, 1H), 7.25 (t, 2H), 7.58-7.66 (m, 1H), 7.70 (s, 1H), 7.90 (s, 1H), 8.01 (s, 1H).

Example 24

2-(4-{7-[(2,6-Difluorobenzyl)oxy]-2,5-dimethyl-pyrazolo[1,5-a]pyridin-3-yl}-1H-pyrazol-1-yl)ethanol trifluoroacetate

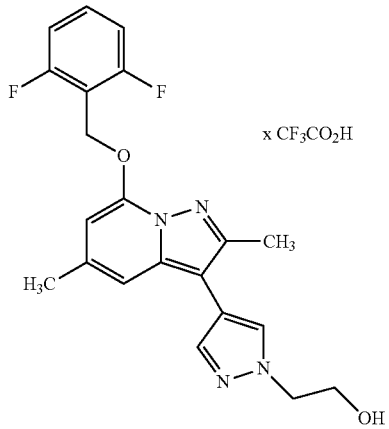 [SMILES: Cc1cc(OCc2c(F)cccc2F)n2nc(C)c(-c3cnn(CCO)c3)c2c1]

98 mg (0.30 mmol) of caesium carbonate, 2 mg (0.01 mmol) of potassium iodide and 0.012 ml (0.15 mmol) of iodoethanol were added to 45 mg (0.12 mmol) of 7-[(2,6-difluorobenzyl)oxy]-2,5-dimethyl-3-(1H-pyrazol-4-yl)pyrazolo[1,5-a]pyridine from Example 1 in 0.63 of DMF, and the mixture was stirred at 70° C. for 1.5 h. Subsequently, another 0.018 ml (0.23 mmol) of iodoethanol were added and the mixture was stirred at 70° C. for 4.5 h. After cooling, water was added and the mixture was extracted three times with ethyl acetate. The combined organic phases were washed with water once. The combined aqueous phases were extracted three times with dichloromethane. The collected organic phases were dried over sodium sulphate, filtered and concentrated. The residue was purified by thick-layer chromatography (solvent: dichloromethane/ethanol=30/1). The product fractions were concentrated and the residue was purified by preparative HPLC (RP18 column, mobile phase: acetonitrile/water gradient with addition of 0.1% TFA). This gave 5 mg of the target compound (8% of theory).

LC-MS (Method 2): $R_t$=0.89 min
MS (ESpos): m/z=399 (M-TFA+H)$^+$

Example 25

7-[(2,6-Difluorobenzyl)oxy]-3-{1-[2-(3,5-dimethyl-1H-pyrazol-4-yl)ethyl]-1H-pyrazol-4-yl}-2,5-dimethylpyrazolo[1,5-a]pyridine

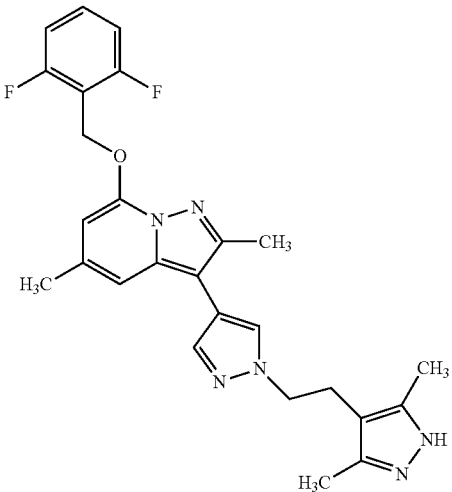 [SMILES: Cc1cc(OCc2c(F)cccc2F)n2nc(C)c(-c3cnn(CCc4c(C)n[nH]c4C)c3)c2c1]

0.08 ml (0.08 mmol) of potassium tert-butoxide solution (1 N in THF) was added to 23 mg (0.06 mmol) of 7-[(2,6-difluorobenzyl)oxy]-2,5-dimethyl-3-(1H-pyrazol-4-yl)pyrazolo[1,5-a]pyridine from Example 1 in 0.3 ml of DMF, the mixture was stirred at room temperature for 5 min, 18 mg (0.09 mmol) of 4-(2-bromoethyl)-3,5-dimethyl-1H-pyrazole and 1 mg (0.01 mmol) of potassium iodide were then added and the mixture was stirred at 70° C. overnight. The reaction mixture was concentrated and the residue was purified by thick-layer chromatography (solvent: dichloromethane/ethanol=20/1).

This gave 10 mg of the target compound (34% of theory).

LC-MS (Method 2): $R_t$=0.88 min
MS (ESpos): m/z=477 (M+H)$^+$

Example 26

N¹-(4-{7-[(2,6-Difluorobenzyl)oxy]-2,5-dimethyl-pyrazolo[1,5-a]pyridin-3-yl}-5-fluoropyridin-2-yl)-2-methylpropane-1,2-diamine trifluoroacetate

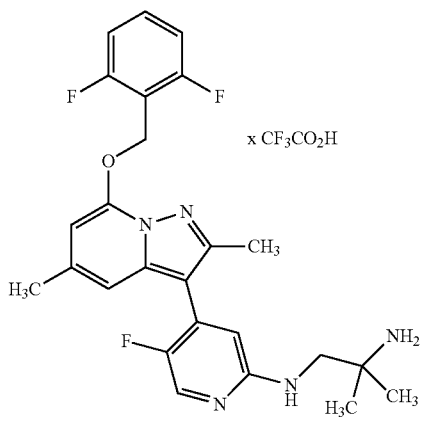 [SMILES: Cc1cc(OCc2c(F)cccc2F)n2nc(C)c(-c3cc(NCC(C)(C)N)ncc3F)c2c1]

35 mg (0.085 mmol) of 7-[(2,6-difluorobenzyl)oxy]-3-(2,5-difluoropyridin-4-yl)-2,5-dimethylpyrazolo[1,5-a]pyridine from Example 17 were initially charged in 0.20 ml of NMP. At room temperature, 89 mg (1.02 mmol) of 2-methylpropane-1,2-diamine were added and the mixture was stirred at 150° C. in a closed vessel in the microwave for 2 h. The reaction solution was diluted with acetonitrile/water, TFA was added and the mixture was purified by preparative HPLC (RP18 column, mobile phase: acetonitrile/water gradient with addition of 0.1% TFA). This gave 2 mg of the target compound (1% of theory).

LC-MS (Method 2): $R_t$=0.61 min

MS (ESpos): m/z=470 (M-TFA+H)⁺

Example 27

5-{7-[(2,6-Difluorobenzyl)oxy]-2,5-dimethylpyrazolo[1,5-a]pyridin-3-yl}nicotinic acid

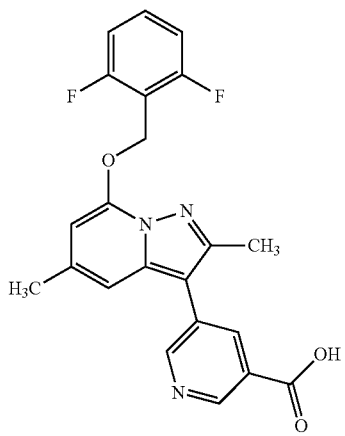 [SMILES: Cc1cc(OCc2c(F)cccc2F)n2nc(C)c(-c3cncc(C(=O)O)c3)c2c1]

0.35 ml (0.35 mmol) of 1N aqueous lithium hydroxide solution were added to 31 mg (0.07 mmol) ethyl 5-{7-[(2,6-difluorobenzyl)oxy]-2,5-dimethylpyrazolo[1,5-a]pyridin-3-yl}nicotinate from Example 18 in 1.5 ml of THF/ethanol (5/1), and the mixture was stirred at room temperature for 4 h. Another 0.35 ml (0.35 mmol) of 1N aqueous lithium hydroxide solution and 0.36 ml of THF/Ethanol (5/1) were added and the mixture was stirred at room temperature overnight. 0.48 ml of THF/Ethanol (5/1) was added and the mixture was stirred at room temperature for another 3 h. With ice cooling, the mixture was adjusted to pH=4 using 1 N aqueous hydrochloric acid solution, and the organic solvent was then removed on a rotary evaporator. The suspension was filtered off, washed with water and dried. 26 mg (87% of theory) of the title compound were obtained.

LC-MS (Method 2): $R_t$=0.90 min

MS (ESpos): m/z=410 (M+H)⁺

Example 28

5-{7-[(2,6-Difluorobenzyl)oxy]-2,5-dimethylpyrazolo[1,5-a]pyridin-3-yl}nicotinamide

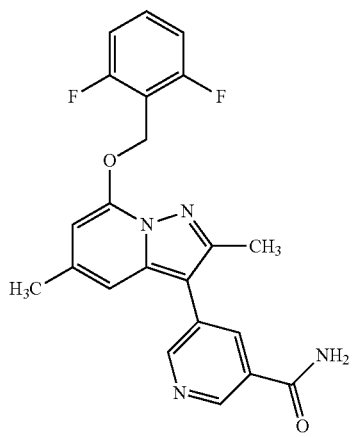 [SMILES: Cc1cc(OCc2c(F)cccc2F)n2nc(C)c(-c3cncc(C(N)=O)c3)c2c1]

15 mg (0.08 mmol) of 1-(3-dimethylaminopropyl)-3-ethylcarbodiimide hydrochloride and 12 mg (0.08 mmol) of 1-hydroxy-1H-benzotriazole hydrate were added to 22 mg (0.05 mmol) of 5-{7-[(2,6-difluorobenzyl)oxy]-2,5-dimethylpyrazolo[1,5-a]pyridin-3-yl}nicotinic acid from Example 27 in 1.0 ml of dichloromethane, and the mixture was stirred at room temperature for 10 min. Subsequently, 14 mg (0.26 mmol) of ammonium chloride and 46 mg (0.36 mmol) of N,N-diisopropylethylamine were added and the mixture was stirred at room temperature overnight. The reaction mixture was concentrated and the residue was purified by thick-layer chromatography (mobile phase: dichloromethane/2 N ammonia in methanol=20/1). 15 mg (70% of theory) of the title compound were obtained.

LC-MS (Method 2): $R_t$=0.82 min

MS (ESpos): m/z=409 (M+H)⁺

¹H-NMR (500 Mhz, DMSO-d₆) δ=2.40 (s, 3H), 2.42 (s, 3H), 5.47 (s, 2H), 6.52 (s, 1H), 7.15 (s, 1H), 7.28 (t, 2H), 7.59-7.69 (m, 2H), 8.23 (br. s, 2H), 8.78 (s, 1H), 8.95 (s, 1H).

Example 29

7-[(2,6-Difluorobenzyl)oxy]-2,5-dimethyl-3-(pyrimidin-5-yl)pyrazolo[1,5-a]pyridine

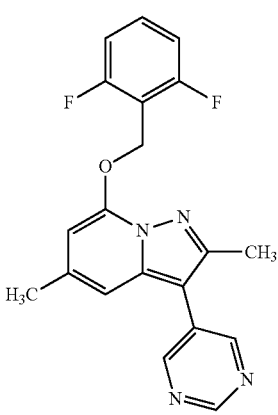

60 mg (0.16 mmol) of 3-bromo-7-[(2,6-difluorobenzyl)oxy]-2,5-dimethylpyrazolo[1,5-a]pyridine from Example 17A and 30 mg (0.24 mmol) of pyrimidin-5-ylboric acid were initially charged in 2 ml of abs. acetonitrile and gassed with argon. 6 mg (0.008 mmol) of chloro(2-dicyclohexylphosphino-2',4',6'-triisopropyl-1,1'-biphenyl)[2-(2'-amino-1,1'-biphenyl)palladium (II) [CAS: 1310584-14-5] were then added, followed by 0.98 ml (0.49 mmol) of aqueous 0.5 M potassium phosphate solution (oxygen-free). The reaction mixture was stirred vigorously at 60° C. for 5 h. The reaction solution was cooled, water was added and the mixture was extracted three times with ethyl acetate. The combined organic phases were washed with water once, dried over sodium sulphate, filtered and concentrated. The residue was dissolved in acetonitrile, water and TFA and purified by preparative HPLC (RP18 column, mobile phase: acetonitrile/water gradient with addition of 0.1% TFA). The product-containing fractions were concentrated, the residue was taken up in dichloromethane and a little methanol and washed twice with aqueous saturated sodium bicarbonate solution. The combined aqueous phases were reextracted twice with dichloromethane. The combined organic phases were dried over sodium sulfate, filtered and concentrated. This gave 6 mg (10% of theory) of the title compound.

LC-MS (Method 2): $R_t$=0.98 min

MS (ESpos): m/z=367 (M+H)$^+$

Example 30

2-Cyclopropyl-7-[(2,6-difluorobenzyl)oxy]-5-methyl-3-{1-[2-(morpholin-4-yl)ethyl]-1H-pyrazol-4-yl}pyrazolo[1,5-a]pyridine

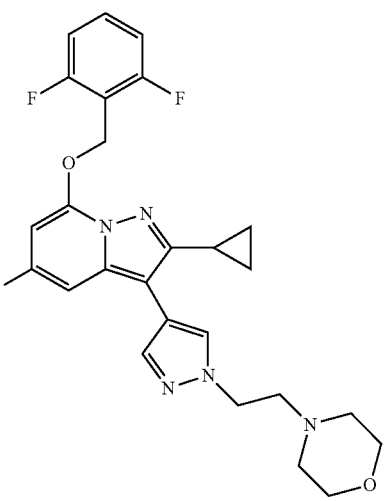

60 mg (0.14 mmol, purity 90%) of 3-bromo-2-cyclopropyl-7-[(2,6-difluorobenzyl)oxy]-5-methylpyrazolo[1,5-a]pyridine from Example 19A and 63 mg (0.21 mmol) of 4-{2-[4-(4,4,5,5-tetramethyl-1,3,2-dioxaborolan-2-yl)-1H-pyrazol-1-yl]ethyl}morpholine were initially charged in 1.7 ml of abs. acetonitrile and gassed with argon. 5.4 mg (0.007 mmol) of chloro(2-dicyclohexylphosphino-2',4',6'-triisopropyl-1,1'-biphenyl)[2-(2'-amino-1,1'-biphenyl)palladium (II) [CAS: 1310584-14-5] were then added, followed by 0.82 ml (0.41 mmol) of aqueous 0.5 M potassium phosphate solution (oxygen-free). The reaction mixture was stirred vigorously at 100° C. for 5 min. The reaction solution was cooled, dissolved in acetonitrile, water and TFA and purified by preparative HPLC (RP18 column, mobile phase: acetonitrile/water gradient with addition of 0.1% TFA). The product-containing fractions were concentrated, the residue was taken up in dichloromethane and a little methanol and washed twice with aqueous saturated sodium bicarbonate solution. The combined aqueous phases were reextracted twice with dichloromethane. The combined organic phases were dried over sodium sulfate, filtered and concentrated. This gave 45 mg (65% of theory) of the title compound.

LC-MS (Method 2): $R_t$=0.82 min

MS (ESpos): m/z=494 (M+H)$^+$

Example 31

2-Cyclopropyl-7-[(2,6-difluorobenzyl)oxy]-5-methyl-3-(1H-pyrazol-4-yl)pyrazolo[1,5-a]pyridine

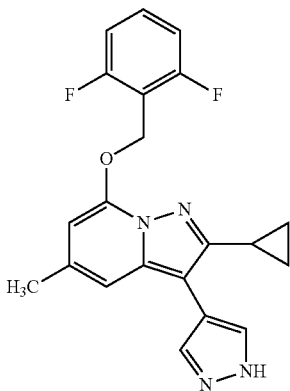 [SMILES: Cc1cc(OCc2c(F)cccc2F)n2nc(C3CC3)c(-c3cn[nH]c3)c2c1]

60 mg (0.14 mmol, purity 90%) of 3-bromo-2-cyclopropyl-7-[(2,6-difluorobenzyl)oxy]-5-methylpyrazolo[1,5-a]pyridine from Example 19A and 61 mg (0.21 mmol) of tert-butyl 4-(4,4,5,5-tetramethyl-1,3,2-dioxaborolan-2-yl)-1H-pyrazol-1-carboxylate were initially charged in 0.8 ml of abs. acetonitrile and gassed with argon. 5.4 mg (0.007 mmol) of chloro(2-dicyclohexylphosphino-2',4',6'-triisopropyl-1,1'-biphenyl)[2-(2'-amino-1,1'-biphenyl)palladium (II) [CAS: 1310584-14-5] were then added, followed by 0.82 ml (0.41 mmol) of aqueous 0.5 M potassium phosphate solution (oxygen-free). The reaction mixture was stirred vigorously at 100° C. for 10 min. The reaction solution was cooled and purified by preparative HPLC (RP18 column; mobile phase: acetonitrile/water gradient with addition of 0.1% TFA). The product-containing fractions were concentrated, the residue was taken up in dichloromethane and washed twice with aqueous saturated sodium bicarbonate solution. The combined aqueous phases were reextracted twice with dichloromethane. The combined organic phases were dried over sodium sulfate, filtered and concentrated. This gave 9 mg of the title compound.

The product-relevant fractions [i.e. the target compound still protected with Boc] from the preparative HPLC were concentrated. 0.1 ml of diethyl ether and 0.2 ml of hydrogen chloride solution (2 N in diethyl ether) were added to the residue, and the mixture was stirred at RT overnight. 1 ml of hydrogen chloride solution (2 N in diethyl ether) was then added, and the mixture was once more stirred at RT overnight. The reaction mixture was purified by preparative HPLC (RP18 column, mobile phase: acetonitrile/water gradient with addition of 0.1% TFA). The product-containing fractions were concentrated, the residue was taken up in dichloromethane and washed twice with aqueous saturated sodium bicarbonate solution. The combined aqueous phases were reextracted twice with dichloromethane. The combined organic phases were dried over sodium sulphate, filtered and concentrated together with the fraction obtained above. This gave 14 mg (26% of theory) of the title compound in total.

LC-MS (Method 2): $R_t$=1.01 min

MS (ESpos): m/z=381 (M+H)$^+$

Example 32

2,5-Dimethyl-3-{1-[2-(morpholin-4-yl)ethyl]-1H-pyrazol-4-yl}-7-[(2,3,6-trifluorobenzyl)oxy]pyrazolo[1,5-a]pyridine trifluoroacetate

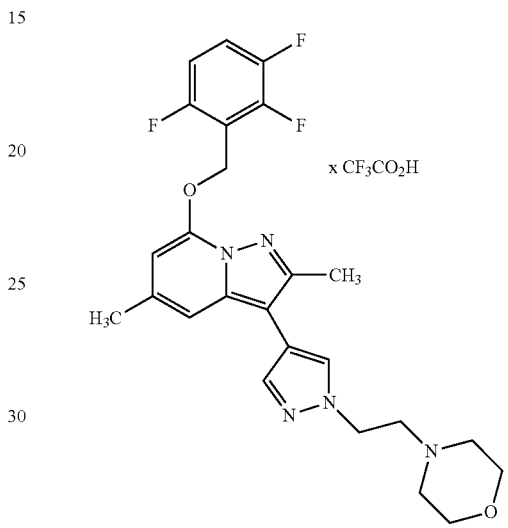

25 mg (0.05 mmol, purity 71%) of 3-bromo-2,5-dimethyl-7-[(2,3,6-trifluorobenzyl)oxy]pyrazolo[1,5-a]pyridine from Example 18A and 21 mg (0.07 mmol) of 4-{2-[4-(4,4,5,5-tetramethyl-1,3,2-dioxaborolan-2-yl)-1H-pyrazol-1-yl]ethyl}morpholine were initially charged in 0.6 ml of abs. acetonitrile and gassed with argon. 2 mg (0.002 mmol) of chloro(2-dicyclohexylphosphino-2',4',6'-triisopropyl-1,1'-biphenyl)[2-(2'-amino-1,1'-biphenyl)palladium (II) [CAS: 1310584-14-5] were then added, followed by 0.28 ml (0.14 mmol) of aqueous 0.5 M potassium phosphate solution (oxygen-free). The reaction mixture was stirred vigorously at 60° C. for 7.5 h. Another 2 mg (0.002 mmol) of chloro(2-dicyclohexylphosphino-2',4',6'-triisopropyl-1,1'-biphenyl)[2-(2'-amino-1,1'-biphenyl)palladium (II) [CAS: 1310584-14-5] and 14 mg (0.05 mmol) of 4-{2-[4-(4,4,5,5-tetramethyl-1,3,2-dioxaborolan-2-yl)-1H-pyrazol-1-yl]ethyl}morpholine were added, and the mixture was stirred at 100° C. for 20 min. The reaction mixture was cooled, water was added and the mixture was extracted three times with ethyl acetate. The combined organic phases were washed with water once, dried over sodium sulphate, filtered and concentrated. The residue was dissolved in acetonitrile, water and TFA and purified by preparative HPLC (RP18 column, mobile phase: acetonitrile/water gradient with addition of 0.1% TFA). This gave 3.5 mg (13% of theory) of the title compound.

LC-MS (Method 2): $R_t$=0.76 min

MS (ESpos): m/z=486 (M-TFA+H)$^+$

Example 33

7-(Cyclohexylmethoxy)-2,5-dimethyl-3-{1-[2-(morpholin-4-yl)ethyl]-1H-pyrazol-4-yl}pyrazolo[1,5-a]pyridine

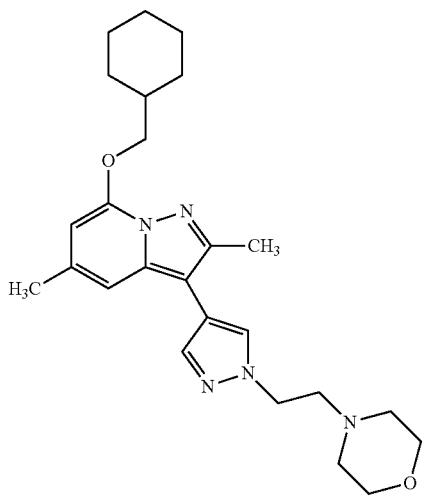 [SMILES: Cc1cc(OCC2CCCCC2)n2nc(C)c(-c3cnn(CCN4CCOCC4)c3)c2c1]

35 mg (0.09 mmol, purity 87%) of 3-bromo-7-(cyclohexylmethoxy)-2,5-dimethylpyrazolo[1,5-a]pyridine from Example 24A and 42 mg (0.14 mmol) of 4-{2-[4-(4,4,5,5-tetramethyl-1,3,2-dioxaborolan-2-yl)-1H-pyrazol-1-yl]ethyl}morpholine were initially charged in 1.1 ml of abs. acetonitrile and gassed with argon. 3.5 mg (0.005 mmol) of chloro(2-dicyclohexylphosphino-2',4',6'-triisopropyl-1,1'-biphenyl)[2-(2'-amino-1,1'-biphenyl)palladium (II) [CAS: 1310584-14-5] were then added, followed by 0.54 ml (0.27 mmol) of aqueous 0.5 M potassium phosphate solution (oxygen-free). The reaction mixture was stirred vigorously at 60° C. overnight. Another 3.5 mg (0.005 mmol) of chloro(2-dicyclohexylphosphino-2',4',6'-triisopropyl-1,1'-biphenyl)[2-(2'-amino-1,1'-biphenyl)palladium (II) [CAS: 1310584-14-5] and 10 mg (0.03 mmol) of 4-{2-[4-(4,4,5,5-tetramethyl-1,3,2-dioxaborolan-2-yl)-1H-pyrazol-1-yl]ethyl}morpholine were then added, and the mixture was stirred vigorously at 100° C. for 25 min. The reaction solution was cooled, water was added and the mixture was extracted three times with ethyl acetate. The combined organic phases were washed with water once, dried over sodium sulphate, filtered and concentrated. The residue was dissolved in acetonitrile, water and TFA and purified by preparative HPLC (RP18 column, mobile phase: acetonitrile/water gradient with addition of 0.1% TFA). The product-containing fractions were concentrated, the residue was taken up in dichloromethane and a little methanol and washed twice with aqueous saturated sodium bicarbonate solution. The combined aqueous phases were extracted twice with dichloromethane. The combined organic phases were dried over sodium sulphate, filtered and concentrated. This gave 22 mg (55% of theory) of the title compound.

LC-MS (Method 2): $R_t$=0.82 min

MS (ESpos): m/z=438 (M+H)$^+$

Example 34

4-Amino-2-{7-[(2,6-difluorobenzyl)oxy]-2,5-dimethylpyrazolo[1,5-a]pyridin-3-yl}-5,5-dimethyl-5,7-dihydro-6H-pyrrolo[2,3-d]pyrimidin-6-one trifluoroacetate

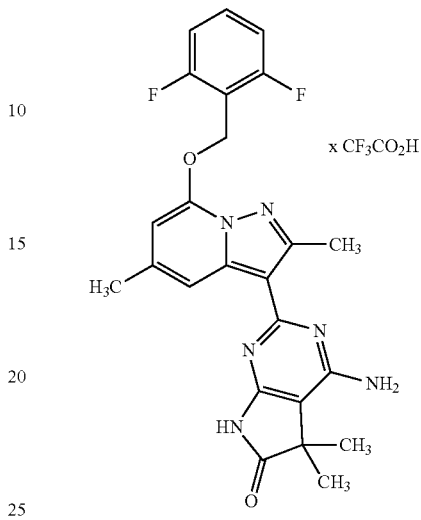

Under argon, 65 mg (0.15 mmol; purity 91%) of 7-[(2,6-difluorobenzyl)oxy]-2,5-dimethylpyrazolo[1,5-a]pyridine-3-carboximidamide acetate from Example 28A were initially charged in 1.7 ml of tert-butanol, 26 mg (0.23 mmol) of potassium tert-butoxide and 38 mg (0.23 mmol) of methyl 3,3-dicyano-2,2-dimethylpropanoate were added in succession at RT and the mixture was heated at reflux overnight. The mixture was then cooled and concentrated. The residue was taken up in acetonitrile, water and trifluoroacetic acid were added and the mixture was purified by preparative HPLC (RP18 column, mobile phase: acetonitrile/water gradient with addition of 0.1% TFA). This gave 19 mg (21% of theory) of the title compound.

LC-MS (Method 2): $R_t$=0.97 min

MS (ESpos): m/z=465 (M-TFA+H)$^+$ $^1$H-NMR (400 Mhz, DMSO-d$_6$) δ=1.32 (s, 6H), 2.44 (s, 3H), 2.68 (s, 3H), 5.43 (s, 2H), 6.38-6.60 (m, 3H), 7.27 (t, 2H), 7.58-7.68 (m, 2H), 8.12 (s, 1H), 10.75 (br. s, 1H).

Example 35

4-[(2-Amino-2-methylpropyl)amino]-2-{7-[(2,6-difluorobenzyl)oxy]-2,5-dimethylpyrazolo[1,5-a]pyridin-3-yl}-5,5-dimethyl-5,7-dihydro-6H-pyrrolo[2,3-d]pyrimidin-6-one

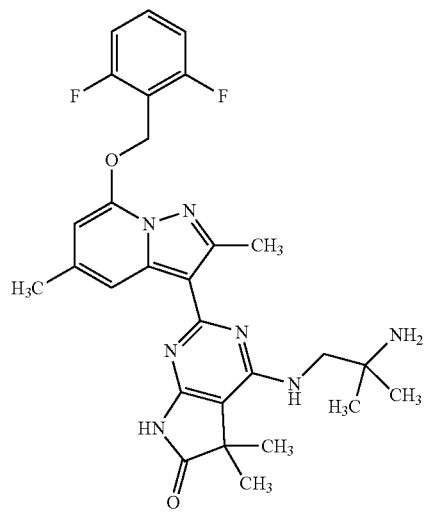 [SMILES: Cc1cc(OCc2c(F)cccc2F)n2nc(C)c(-c3nc(NCC(C)(C)N)c4c(n3)NC(=O)C4(C)C)c2c1]

Under argon, 20 mg (0.035 mmol) of 2-{7-[(2,6-difluorobenzyl)oxy]-2,5-dimethylpyrazolo[1,5-a]pyridin-3-yl}-4-iodo-5,5-dimethyl-5,7-dihydro-6H-pyrrolo[2,3-d]pyrimidin-6-one from Example 29A were initially charged in 0.15 ml of 1-methyl-2-pyrrolidone (NMP), 23 mg (0.26 mmol) of 2-methylpropane-1,2-diamine were added and the mixture was stirred at 120° C. for 135 min. The mixture was then cooled and purified by preparative HPLC (RP18 column, mobile phase: acetonitrile/water gradient with addition of 0.1% TFA). The product fractions were concentrated and the residue was taken up in dichloromethane. The solution was extracted twice with 2 ml of saturated aqueous sodium bicarbonate solution. The organic phase was dried over sodium sulfate, filtered, concentrated and lyophilized. 5.3 mg (28% of theory) of the title compound were obtained.

LC-MS (Method 2): $R_t$=0.81 min
MS (ESpos): m/z=536 (M+H)$^+$

B. ASSESSMENT OF PHARMACOLOGICAL EFFICACY

The following abbreviations are used:

| | |
|---|---|
| ATP | adenosine triphosphate |
| Brij35 | polyoxyethylene(23) lauryl ether |
| BSA | bovine serum albumin |
| DTT | dithiothreitol |
| TEA | triethanolamine |

The pharmacological action of the compounds of the invention can be demonstrated in the following assays:

B-1. Measurement of sGC Enzyme Activity by Means of PPi Detection

Soluble guanylyl cyclase (sGC) converts GTP to cGMP and pyrophosphate (PPi) when stimulated. PPi is detected with the aid of the method described in WO 2008/061626. The signal that arises in the assay increases as the reaction progresses and serves as a measure of the sGC enzyme activity. With the aid of a PPi reference curve, the enzyme can be characterized in a known manner, for example in terms of conversion rate, stimulability or Michaelis constant.

Conduct of the Test

To conduct the test, 29 µl of enzyme solution (0-10 nM soluble guanylyl cyclase (prepared according to Hinicka et al., Journal of Molecular Medicine 77 (1999) 14-23), in 50 mM TEA, 2 mM magnesium chloride, 0.1% BSA (fraction V), 0.005% Brij 35, pH 7.5) were initially charged in the microplate, and 1 µl of the stimulator solution (0-10 µM 3-morpholinosydnonimine, SIN-1, Merck in DMSO) was added. The microplate was incubated at RT for 10 min. Then 20 µl of detection mix (1.2 nM Firefly Luciferase (*Photinus pyralis* luciferase, Promega), 29 µM dehydroluciferin (prepared according to Bitler & McElroy, Arch. Biochem. Biophys. 72 (1957) 358), 122 µM luciferin (Promega), 153 µM ATP (Sigma) and 0.4 mM DTT (Sigma) in 50 mM TEA, 2 mM magnesium chloride, 0.1% BSA (fraction V), 0.005% Brij 35, pH 7.5) were added. The enzyme reaction was started by adding 20 µl of substrate solution (1.25 mM guanosine 5'-triphosphate (Sigma) in 50 mM TEA, 2 mM magnesium chloride, 0.1% BSA (fraction V), 0.005% Brij 35, pH 7.5) and analysed continuously in a luminometer.

B-2. Effect on a Recombinant Guanylate Cyclase Reporter Cell Line

The cellular activity of the compounds according to the invention is determined using a recombinant guanylate cyclase reporter cell line, as described in F. Wunder et al., *Anal. Biochem.* 339, 104-112 (2005).

Representative MEC values (MEC=minimum effective concentration) for the compounds of the invention are shown in the table below (in some cases as mean values from individual determinations):

TABLE A

| Example | MEC [µM] |
|---|---|
| 1 | 0.03 |
| 2 | 0.53 |
| 3 | 0.065 |
| 4 | 0.07 |
| 5 | 0.07 |
| 6 | 0.1 |
| 7 | 0.065 |
| 8 | 1.0 |
| 9 | 3.0 |
| 10 | 0.065 |
| 11 | 0.03 |
| 12 | 0.055 |
| 13 | 0.1 |
| 14 | 2.0 |
| 15 | 0.3 |
| 16 | 0.1 |
| 17 | 2.0 |
| 18 | 10.0 |
| 19 | 0.3 |
| 20 | 2.0 |
| 21 | 0.03 |
| 22 | 0.10 |
| 23 | 0.03 |
| 24 | 0.065 |
| 25 | 0.065 |
| 27 | 2.0 |
| 28 | 0.03 |
| 29 | 0.30 |
| 30 | 0.01 |
| 31 | 0.03 |
| 32 | 0.10 |
| 33 | 0.10 |
| 34 | 1.0 |
| 35 | 3.0 |

B-3. Vasorelaxant Effect In Vitro

Rabbits are stunned by a blow to the neck and exsanguinated. The aorta is removed, freed from adhering tissue and divided into rings of width 1.5 mm, which are placed individually under prestress into 5 ml organ baths with carbogen-sparged Krebs-Henseleit solution at 37° C. having the following composition (each in mM): sodium chloride: 119; potassium chloride: 4.8; calcium chloride dihydrate: 1; magnesium sulfate heptahydrate: 1.4; potassium dihydrogenphosphate: 1.2; sodium bicarbonate: 25; glucose: 10. The contractile force is determined with Statham UC2 cells, amplified and digitalized using A/D transducers (DAS-1802 HC, Keithley Instruments Munich), and recorded in parallel on linear recorders. To generate a contraction, phenylephrine is added to the bath cumulatively in increasing concentration. After several control cycles, the substance to be studied is added in increasing dosage each time in every further run, and the magnitude of the contraction is compared with the magnitude of the contraction attained in the last preceding run. This is used to calculate the concentration needed to reduce the magnitude of the control value by 50% ($IC_{50}$ value). The standard administration volume is 5 µl; the DMSO content in the bath solution corresponds to 0.1%.

B-4. Blood Pressure Measurement on Anaesthetized Rats

Male Wistar rats having a body weight of 300-350 g are anaesthetized with thiopental (100 mg/kg i.p.). After tracheotomy, a catheter is introduced into the femoral artery to measure the blood pressure. The substances to be tested are administered as solutions, either orally by means of a gavage or intravenously via the femoral vein (Stasch et al. Br. J. Pharmacol. 2002; 135: 344-355).

B-5. Radiotelemetry Measurement of Blood Pressure in Conscious, Spontaneously Hypertensive Rats A commercially available telemetry system from DATA SCIENCES INTERNATIONAL DSI, USA, is employed for the blood pressure measurement on conscious rats described below.

The system consists of 3 main components:
implantable transmitters (Physiotel® telemetry transmitter)
receivers (Physiotel® receiver) which are linked via a multiplexer (DSI Data Exchange Matrix) to a data acquisition computer.

The telemetry system makes it possible to continuously record blood pressure, heart rate and body motion of conscious animals in their usual habitat.

Animal Material

The studies are conducted on adult female spontaneously hypertensive rats (SHR Okamoto) with a body weight of >200 g. SHR/NCrl from the Okamoto Kyoto School of Medicine, 1963, were a cross of male Wistar Kyoto rats having greatly elevated blood pressure and female rats having slightly elevated blood pressure, and were handed over at F13 to the U.S. National Institutes of Health.

After transmitter implantation, the experimental animals are housed singly in type 3 Makrolon cages. They have free access to standard feed and water.

The day/night rhythm in the experimental laboratory is changed by the room lighting at 6:00 am and at 7:00 pm.

Transmitter Implantation

The TA11 PA-C40 telemetry transmitters used are surgically implanted under aseptic conditions in the experimental animals at least 14 days before the first experimental use. The animals instrumented in this way can be used repeatedly after the wound has healed and the implant has settled.

For the implantation, the fasted animals are anaesthetized with pentobarbital (Nembutal, Sanofi: 50 mg/kg i.p.) and shaved and disinfected over a large area of their abdomens. After the abdominal cavity has been opened along the linea alba, the liquid-filled measuring catheter of the system is inserted into the descending aorta in the cranial direction above the bifurcation and fixed with tissue glue (Vet-BonD™, 3M). The transmitter housing is fixed intraperitoneally to the abdominal wall muscle, and the wound is closed layer by layer.

An antibiotic (Tardomyocel COMP, Bayer, 1 ml/kg s.c.) is administered postoperatively for prophylaxis of infection.

Substances and Solutions

Unless stated otherwise, the substances to be studied are administered orally by gavage to a group of animals in each case (n=6). In accordance with an administration volume of 5 ml/kg of body weight, the test substances are dissolved in suitable solvent mixtures or suspended in 0.5% tylose.

A solvent-treated group of animals is used as control.

Experimental Procedure

The telemetry measuring unit present is configured for 24 animals. Each experiment is recorded under an experiment number (Vyear month day).

Each of the instrumented rats living in the system is assigned a separate receiving antenna (1010 Receiver, DSI).

The implanted transmitters can be activated externally by means of an incorporated magnetic switch. They are switched to transmission in the run-up to the experiment. The signals emitted can be detected online by a data acquisition system (Dataquest™ A.R.T. for WINDOWS, DSI) and processed accordingly. The data are stored in each case in a file created for this purpose and bearing the experiment number.

In the standard procedure, the following are measured for 10-second periods in each case:
systolic blood pressure (SBP)
diastolic blood pressure (DBP)
mean arterial pressure (MAP)
heart rate (HR)
activity (ACT).

The acquisition of measurements is repeated under computer control at 5-minute intervals. The source data obtained as absolute values are corrected in the diagram with the currently measured barometric pressure (Ambient Pressure Reference Monitor; APR-1) and stored as individual data. Further technical details are given in the extensive documentation from the manufacturer company (DSI).

Unless indicated otherwise, the test substances are administered at 9:00 am on the day of the experiment. Following the administration, the parameters described above are measured over 24 hours.

Evaluation

After the end of the experiment, the acquired individual data are sorted using the analysis software (DATAQUEST™ A.R.T.™ ANALYSIS). The blank value is assumed here to be the time 2 hours before administration, and so the selected data set encompasses the period from 7:00 am on the day of the experiment to 9:00 am on the following day.

The data are smoothed over a predefinable period by determination of the average (15-minute average) and transferred as a text file to a storage medium. The measured values presorted and compressed in this way are transferred to Excel templates and tabulated. For each day of the experiment, the data obtained are stored in a dedicated file bearing the number of the experiment. Results and test protocols are stored in files in paper form sorted by numbers.

Literature

Klaus Witte, Kai Hu, Johanna Swiatek, Claudia Müssig, Georg Ertl and Björn Lemmer: Experimental heart failure in rats: effects on cardiovascular circadian rhythms and on myocardial β-adrenergic signaling. Cardiovasc Res 47 (2): 203-405, 2000; Kozo Okamoto: Spontaneous hypertension in rats. Int Rev Exp Pathol 7: 227-270, 1969; Maarten van den Buuse: Circadian Rhythms of Blood Pressure, Heart Rate, and Locomotor Activity in Spontaneously Hypertensive Rats as Measured With Radio-Telemetry. Physiology & Behavior 55(4): 783-787, 1994.

B-6. Determination of Pharmacokinetic Parameters Following Intravenous and Oral Administration The pharmacokinetic parameters of the compounds according to the invention are determined in male CD-1 mice, male Wistar rats and female beagles. Intravenous administration in the case of mice and rats is carried out by means of a species-specific plasma/DMSO formulation, and in the case of dogs by means of a water/PEG400/ethanol formulation. In all species, oral administration of the dissolved substance is performed via gavage, based on a water/PEG400/ethanol formulation. The removal of blood from rats is simplified by inserting a silicone catheter into the right Vena jugularis externa prior to substance administration. The operation is carried out at least one day prior to the experiment with isofluran anaesthesia and administration of an analgesic (atropine/rimadyl (3/1) 0.1 ml s.c.). The blood is taken (generally more than 10 time points) within a time window including terminal time points of at least 24 to a maximum of 72 hours after substance administration. The blood is removed into heparinized tubes. The blood plasma is then obtained by centrifugation; if required, it is stored at −20° C. until further processing.

An internal standard (which may also be a chemically unrelated substance) is added to the samples of the compounds of the invention, calibration samples and qualifiers, and there follows protein precipitation by means of acetonitrile in excess. Addition of a buffer solution matched to the LC conditions, and subsequent vortexing, is followed by centrifugation at 1000 g. The supernatant is analysed by LC-MS/MS using C18 reversed-phase columns and variable mobile phase mixtures. The substances are quantified via the peak heights or areas from extracted ion chromatograms of specific selected ion monitoring experiments.

The plasma concentration/time plots determined are used to calculate the pharmacokinetic parameters such as AUC, $C_{max}$, $t_{1/2}$ (terminal half-life), F (bioavailability), MRT (mean residence time) and CL (clearance), by means of a validated pharmacokinetic calculation program.

Since the substance quantification is performed in plasma, it is necessary to determine the blood/plasma distribution of the substance in order to be able to adjust the pharmacokinetic parameters correspondingly. For this purpose, a defined amount of substance is incubated in heparinized whole blood of the species in question in a rocking roller mixer for 20 min. After centrifugation at 1000 g, the plasma concentration is measured (by means of LC-MS/MS; see above) and determined by calculating the ratio of the $C_{blood}/C_{plasma}$ value.

B-7. Metabolic Study

To determine the metabolic profile of the inventive compounds, they are incubated with recombinant human cytochrome P450 (CYP) enzymes, liver microsomes or primary fresh hepatocytes from various animal species (e.g. rats, dogs), and also of human origin, in order to obtain and to compare information about a very substantially complete hepatic phase I and phase II metabolism, and about the enzymes involved in the metabolism.

The compounds of the invention were incubated with a concentration of about 0.1-10 µM. To this end, stock solutions of the compounds of the invention having a concentration of 0.01-1 mM in acetonitrile were prepared, and then pipetted with a 1:100 dilution into the incubation mixture. The liver microsomes and recombinant enzymes were incubated at 37° C. in 50 mM potassium phosphate buffer pH 7.4 with and without NADPH-generating system consisting of 1 mM $NADP^+$, 10 mM glucose-6-phosphate and 1 unit glucose-6-phosphate dehydrogenase. Primary hepatocytes were incubated in suspension in Williams E medium, likewise at 37° C. After an incubation time of 0-4 h, the incubation mixtures were stopped with acetonitrile (final concentration about 30%) and the protein was centrifuged off at about 15 000×g. The samples thus stopped were either analyzed directly or stored at −20° C. until analysis.

The analysis is carried out by high-performance liquid chromatography with ultraviolet and mass spectrometry detection (HPLC-UV-MS/MS). To this end, the supernatants of the incubation samples are chromatographed with suitable C18 reversed-phase columns and variable mobile phase mixtures of acetonitrile and 10 mM aqueous ammonium formate solution or 0.05% formic acid. The UV chromatograms in conjunction with mass spectrometry data serve for identification, structural elucidation and quantitative estimation of the metabolites, and for quantitative metabolic reduction of the compound of the invention in the incubation mixtures.

B-8. Caco-2 Permeability Test

The permeability of a test substance was determined with the aid of the Caco-2 cell line, an established in vitro model for permeability prediction at the gastrointestinal barrier (Artursson, P. and Karlsson, J. (1991). Correlation between oral drug absorption in humans and apparent drug permeability coefficients in human intestinal epithelial (Caco-2) cells. Biochem. Biophys. 175 (3), 880-885). The Caco-2 cells (ACC No. 169, DSMZ, Deutsche Sammlung von Mikroorganismen und Zellkulturen, Braunschweig, Germany) were sown in 24-well plates having an insert and cultivated for 14 to 16 days. For the permeability studies, the test substance was dissolved in DMSO and diluted to the final test concentration with transport buffer (Hanks Buffered Salt Solution, Gibco/Invitrogen, with 19.9 mM glucose and 9.8 mM HEPES). In order to determine the apical to basolateral permeability ($P_{app}$A-B) of the test substance, the solution comprising the test substance was applied to the apical side of the Caco-2 cell monolayer, and transport buffer to the basolateral side. In order to determine the basolateral to apical permeability ($P_{app}$B-A) of the test substance, the solution comprising the test substance was applied to the basolateral side of the Caco-2 cell monolayer, and transport buffer to the apical side. At the start of the experiment, samples were taken from the respective donor compartment in order to ensure the mass balance. After an incubation time of two hours at 37° C., samples were taken from the two compartments. The samples were analyzed by means of LC-MS/MS and the apparent permeability coefficients ($P_{app}$) were calculated. For each cell monolayer, the permeability of Lucifer Yellow was determined to ensure cell layer integrity. In each test run, the permeability of atenolol (marker for low permeability) and sulfasalazine (marker for active excretion) was also determined as quality control.

B-9. hERG Potassium Current Assay

The hERG (human ether-a-go-go related gene) potassium current makes a significant contribution to the repolarization of the human cardiac action potential (Scheel et al., 2011). Inhibition of this current by pharmaceuticals can in rare cases cause potentially lethal cardiac arrhythmias, and is therefore studied at an early stage during drug development.

The functional hERG assay used here is based on a recombinant HEK293 cell line which stably expresses the KCNH2(HERG) gene (Zhou et al., 1998). These cells are studied by means of the "whole-cell voltage-clamp" technique (Hamill et al., 1981) in an automated system (Patchliner™; Nanion, Munich, Germany), which controls the membrane voltage and measures the hERG potassium current at room temperature. The PatchControlHT™ software (Nanion) controls the Patchliner system, data capture and data analysis. The voltage is controlled by 2 EPC-10 quadro amplifiers controlled by the PatchMasterPro™ software (both: HEKA Elektronik, Lambrecht, Germany). NPC-16 chips with moderate resistance (~2 MΩ; Nanion) serve as the planar substrate for the voltage clamp experiments.

NPC-16 chips are filled with intra- and extracellular solution (cf. Himmel, 2007) and with cell suspension. After forming a gigaohm seal and establishing whole-cell mode (including several automated quality control steps), the cell membrane is clamped at the −80 mV holding potential. The subsequent voltage clamp protocol changes the command voltage to +20 mV (for 1000 ms), −120 mV (for 500 ms), and back to the −80 mV holding potential; this is repeated every 12 s. After an initial stabilization phase (about 5-6 minutes), test substance solution is introduced by pipette in rising concentrations (e.g. 0.1, 1, and 10 µmol/1) (exposure about 5-6 minutes per concentration), followed by several washing steps.

The amplitude of the inward "tail" current which is generated by a change in potential from +20 mV to −120 mV serves to quantify the hERG potassium current, and is described as a function of time (IgorPro™ Software). Die Stromamplitude am Ende verschiedener Zeitabschnitte (z.B. Stabilisierungsphase vor Testsubstanz, erste/zweite/dritte Konzentration Testsubstanz) dient zur Erstellung einer Konzentrations-Wirkungs-Kurve, aus der die halbmaximale Hemmkonzentration $IC_{50}$ der Testsubstanz errechnet wird.

Hamill O P, Marty A, Neher E, Sakmann B, Sigworth F J. Improved patch-clamp techniques for high-resolution current recording from cells and cell-free membrane patches. Pfluegers Arch 1981; 391:85-100.

Himmel H M. Suitability of commonly used excipients for electrophysiological in-vitro safety pharmacology assessment of effects on hERG potassium current and on rabbit Purkinje fiber action potential. J Pharmacol Toxicol Methods 2007; 56:145-158.

Scheel O, Himmel H, Rascher-Eggstein G, Knott T. Introduction of a modular automated voltage-clamp platform and its correlation with manual human ether-a-go-go related gene voltage-clamp data. Assay Drug Dev Technol 2011; 9:600-607.

Zhou Z F, Gong Q, Ye B, Fan Z, Makielski J C, Robertson G A, January C T. Properties of hERG channels stably expressed in HEK293 cells studied at physiological temperature. Biophys J 1998; 74:230-241.

C. WORKING EXAMPLES OF PHARMACEUTICAL COMPOSITIONS

The compounds of the invention can be converted to pharmaceutical preparations as follows:

Tablet:
Composition:
100 mg of the compound of the invention, 50 mg of lactose (monohydrate), 50 mg of corn starch (native), 10 mg of polyvinylpyrrolidone (PVP 25) (BASF, Ludwigshafen, Germany) and 2 mg of magnesium stearate.

Tablet weight 212 mg. Diameter 8 mm, radius of curvature 12 mm.
Production:
The mixture of compound of the invention, lactose and starch is granulated with a 5% solution (w/w) of the PVP in water. The granules are dried and then mixed with the magnesium stearate for 5 minutes. This mixture is compressed using a conventional tableting press (see above for format of the tablet). The guide value used for the pressing is a pressing force of 15 kN.

Suspension for Oral Administration:
Composition:
1000 mg of the compound of the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound of the invention.
Production:
The Rhodigel is suspended in ethanol; the compound of the invention is added to the suspension. The water is added while stirring. The mixture is stirred for about 6 h until the swelling of the Rhodigel is complete.

Solution for Oral Administration:
Composition:
500 mg of the compound of the invention, 2.5 g of polysorbate and 97 g of polyethylene glycol 400. 20 g of oral solution correspond to a single dose of 100 mg of the compound of the invention.
Production:
The compound of the invention is suspended in the mixture of polyethylene glycol and polysorbate with stirring. The stirring operation is continued until dissolution of the compound of the invention is complete.

I.V. Solution:
The compound of the invention is dissolved in a concentration below the saturation solubility in a physiologically acceptable solvent (e.g. isotonic saline solution, glucose solution 5% and/or PEG 400 solution 30%). The resulting solution is subjected to sterile filtration and dispensed into sterile and pyrogen-free injection vessels.

The invention claimed is:
1. A compound of the formula (I-A)

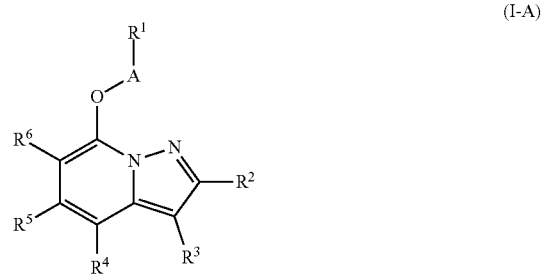

in which
A represents $CH_2$, $CD_2$ or $CH(CH_3)$,
$R^1$ represents $(C_4-C_6)$-alkyl, $(C_3-C_7)$-cycloalkyl, pyridyl or phenyl,
where $(C_4-C_6)$-alkyl may be up to hexasubstituted by fluorine,
where $(C_3-C_7)$-cycloalkyl may be substituted by 1 to 4 substituents independently of one another selected from the group consisting of fluorine, trifluoromethyl and $(C_1-C_4)$-alkyl,
where pyridyl is substituted by 1 or 2 substituents independently of one another selected from the group consisting of halogen, cyano and $(C_1-C_4)$-alkyl,
and
where phenyl may be substituted by 1 to 4 substituents independently of one another selected from the group consisting of halogen, cyano, monofluoromethyl, difluoromethyl, trifluoromethyl, $(C_1-C_4)$-alkyl and $(C_1-C_4)$-alkoxy,
$R^2$ represents hydrogen, $(C_1-C_4)$-alkyl, $(C_1-C_4)$-alkoxymethyl, cyclopropyl, cyclobutyl, monofluoromethyl, difluoromethyl or trifluoromethyl,
$R^3$ represents phenyl or 5- to 10-membered heteroaryl,
where phenyl may be substituted by 1 to 3 substituents independently of one another selected from the group of halogen, cyano, trifluoromethyl, difluoromethyl, $(C_1-C_6)$-alkyl, $(C_1-C_4)$-alkoxycarbonyl, $(C_1-C_4)$-alkylcarbonyl, hydroxycarbonyl, —(C═O)$NR^7R^8$, $(C_1-C_4)$-alkylsulphonyl, $(C_3-C_6)$-cycloalkylsulphonyl, $(C_1-C_4)$-alkylthio, $(C_1-C_4)$-alkoxy, trifluoromethoxy, difluoromethoxy, phenoxy, hydroxy, amino, morpholinyl, piperidinyl, pyrrolidinyl, piperazinyl, and $(C_3-C_6)$-cycloalkyl, in which amino may be substituted by 1 or 2 substituents independently of one another selected from the group consisting of $(C_1-C_6)$-alkyl (which $(C_1-C_6)$-alkyl may be substituted by amino), $(C_1-C_4)$-alkylcarbonyl, $(C_3-C_6)$-cycloalkylsulphonyl, $(C_1-C_4)$-alkylsulphonyl and methoxy-$(C_1-C_4)$-alkyl, in which the $(C_1-C_6)$-alkyl substituent on the phenyl may be substituted by 1 or 2 substituents selected from the group consisting of fluorine, trifluoromethoxy, —(C=O)NR$^7$R$^8$, $(C_1-C_4)$-alkoxy, $(C_3-C_6)$-cycloalkyl, morpholinyl, piperidinyl, pyrrolidinyl, piperazinyl, hydroxy and amino (which amino may be substituted by 1 or 2 substituents independently of one another selected from the group consisting of $(C_1-C_6)$-alkyl, $(C_1-C_4)$-alkylcarbonyl, $(C_1-C_4)$-alkoxycarbonyl, $(C_3-C_6)$-cycloalkylsulphonyl, $(C_1-C_4)$-alkylsulphonyl and methoxy-$(C_1-C_4)$-alkyl), and in which $R^7$ and $R^8$ each independently of one another represent hydrogen, $(C_1-C_4)$-alkyl or $(C_3-C_7)$-cycloalkyl, where 5- to 10-membered heteroaryl may be substituted by 1 to 3 substituents independently of one another selected from the group consisting of fluorine, chlorine, cyano, $(C_1-C_6)$-alkyl, $(C_1-C_4)$-alkoxy, amino, $(C_1-C_4)$-alkoxycarbonyl, hydroxycarbonyl, —(C=O)NR$^7$R$^8$, phenyl, pyridyl, pyrimidyl, 1,3-thiazol-5-yl, pyrrolidinyl, piperidinyl, morpholinyl, piperazinyl and $(C_3-C_7)$-cycloalkyl, in which $(C_1-C_6)$-alkyl may be substituted by 1 to 3 substituents selected from the group consisting of fluorine, cyano, hydroxy, amino, trifluoromethyl, difluoromethyl, $(C_1-C_4)$-alkylsulphonyl, $(C_1-C_4)$-alkylcarbonyl, $(C_1-C_4)$-alkoxycarbonyl, hydroxycarbonyl, —(C=O)NR$^7$R$^8$, $(C_1-C_4)$-alkoxy, phenoxy, phenyl, pyridyl, pyrimidyl, 5-membered heteroaryl, $(C_3-C_7)$-cycloalkyl, morpholinyl, piperidinyl, pyrrolidinyl, piperazinyl, 1,1-dioxidothiomorpholin-4-yl and azetidinyl, in which 5-membered heteroaryl may be substituted by 1 to 3 substituents selected from the group consisting of halogen, $(C_1-C_4)$-alkyl and $(C_1-C_4)$-alkoxy, in which $R^7$ and $R^8$ each independently of one another represent hydrogen, $(C_1-C_4)$-alkyl or $(C_3-C_7)$-cycloalkyl, in which piperidinyl substituent on the $(C_1-C_6)$-alkyl that is a substituent on the 5- to 10-membered heteroaryl is a piperidinyl that may be substituted by 1 to 4 fluorine substituents, in which phenyl substituent on the $(C_1-C_6)$-alkyl that is a substituent on the 5- to 10-membered heteroaryl is a phenyl that may be substituted by 1 to 3 substituents selected from the group consisting of halogen, $(C_1-C_4)$-alkyl and $(C_1-C_4)$-alkoxy, in which azetidinyl may be substituted by hydroxy, in which amino substituent on the $(C_1-C_6)$-alkyl that is a substituent on the 5- to 10-membered heteroaryl is amino that may be substituted by 1 or 2 $(C_1-C_4)$-alkyl substituents, and in which piperazinyl on the $(C_1-C_6)$-alkyl that is a substituent on the 5- to 10-membered heteroaryl may be substituted by 1 to 3 substituents independently of one another selected from the group consisting of $(C_1-C_4)$-alkyl, $(C_3-C_7)$-cycloalkyl and trifluoromethyl, in which $(C_3-C_7)$-cycloalkyl substituent on the 5- to 10-membered heteroaryl may be substituted by 1 or 2 substituents independently of one another selected from the group consisting of halogen, $(C_1-C_6)$-alkyl, $(C_1-C_4)$-alkoxycarbonyl and hydroxycarbonyl, in which $(C_1-C_4)$-alkoxy substituent on the 5- to 10-membered heteroaryl may be substituted by amino, in which amino substituent on the 5- to 10-membered heteroaryl may be substituted by 1 or 2 substituents independently of one another selected from $(C_1-C_6)$-alkyl (which $(C_1-C_6)$-alkyl may be substituted by amino and may be substituted up to five times by fluorine), $(C_1-C_4)$-alkylcarbonyl, $(C_3-C_6)$-cycloalkylsulphonyl and $(C_1-C_4)$-alkylsulphonyl, in which phenyl, pyridyl and pyrimidyl substituent on the 5- to 10-membered heteroaryl may be substituted by 1 or 2 substituents selected from the group consisting of methyl, ethyl and fluorine, in which $R^7$ and $R^8$ each independently of one another represent hydrogen, $(C_1-C_4)$-alkyl or $(C_3-C_7)$-cycloalkyl, or $R^3$ represents a group of the formula

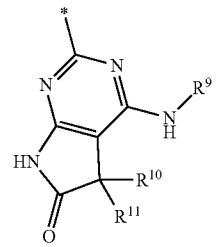

where

* represents the point of attachment to the pyrazolopyridine, $R^9$ represents hydrogen or $(C_1-C_6)$-alkyl, where $(C_1-C_6)$-alkyl may be substituted by amino, and in which $(C_1-C_6)$-alkyl may be substituted up to five times by fluorine, $R^{10}$ represents hydrogen, methyl or ethyl, $R^{11}$ represents hydrogen, methyl, ethyl, trifluoromethyl or cyclopropyl, or $R^{10}$ and $R^{11}$ together with the carbon atom to which they are attached form a 3- to 6-membered carbocycle, $R^4$ represents hydrogen, $R^5$ represents hydrogen, halogen, cyano, difluoromethyl, trifluoromethyl, $(C_1-C_4)$-alkyl, $(C_3-C_7)$-cycloalkyl, $(C_2-C_4)$-alkynyl, $(C_1-C_4)$-alkylamino, difluoromethoxy, trifluoromethoxy, $(C_1\text{-}C_4)$-alkoxy, amino, 4- to 7-membered heterocyclyl or 5- or 6-membered heteroaryl, $R^6$ represents hydrogen, cyano or halogen, and the N-oxides, salts, solvates, salts of the N-oxides and solvates of the N-oxides and salts thereof.

2. The compound of the formula (I-A) as claimed in claim 1 in which

A represents $CH_2$ or $CD_2$, $R^1$ represents cyclohexyl, pyridyl or phenyl,
  where cyclohexyl may be substituted up to four times by fluorine,
  where pyridyl is substituted by 1 or 2 fluorine substituents,
  and
  where phenyl may be substituted by 1 to 4 substituents independently of one another selected from the group consisting of fluorine, chlorine, cyano, methyl and methoxy, $R^2$ represents hydrogen, $(C_1\text{-}C_4)$-alkyl, cyclopropyl, difluoromethyl or trifluoromethyl, $R^3$ represents phenyl or 5- or 6-membered heteroaryl,
  where phenyl may be substituted by 1 to 3 substituents independently of one another selected from the group consisting of fluorine, chlorine, cyano, trifluoromethyl, difluoromethyl, $(C_1\text{-}C_6)$-alkyl, $(C_1\text{-}C_4)$-alkoxycarbonyl, $(C_1\text{-}C_4)$-alkylcarbonyl, hydroxycarbonyl, —(C=O)NR$^7$R$^8$, $(C_1\text{-}C_4)$-alkylsulphonyl, $(C_3\text{-}C_6)$-cycloalkylsulphonyl, $(C_1\text{-}C_4)$-alkoxy, trifluoromethoxy, difluoromethoxy, hydroxy, amino, morpholinyl, piperidinyl, pyrrolidinyl, piperazinyl and cyclopropyl,
    in which amino may be substituted by 1 or 2 substituents independently of one another selected from $(C_1\text{-}C_6)$-alkyl, $(C_1\text{-}C_4)$-alkylcarbonyl and $(C_1\text{-}C_4)$-alkylsulphonyl,
    in which the $(C_1\text{-}C_6)$-alkyl substituent on the phenyl may be substituted by 1 or 2 substituents selected from the group consisting of fluorine, trifluoromethoxy, —(C=O)NR$^7$R$^8$, $(C_1\text{-}C_4)$-alkoxy, $(C_3\text{-}C_6)$-cycloalkyl, morpholinyl, piperidinyl, pyrrolidinyl, piperazinyl, hydroxyl and amino (which amino may be substituted by 1 or 2 substituents independently of one another selected from $(C_1\text{-}C_6)$-alkyl, $(C_1\text{-}C_4)$-alkylcarbonyl and $(C_1\text{-}C_4)$-alkylsulphonyl),
    and in which
    $R^7$ and $R^8$ each independently of one another represent hydrogen, $(C_1\text{-}C_4)$-alkyl or cyclopropyl,
  where 5- or 6-membered heteroaryl may be substituted by 1 to 3 substituents independently of one another selected from the group consisting of fluorine, chlorine, cyano, $(C_1\text{-}C_6)$-alkyl, $(C_1\text{-}C_4)$-alkoxy, amino, $(C_1\text{-}C_4)$-alkoxycarbonyl, hydroxycarbonyl, —(C=O)NR$^7$R$^8$, phenyl, pyridyl, pyrimidyl, pyrrolidinyl, piperidinyl, morpholinyl, piperazinyl and cyclopropyl,
    in which $(C_1\text{-}C_6)$-alkyl may be substituted by 1 to 3 substituents selected from the group consisting of fluorine, cyano, hydroxy, amino, trifluoromethyl, difluoromethyl, $(C_1\text{-}C_4)$-alkylsulphonyl, $(C_1\text{-}C_4)$-alkoxycarbonyl, hydroxycarbonyl, —(C=O)NR$^7$R$^8$, $(C_1\text{-}C_4)$-alkoxy, phenyl, pyridyl, pyrimidyl, 5-membered heteroaryl, $(C_3\text{-}C_7)$-cycloalkyl, morpholinyl, piperidinyl, pyrrolidinyl, piperazinyl, 1,1-dioxidothiomorpholin-4-yl and azetidinyl,
      in which 5-membered heteroaryl may be substituted by 1 to 3 substituents selected from the group consisting of fluorine, chlorine, methyl, ethyl and methoxy,
    in which
      $R^7$ and $R^8$ each independently of one another represent hydrogen, methyl, ethyl or cyclopropyl,
      in which the piperidinyl substituent on the $(C_1\text{-}C_6)$-alkyl that is a substituent on the 5- or 6-membered heteroaryl is a piperidinyl that may be substituted by 1 to 4 fluorine substituents,
      in which the phenyl substituent that is on the $(C_1\text{-}C_6)$-alkyl that is a substituent on the 5- or 6-membered heteroaryl is a phenyl that may be substituted by 1 to 3 substituents selected from the group consisting of fluorine, methyl, ethyl and methoxy,
    in which amino substituent on the 5- or 6-membered heteroaryl may be substituted by 1 or 2 substituents independently of one another selected from $(C_1\text{-}C_6)$-alkyl (which $(C_1\text{-}C_6)$-alkyl may be substituted by amino) and $(C_1\text{-}C_4)$-alkylcarbonyl,
    in which phenyl, pyridyl and pyrimidyl substituents on the 5- or 6-membered heteroaryl may be substituted by 1 or 2 substituents selected from the group consisting of methyl, ethyl and fluorine,
    and in which
    $R^7$ and $R^8$ each independently of one another represent hydrogen, methyl, ethyl or cyclopropyl,
or
$R^3$ represents a group of the formula

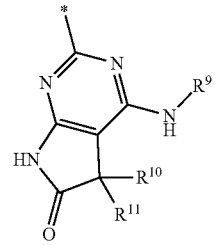

where
* represents the point of attachment to the pyrazolopyridine,
$R^9$ represents hydrogen or $(C_1\text{-}C_6)$-alkyl,
  where $(C_1\text{-}C_6)$-alkyl may be substituted by amino,
$R^{10}$ represents methyl or ethyl,
$R^{11}$ represents methyl, ethyl, trifluoromethyl or cyclopropyl,
$R^4$ represents hydrogen,
$R^5$ represents hydrogen, fluorine, chlorine, cyano, difluoromethyl, trifluoromethyl, $(C_1\text{-}C_4)$-alkyl or $(C_3\text{-}C_5)$-cycloalkyl,
$R^6$ represents hydrogen,
and the N-oxides, salts, solvates, salts of the N-oxides and solvates of the N-oxides and salts thereof.

3. The compound of the formula (I-A) according to claim 1 in which

A represents $CH_2$ or $CD_2$, $R^1$ represents cyclohexyl, pyridyl or phenyl,
  where cyclohexyl may be substituted up to four times by fluorine, where pyridyl is substituted by 1 or 2 fluorine substituents,
and
where phenyl may be substituted by 1 to 4 substituents independently of one another selected from the group consisting of fluorine, chlorine, cyano, methyl and methoxy, $R^2$ represents hydrogen, $(C_1-C_4)$-alkyl, cyclopropyl, difluoromethyl or trifluoromethyl, $R^3$ represents phenyl or 5- or 6-membered heteroaryl,
where phenyl may be substituted by 1 to 3 substituents independently of one another selected from the group consisting of fluorine, chlorine, cyano, trifluoromethyl, difluoromethyl, $(C_1-C_6)$-alkyl, $(C_1-C_4)$-alkoxycarbonyl, $(C_1-C_4)$-alkylcarbonyl, hydroxycarbonyl, —(C=O)NR$^7$R$^8$, $(C_1-C_4)$-alkylsulphonyl, $(C_3-C_6)$-cycloalkylsulphonyl, $(C_1-C_4)$-alkoxy, trifluoromethoxy, difluoromethoxy, hydroxy, amino, morpholinyl, piperidinyl, pyrrolidinyl, piperazinyl and cyclopropyl,
in which amino may be substituted by 1 or 2 substituents independently of one another selected from $(C_1-C_6)$-alkyl, $(C_1-C_4)$-alkylcarbonyl and $(C_1-C_4)$-alkylsulphonyl,
in which the $(C_1-C_6)$-alkyl substituent on the phenyl may be substituted by 1 or 2 substituents selected from the group consisting of fluorine, trifluoromethoxy, —(C=O)NR$^7$R$^8$, $(C_1-C_4)$-alkoxy, $(C_3-C_6)$-cycloalkyl, morpholinyl, piperidinyl, pyrrolidinyl, piperazinyl, hydroxy and amino (which amino may be substituted by 1 or 2 substituents independently of one another selected from $(C_1-C_6)$-alkyl, $(C_1-C_4)$-alkylcarbonyl and $(C_1-C_4)$-alkylsulphonyl),
and in which
$R^7$ and $R^8$ each independently of one another represent hydrogen, $(C_1-C_4)$-alkyl or cyclopropyl,
where 5- or 6-membered heteroaryl may be substituted by 1 to 3 substituents independently of one another selected from the group consisting of fluorine, chlorine, cyano, $(C_1-C_6)$-alkyl, $(C_1-C_4)$-alkoxy, amino, $(C_1-C_4)$-alkoxycarbonyl, hydroxycarbonyl, —(C=O)NR$^7$R$^8$, phenyl, pyridyl, pyrimidyl, pyrrolidinyl, piperidinyl, morpholinyl, piperazinyl and cyclopropyl,
in which $(C_1-C_6)$-alkyl may be substituted by 1 to 3 substituents selected from the group consisting of fluorine, cyano, hydroxy, amino, trifluoromethyl, difluoromethyl, $(C_1-C_4)$-alkylsulphonyl, $(C_1-C_4)$-alkoxycarbonyl, hydroxycarbonyl, —(C=O)NR$^7$R$^8$, $(C_1-C_4)$-alkoxy, phenyl, pyridyl, pyrimidyl, 5-membered heteroaryl, $(C_3-C_7)$-cycloalkyl, morpholinyl, piperidinyl, pyrrolidinyl, piperazinyl, 1,1-dioxidothiomorpholin-4-yl and azetidinyl,
in which 5-membered heteroaryl may be substituted by 1 to 3 substituents selected from the group consisting of fluorine, chlorine, methyl, ethyl and methoxy,
in which
$R^7$ and $R^8$ each independently of one another represent hydrogen, methyl, ethyl or cyclopropyl,
in which the piperidinyl substituent on the $(C_1-C_6)$-alkyl that is a substituent on the 5- or 6-membered heteroaryl is a piperidinyl that may be substituted by 1 to 4 fluorine substituents,
in which the phenyl substituent on the $(C_1-C_6)$-alkyl that is a substituent on the 5- or 6-membered heteroaryl is a phenyl that may be substituted by 1 to 3 substituents selected from the group consisting of fluorine, methyl, ethyl and methoxy,
in which amino substituent on the 5- or 6-membered heteroaryl may be substituted by 1 or 2 substituents independently of one another selected from $(C_1-C_6)$-alkyl (which $(C_1-C_6)$-alkyl may be substituted by amino) and $(C_1-C_4)$-alkylcarbonyl,
in which phenyl, pyridyl and pyrimidyl substituents on the 5- or 6-membered heteroaryl may be substituted by 1 or 2 substituents selected from the group consisting of methyl, ethyl and fluorine,
and in which
$R^7$ and $R^8$ each independently of one another represent hydrogen, methyl, ethyl or cyclopropyl, $R^4$ represents hydrogen,
$R^5$ represents hydrogen, fluorine, chlorine, cyano, difluoromethyl, trifluoromethyl, $(C_1-C_4)$-alkyl or $(C_3-C_5)$-cycloalkyl,
$R^6$ represents hydrogen,
and the N-oxides, salts, solvates, salts of the N-oxides and solvates of the N-oxides and salts thereof.

4. The compound of the formula (I-A) according to claim 1, in which
A represents CH$_2$,
$R^1$ represents phenyl,
where phenyl is substituted up to three times by fluorine,
$R^2$ represents methyl,
$R^3$ represents phenyl, pyridyl, pyrimidyl or 4-pyrazolyl,
where phenyl may be substituted by 1 to 3 substituents independently of one another selected from the group consisting of fluorine, $(C_1-C_6)$-alkyl, hydroxycarbonyl, —(C=O)NR$^7$R$^8$, methylsulphonyl, ethylsulphonyl, amino, morpholinyl, piperidinyl, pyrrolidinyl and piperazinyl,
in which amino may be substituted by 1 or 2 substituents independently of one another selected from $(C_1-C_6)$-alkyl, methylcarbonyl, ethylcarbonyl, methylsulphonyl and ethylsulphonyl,
in which the $(C_1-C_6)$-alkyl substituent on the phenyl may be substituted by 1 or 2 substituents selected from the group consisting of fluorine, morpholinyl, piperidinyl, pyrrolidinyl, piperazinyl and amino,
in which the amino on the $(C_1-C_6)$-alkyl substituent on the phenyl is an amino that may be substituted by 1 or 2 substituents independently of one another selected from $(C_1-C_4)$-alkyl, methylcarbonyl, ethylcarbonyl, methylsulphonyl and ethylsulphonyl,
and in which
$R^7$ and $R^8$ each independently of one another represent hydrogen or cyclopropyl,
where pyridyl and 4-pyrazolyl may be substituted by 1 or 2 substituents independently of one another selected from the group consisting of fluorine, chlorine, $(C_1-C_6)$-alkyl, methoxy, amino, hydroxycarbonyl, —(C=O)NR$^7$R$^8$, phenyl, pyridyl, pyrrolidinyl, piperidinyl, morpholinyl and piperazinyl, in which the $(C_1-C_6)$-alkyl on the pyridyl and 4-pyrazolyl may be substituted by 1 to 3 substituents selected from the group consisting of fluorine, hydroxy, amino, hydroxycarbonyl, —(C=O)NR$^7$R$^8$, methoxy, phenyl, pyridyl, pyrazolyl, $(C_3-C_7)$-cycloalkyl, morpholinyl, piperidinyl, pyrrolidinyl and piperazinyl,
in which pyrazolyl may be substituted by 1 or 2 methyl substituents,
and in which
R$^7$ and R$^8$ each independently of one another represent hydrogen, methyl, ethyl or cyclopropyl,
in which the amino on the pyridyl and 4-pyrazolyl may be substituted by 1 or 2 $(C_1-C_6)$-alkyl substituents (which $(C_1-C_6)$-alkyl may be substituted by amino),
in which phenyl, pyridyl and pyrimidyl substituents on the pyridyl and 4-pyrazolyl may be substituted by 1 or 2 substituents selected from the group consisting of methyl, ethyl and fluorine,
and in which
R$^7$ and R$^8$ each independently of one another represent hydrogen, methyl or cyclopropyl,
R$^4$ represents hydrogen,
R$^5$ represents hydrogen or methyl,
R$^6$ represents hydrogen,
and the N-oxides, salts, solvates, salts of the N-oxides and solvates of the N-oxides and salts thereof.

5. The compound of the formula (I-A) according to, claim 1 in which
A represents CH$_2$,
R$^1$ represents a phenyl group of the formula

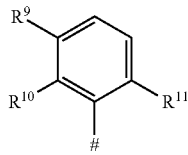

where
# represents the point of attachment to A,
and
R$^9$ represents hydrogen or fluorine,
R$^{10}$ represents fluorine,
R$^{11}$ represents fluorine,
R$^2$ represents methyl,
R$^3$ represents phenyl, 3-pyridyl, 4-pyridyl or 4-pyrazolyl,
where phenyl in the 3-position may be substituted by fluorine, $(C_1-C_6)$-alkyl, hydroxycarbonyl, —(C=O)NR$^7$R$^8$, methylsulphonyl, ethylsulphonyl, amino, morpholinyl, piperidinyl, pyrrolidinyl and piperazinyl,
in which amino may be substituted by 1 or 2 substituents independently of one another selected from $(C_1-C_6)$-alkyl, methylcarbonyl, ethylcarbonyl, methylsulphonyl and ethylsulphonyl,
in which the $(C_1-C_6)$-alkyl substituent on the phenyl may be substituted by 1 or 2 substituents selected from the group consisting of fluorine, morpholinyl, piperidinyl, pyrrolidinyl, piperazinyl and amino,
in which the amino substituent on the $(C_1-C_6)$-alkyl that is a substituent on the phenyl is amino that may be substituted by 1 or 2 substituents independently of one another selected from $(C_1-C_4)$-alkyl, methylcarbonyl, ethylcarbonyl, methylsulphonyl and ethylsulphonyl,
and in which
R$^7$ and R$^8$ each independently of one another represent hydrogen or cyclopropyl,
where 3-pyridyl and 4-pyridyl may each be substituted by 1 or 2 substituents independently of one another selected from the group consisting of fluorine, chlorine, $(C_1-C_6)$-alkyl, methoxy, amino, hydroxycarbonyl, —(C=O)NR$^7$R$^8$, phenyl, pyridyl, pyrrolidinyl, piperidinyl, morpholinyl and piperazinyl,
in which amino may be substituted by 1 or 2 $(C_1-C_6)$-alkyl substituents (which $(C_1-C_6)$-alkyl may be substituted by amino),
in which phenyl, pyridyl and pyrimidyl substituents on the pyridyl and 4-pyrazolyl may be substituted by 1 or 2 substituents selected from the group consisting of methyl, ethyl and fluorine,
and in which
R$^7$ and R$^8$ each independently of one another represent hydrogen, methyl or cyclopropyl,
where 4-pyrazolyl may be substituted at the 1-position by $(C_1-C_6)$-alkyl, phenyl or pyridyl,
in which the $(C_1-C_6)$-alkyl on the 4-pyrazolyl may be substituted by 1 to 3 substituents selected from the group consisting of fluorine, hydroxy, amino, methoxycarbonyl, ethoxycarbonyl, hydroxycarbonyl, —(C=O)NR$^7$R$^8$, methoxy, phenyl, pyridyl, pyrazolyl, $(C_3-C_7)$-cycloalkyl, morpholinyl, piperidinyl, pyrrolidinyl and piperazinyl, in which pyrazolyl may be substituted by 1 to 3 methyl substituents,
in which
R$^7$ and R$^8$ each independently of one another represent hydrogen, methyl, ethyl or cyclopropyl,
in which phenyl and pyridyl may be substituted by 1 or 2 substituents selected from the group consisting of methyl, ethyl and fluorine,
R$^4$ represents hydrogen,
R$^5$ represents hydrogen or methyl,
R$^6$ represents hydrogen,
and the N-oxides, salts, solvates, salts of the N-oxides and solvates of the N-oxides and salts thereof.

6. The compound of the formula (I-A) according to claim 1, in which
A represents CH$_2$,
R$^1$ represents a phenyl group of the formula

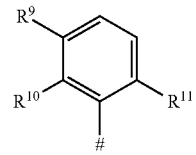

where
# represents the point of attachment to A,
and
R$^9$ represents hydrogen or fluorine,
R$^{10}$ represents fluorine,
R$^{11}$ represents fluorine,
R$^2$ represents methyl,
R$^3$ represents phenyl, 3-pyridyl, 4-pyridyl or 4-pyrazolyl, where phenyl in the 3-position may be substituted by $(C_1-C_6)$-alkyl, hydroxycarbonyl, —(C=O)NR$^7$R$^8$, methylsulphonyl, ethylsulphonyl, amino and pyrrolidinyl,
- in which amino may be substituted by 1 or 2 substituents independently of one another selected from $(C_1-C_6)$-alkyl, methylcarbonyl and methylsulphonyl,
- in which the $(C_1-C_6)$-alkyl that is a substituent on the phenyl may be substituted by 1 or 2 substituents selected from the group consisting of fluorine, pyrrolidinyl and amino (which amino may be substituted by 1 or 2 substituents independently of one another selected from $(C_1-C_4)$-alkyl, methylcarbonyl and methylsulphonyl),
- and in which
- R$^7$ and R$^8$ each independently of one another represent hydrogen or cyclopropyl, where 3-pyridyl and 4-pyridyl may each be substituted by 1 or 2 substituents independently of one another selected from the group consisting of fluorine, chlorine, $(C_1-C_6)$-alkyl, amino, hydroxycarbonyl, —(C=O)NR$^7$R$^8$, phenyl and piperazinyl,
- in which amino may be substituted by 1 or 2 $(C_1-C_6)$-alkyl substituents (which $(C_1-C_6)$-alkyl substituents may be substituted by amino),
- in which phenyl may be substituted by 1 or 2 substituents selected from the group consisting of methyl, ethyl and fluorine,
- and in which
- R$^7$ and R$^8$ each represent hydrogen, where 4-pyrazolyl may be substituted at the 1-position by $(C_1-C_6)$-alkyl or phenyl,
- in which $(C_1-C_6)$-alkyl may be substituted by 1 to 3 substituents selected from the group consisting of hydroxy, amino, methoxycarbonyl, hydroxycarbonyl, —(C=O)NR$^7$R$^8$, phenyl, pyrazolyl, $(C_3-C_7)$-cycloalkyl and morpholinyl,
  - in which pyrazolyl may be substituted by 1 or 3 methyl substituents,
  - in which
  - R$^7$ represents hydrogen,
  - R$^8$ represents cyclopropyl,
  - in which phenyl and pyridyl may be substituted by 1 or 2 fluorine substituents, R$^4$ represents hydrogen,
R$^5$ represents hydrogen or methyl,
R$^6$ represents hydrogen,
and the N-oxides, salts, solvates, salts of the N-oxides and solvates of the N-oxides and salts thereof.

7. A medicament comprising the compound of the formula (I-A) as defined in claim 1 in combination with an inert, non-toxic, pharmaceutically suitable excipient.

* * * * *